United States Patent
Kim et al.

(10) Patent No.: US 12,006,502 B2
(45) Date of Patent: Jun. 11, 2024

(54) THERAPEUTIC COMPOUNDS FOR RED BLOOD CELL-MEDIATED DELIVERY OF AN ACTIVE PHARMACEUTICAL INGREDIENT TO A TARGET CELL

(71) Applicants: KIST (Korea Institute of Science and Technology), Seoul (KR); K2B Therapeutics, Inc., Cambridge, MA (US)

(72) Inventors: HoWon J. Kim, Lexington, MA (US); In-San Kim, Seoul (KR); Jay S. Kim, Bedford, MA (US); Sun Hwa Kim, Seoul (KR); Ick Chan Kwon, Seoul (KR); Jong Won Lee, Seoul (KR); Yoo Soo Yang, Seoul (KR); Hong Yeol Yoon, Gyeonggi-do (KR)

(73) Assignees: K2B Therapeutics, Inc., Cambridge, MA (US); KIST (Korea Institute of Science and Technology), Seoul (KR)

( * ) Notice: Subject to any disclaimer, the term of this patent is extended or adjusted under 35 U.S.C. 154(b) by 0 days.

(21) Appl. No.: 18/407,815

(22) Filed: Jan. 9, 2024

(65) Prior Publication Data

US 2024/0150771 A1 May 9, 2024

Related U.S. Application Data

(63) Continuation of application No. 18/057,050, filed on Nov. 18, 2022.

(60) Provisional application No. 63/392,323, filed on Jul. 26, 2022, provisional application No. 63/281,370, filed on Nov. 19, 2021.

(51) Int. Cl.
| | |
|---|---|
| *C12N 15/113* | (2010.01) |
| *A61P 35/00* | (2006.01) |
| *C12Q 1/68* | (2018.01) |

(52) U.S. Cl.
CPC .......... *C12N 15/1138* (2013.01); *A61P 35/00* (2018.01); *C12N 2310/11* (2013.01); *C12N 2310/531* (2013.01)

(58) Field of Classification Search
None
See application file for complete search history.

(56) References Cited

U.S. PATENT DOCUMENTS

| 2021/0015931 A1 | 1/2021 | Kim et al. |
| 2022/0257729 A1 | 8/2022 | Cochran et al. |

FOREIGN PATENT DOCUMENTS

| EP | 3575326 A1 | 12/2019 |
| WO | 2014149477 A1 | 9/2014 |
| WO | 2020163721 A1 | 8/2020 |
| WO | 2021174127 A1 | 9/2021 |

OTHER PUBLICATIONS

Ratnikova et al., "CD47 Receptor as a Primary Target for Cancer Therapy", Molecular Biology, vol. 51, No. 2, pp. 216-225, May 9, 2017.
International Searching Authority—International Search Report, pertaining to International Application No. PCT/US2023/080167 dated May 8, 2023, together with the Written Opinion of the International Searching Authority, 14 pages.
Tatiparti et al., "siRNA Delivery Strategies: A Comprehensive Review of Recent Developments", Nanomaterials, vol. 7, 77, 17 pages, 2017.
Singh et al., "Advances in siRNA delivery in cancer therapy", Artificial Cells, Nanomedicine, and Biotechnology, 46:2, 274-283, 2018.
Resnier et al., "A review of the current status of siRNA nanomedicines in the treatment of cancer", Biomaterials, vol. 34, pp. 6429-6443, 2013.
Boyd et al., "New approaches to genetic therapies for cystic fibrosis", Journal of Cystic Fibrosis, vol. 19, pp. S54-S56, 2020.
Wang et al., "Strategies for short hairpin RNA delivery in cancer gene therapy", Expert Opinion on Biological Therapy, 9:11. pp. 1357-1369, 2009.
Ho et al., "Biomaterials in siRNA Delivery: A Comprehensive Review", Advanced Healthcare Materials, vol. 5, pp. 2715-2731, 2016.
Qureshi et al., "A review on current status of antiviral siRNA", Rev. Med. Virol., vol. 28, 11 pages, 2018.
Kim et al., "Recent progress in development of siRNA delivery vehicles for cancer therapy", Advanced Drug Delivery Reviews, vol. 104, pp. 61-77, 2016.
Yonezawa et al., "Recent advances in siRNA delivery mediated by lipid-based nanoparticles", Advanced Drug Delivery Reviews, vols. 154-155, pp. 64-78, 2020.
Gondi et al., "Concepts in In Vivo siRNA Delivery for Cancer Therapy", Journal of Cellular Physiology, vol. 220, pp. 285-291, 2009.
Ko et al., Versatile activatable vSIRPα-probe for cancer-targeted imaging and macrophage-medicated phagocytosis of cancer cells:, Journal of Controlled Release, vol. 323, pp. 376-386, 2020.
Acharya, "The recent progresses in shRNA-nanoparticle conjugate as a therapeutic approach", Materials Science & Engineering C, vol. 104, 109928, 8 pages, 2019.
Rao et al., "siRNA vs. shRNA: Similarities and differences", Advanced Drug Delivery Reviews, vol. 61, pp. 746-759, 2009.
McLaughlin et al., "CD47 as a potential biomarker for the early diagnosis of severe COVID-19", bioRxiv, 35 pages, 2021.
Cham et al., "Immunotherapeutic Blockade of CD47 Inhibitory Signaling Enhances Innate and Adaptive Immute Responses to Viral Infection", Cell Reports, vol. 31, 107494, 14 pages, Apr. 14, 2020.
Khongorzul et al., Antibody-Drug Conjugates: A Comprehensive Review, Molecular Cancer Research, American Association for Cancer Research Journals, 18 pages, Oct. 28, 2019.

(Continued)

*Primary Examiner* — Sean McGarry
(74) *Attorney, Agent, or Firm* — Sunstein LLP

(57) ABSTRACT

Therapeutic compounds for red blood cell-mediated delivery of an active pharmaceutical ingredient to a target cell are described. The therapeutic compounds are configured to bind CD47 on the surface of a red blood cell and to be subsequently transferred to CD47 on the surface of the target cell, the therapeutic compound ultimately being internalized by the target cell via endocytosis. The target cell may be a fibrotic cell.

8 Claims, 8 Drawing Sheets

Specification includes a Sequence Listing.

(56) References Cited

OTHER PUBLICATIONS

Tan et al., MicroRNAs and cancer: Key paradigms in molecular therapy (Review), Oncology Letters, vol. 15, pp. 2735-2742, 2018.
Gupta et al., "Therapeutic modulation of the CD47-SIRPα axis in the pediatric tumor microenvironment: working up an appetite", Cancer Drug Resist, vol. 3, pp. 550-562, 2020.
Wernig et al., "Unifying mechanism for different fibrotic diseases", PNAS, vol. 14, No. 18, pp. 4757-4762, May 2, 2017.
Cui et al., "Activation of JUN in fibroblasts promotes pro-fibrotic programme and modulates protective immunity", Nature Communications, vol. 11, 2795, 14 pages, 2020.
Wang et al., "Intravenous delivery of siRNA targeting CD47 effectively inhibits melanoma tumor growth and lung metastasis", Molecular Therapy, vol. 21, No. 10, pp. 1919-1929, Oct. 2013.

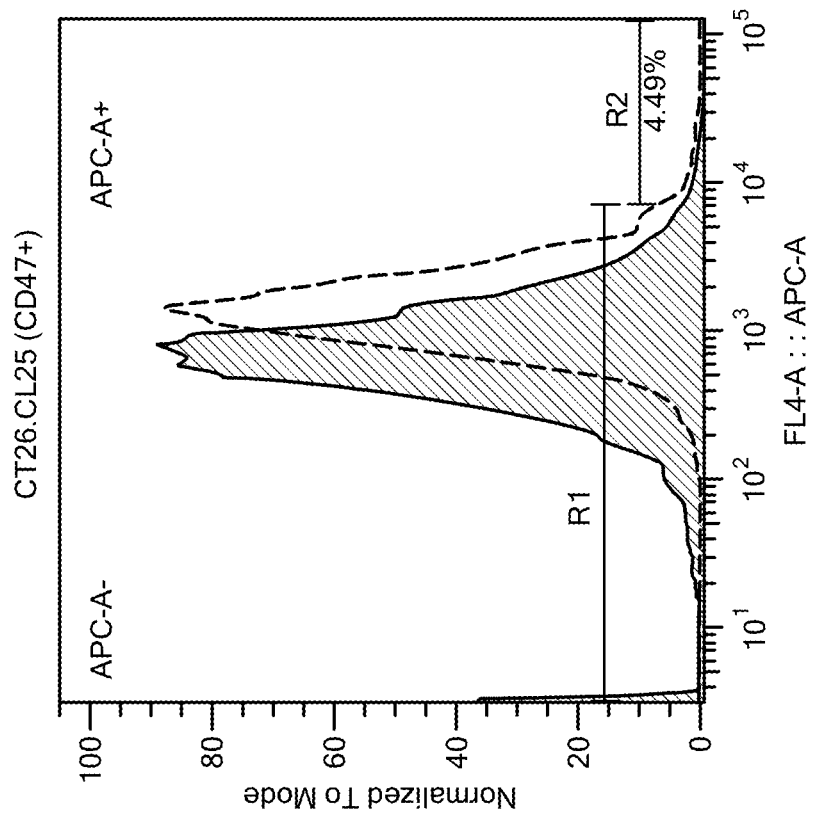
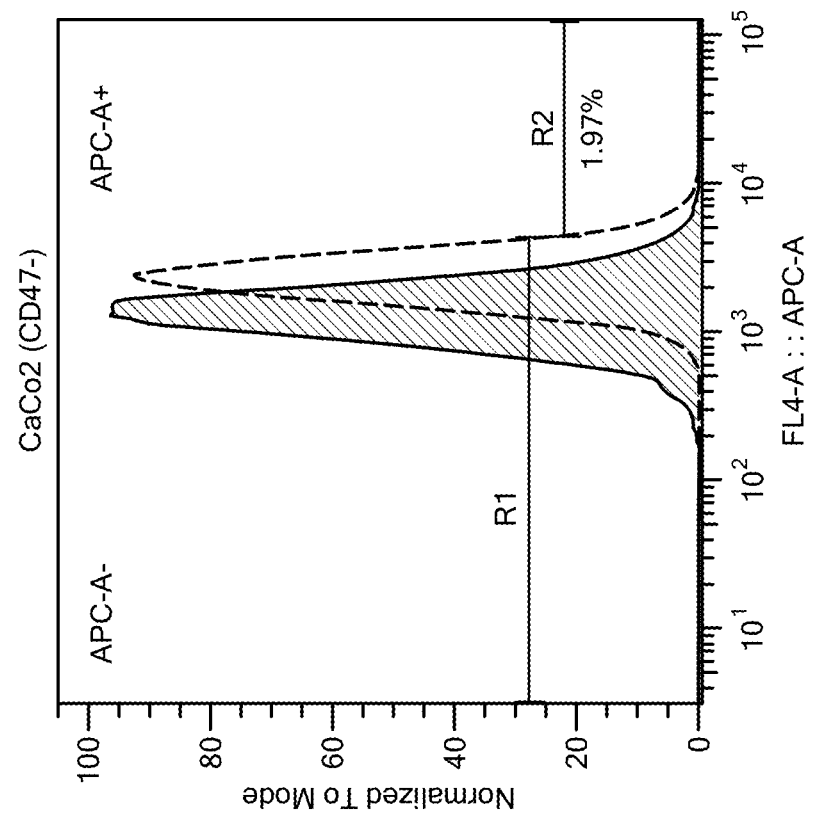
Fig. 3B
Fig. 3A

THERAPEUTIC COMPOUNDS FOR RED BLOOD CELL-MEDIATED DELIVERY OF AN ACTIVE PHARMACEUTICAL INGREDIENT TO A TARGET CELL

CROSS-REFERENCE TO RELATED APPLICATIONS

This application is a continuation of U.S. patent application Ser. No. 18/057,050 filed Nov. 18, 2022, which claims priority from U.S. Provisional Application No. 63/281,370, filed Nov. 19, 2021, and U.S. Provisional Application No. 63/392,323, filed Jul. 26, 2022, each of which is incorporated herein by reference in its entirety.

SEQUENCE LISTING

This application contains a Sequence Listing which has been submitted electronically in XML file format and is hereby incorporated by reference in its entirety. Said XML copy, created on Nov. 17, 2022, is named 4813_1004_SL.xml and is 4,562,889 bytes in size.

TECHNICAL FIELD

The present invention relates generally to a therapeutic compound configured to bind CD47, and more particularly to such a compound configured to bind CD47 on the surface of a red blood cell and to be subsequently transferred to CD47 on the surface of a target cell, the therapeutic compound ultimately being internalized by the target cell via endocytosis.

BACKGROUND ART

Cluster of differentiation 47 ("CD47"), an integrin-associated protein, is a multi-spanning plasma membrane protein involved in the processes inhibiting clearance by phagocytes or neutrophil motility. Signal-regulatory protein alpha ("SIRPα"), a transmembrane protein expressed by innate immune cells such as macrophages and dendritic cells, is the main receptor of CD47. The binding of SIRPα to CD47 triggers SIRPα inhibitory signals, which act as "don't eat me" signals to recipient macrophages, preventing their phagocytic activation. Thus, the SIRPα-CD47 interaction functions as a negative checkpoint for innate and subsequent adaptive immunity. Other proteins, such as signal regulatory protein gamma ("SIRPγ") and thrombospondin-1 ("TSP-1") can also bind CD47, thereby inhibiting aspects of immune response.

Mammalian cells typically express low levels of CD47 to protect them from phagocytosis. However, cancer cells overexpress CD47 as an evasion mechanism to escape immune surveillance and attack by phagocytic cells. Several human solid tumors overexpress CD47, i.e., the cells of these solid tumors express more CD47 than normal cells on average (Willingham et al. *PNAS* 109(17):6662-6667 (2012), which is hereby incorporated by reference in its entirety). CD47 has thus emerged as a promising new therapeutic target for cancer immunotherapy (Willingham et al. *PNAS* 109(17):6662-6667 (2012); Weiskopf, *Eur. J. Cancer* 76:100-109 (2017); Weiskopf et al. *J Clin Invest* 126(7):2610-2620 (2016), each of which is hereby incorporated by reference herein in its entirety).

In addition, virus-infected cells also express high levels of CD47. These virus-infected cells include cells infected with SARS-CoV-2, the virus that causes COVID-19 (Cham et al. *Cell Rep* 14; 31(2):107494 (2020) doi:10.1016/j.celrep.2020.03.058 and McLaughlin et al. *bioRxiv* 2021.03.01.433404 (2021) doi:10.1101/2021.03.01.433404, each of which is hereby incorporated by reference herein in its entirety). Blockade of CD47 inhibitory signaling has been demonstrated to enhance innate and adaptive immune responses to viral infection.

Moreover, increased CD47 expression has been observed in fibrotic fibroblasts and blocking CD47 reverses fibrosis by increasing phagocytosis of profibrotic fibroblasts and by eliminating suppressive effects on adaptive immunity (Cui et al. *Nat Commun* 11:2795 (2020); Wernig et al. *PNAS* 2017; 114(18):4757-62; Boyd *J Cyst Fibros Suppl* 1:S54-S59 (2020); Lerbs et al. *JCI Insight* 2020; 5(16):e140458 (2020), each of which is hereby incorporated by reference herein in its entirety).

CD47, therefore, offers a promising target for the treatment of cancers, viral infections, as well as fibrotic diseases, such as cystic fibrosis.

SUMMARY OF THE EMBODIMENTS

In accordance with one embodiment of the invention, a therapeutic compound for RBC-mediated delivery in a mammalian subject to a target cell expressing CD47, the therapeutic compound comprising: a CD47-binding protein conjugated to an active pharmaceutical ingredient ("API") so as to form a conjugate; wherein the CD47-binding protein is selected from the group consisting of wild type SIRPα (SEQ ID NO: 1), vSIRPα (SEQ ID NO: 3), wild type thrombospondin-1 (TSP-1) (SEQ ID NO: 7), wild type SIRPγ (SEQ ID NO: 4), vSIRPγ-1 (SEQ ID NO: 5), vSIRPγ-2 (SEQ ID NO: 6), ALX148 (SEQ ID NO: 962), TTI-661 (SEQ ID NO: 963), TTI-662 (SEQ ID NO: 964), a homolog of any of the foregoing, and combinations thereof, and is configured to bind the conjugate to CD47 of a red blood cell of the subject so as to enable transport of the conjugate, through the subject's circulatory system, to the target cell, so that (i) the CD47-binding protein, being configured to bind the conjugate to the CD47 of the red blood cell, binds the CD47 of the target cell, thus transferring the conjugate from the red blood cell to the target cell so as to form a conjugate-CD47 complex on the target cell, thereby blocking CD47 and inhibiting CD47 activity as an immune escape mechanism of the target cell, and (ii) the conjugate is taken up by the target cell via endocytosis of the conjugate-CD47 complex, thereby further inhibiting the immune escape mechanism of the target cell and delivering the API into the target cell. The mammalian subject may be a human.

In accordance with another embodiment of the invention, a therapeutic compound for RBC-mediated delivery in a mammalian subject to a target cell expressing CD47, the therapeutic compound comprising: a CD47-binding protein conjugated to an API so as to form a conjugate; wherein the CD47-binding protein is selected from the group consisting of wild type thrombospondin-1 (TSP-1) (SEQ ID NO: 7), wild type SIRPγ (SEQ ID NO: 4), vSIRPγ-1 (SEQ ID NO: 5), vSIRPγ-2 (SEQ ID NO: 6), ALX148 (SEQ ID NO: 962), TTI-661 (SEQ ID NO: 963), TTI-662 (SEQ ID NO: 964), a homolog of any of the foregoing, and combinations thereof, and is configured to bind the conjugate to CD47 of a red blood cell of the subject so as to enable transport of the conjugate, through the subject's circulatory system, to the target cell, so that (i) the CD47-binding protein, being configured to bind the conjugate to the CD47 of the red blood cell, binds the CD47 of the target cell, thus transferring the conjugate from the red blood cell to the target cell so as to form a conjugate-CD47 complex on the target cell, thereby blocking CD47 and inhibiting CD47 activity as an immune escape mechanism of the target cell, and (ii) the conjugate is taken up by the target cell via endocytosis of the conjugate-CD47 complex, thereby further inhibiting the immune escape mechanism of the target cell and delivering the API into the target cell. The mammalian subject may be a human.

In accordance with an embodiment of the invention, a therapeutic compound for RBC-mediated delivery in a mammalian subject to a target cell expressing CD47, the therapeutic compound comprising: a CD47-binding protein conjugated to an API so as to form a conjugate; wherein the CD47-binding protein is an anti-CD47 antibody, the anti-CD47 antibody comprising: (a) a heavy chain variable region including complementarity determining regions CDR1, CDR2, and CDR3 comprising SEQ ID NO: 932, SEQ ID NO: 933, and SEQ ID NO: 934, respectively, and a light chain variable region including complementarity determining regions CDR1, CDR2, and CDR3 comprising SEQ ID NO: 935, SEQ ID NO: 936, and SEQ ID NO: 937, respectively; (b) a heavy chain variable region including complementarity determining regions CDR1, CDR2, and CDR3 comprising SEQ ID NO: 940, SEQ ID NO: 941, and SEQ ID NO: 942, respectively, and a light chain variable region including complementarity determining regions CDR1, CDR2, and CDR3 comprising SEQ ID NO: 943, SEQ ID NO: 944, and SEQ ID NO: 945, respectively; (c) a heavy chain variable region including complementarity determining regions CDR1, CDR2, and CDR3 comprising SEQ ID NO: 948, SEQ ID NO: 949, and SEQ ID NO: 950, respectively, and a light chain variable region including complementarity determining regions CDR1, CDR2, and CDR3 comprising SEQ ID NO: 951, SEQ ID NO: 952, and SEQ ID NO: 953, respectively; or (d) a heavy chain variable region including complementarity determining regions CDR1, CDR2, and CDR3 comprising SEQ ID NO: 956, SEQ ID NO: 957, and SEQ ID NO: 958, respectively, and a light chain variable region including complementarity determining regions CDR1, CDR2, and CDR3 comprising SEQ ID NO: 959, SEQ ID NO: 960, and SEQ ID NO: 961, respectively; and being configured to bind the conjugate to CD47 of a red blood cell of the subject so as to enable transport of the conjugate, through the subject's circulatory system, to the target cell, so that (i) the CD47-binding protein, being configured to bind the conjugate to the CD47 of the red blood cell, binds the CD47 of the target cell, thus transferring the conjugate from the red blood cell to the target cell so as to form a conjugate-CD47 complex on the target cell, thereby blocking CD47 and inhibiting CD47 activity as an immune escape mechanism of the target cell, and (ii) the conjugate is taken up by the target cell via endocytosis of the conjugate-CD47 complex, thereby further inhibiting the immune escape mechanism of the target cell and delivering the API into the target cell. The mammalian subject may be a human.

The CD47-binding protein may be conjugated to the API by a bond selected from the group consisting of a covalent bond, a hydrogen bond, an ionic bond, a van der Waals interaction, and combinations thereof. The CD47-binding protein may be conjugated to the API by a linker and the linker may be cleavable. The linker may be configured to be cleaved by a lysosomal degradative enzyme.

In some embodiments, the API is selected from the group consisting of RNA, DNA, an RNA derivative, a DNA derivative, a protein, and a small molecule. The RNA may be selected from the group consisting of siRNA, shRNA, miRNA, antimiR, and mRNA.

The target cell may be a cell selected from the group consisting of a cancer cell, a virus infected cell, a fibrotic cell, and combinations thereof. In some embodiments, the target cell is a cancer cell. In some embodiments, the target cell is a virus-infected cell. In some embodiments, the target cell is a fibrotic cell.

In some embodiments, the cancer cell is in a tumor attributable to a cancer selected from the group consisting of brain tumor, spinal cord tumor, retinoblastoma, oral cancer, nasal cavity cancer, paranasal sinus cancer, pharyngeal cancer, laryngeal cancer, neck cancer, head and neck cancer, melanoma, skin cancer, breast cancer, thyroid cancer, malignant adrenal tumor, endocrine cancer, lung cancer, pleural tumor, respiratory tract cancer, esophageal cancer, stomach cancer, small intestine cancer, colon cancer, anal cancer, liver cancer, biliary tract cancer, pancreatic cancer, kidney cancer, bladder cancer, prostate cancer, testicular cancer, penile cancer, cervical cancer, endometrial cancer, choriocarcinoma, ovarian cancer, blood cancer including acute/chronic leukemia, malignant lymphoma and multiple myeloma, bone tumor, soft tissue tumor, childhood leukemia, and childhood cancer.

In some embodiments, the cancer cell is attributable to a cancer selected from the group consisting of ovarian serous cystadenocarcinoma, lung adenocarcinoma, cervical and endocervical cancer, head and neck squamous cell carcinoma, thyroid carcinoma, uterine corpus endometrioid carcinoma, prostate adenocarcinoma, mesothelioma, diffuse large B-cell lymphoma, acute leukemia, lung squamous cell carcinoma, acute lymphoblastic leukemia, esophageal carcinoma, myxofibrosarcoma, pancreatic adenocarcinoma, rectum adenocarcinoma, colon adenocarcinoma, acute megakaryoblastic leukemia, breast invasive carcinoma, stomach adenocarcinoma, bladder urothelial carcinoma, cholangiocarcinoma, leukemia, thymic carcinoma, leiomyosarcoma, thymoma, undifferentiated pleomorphic sarcoma, uterine carcinosarcoma, acute myeloid leukemia, glioblastoma multiforme, sarcoma, skin cutaneous melanoma, kidney clear cell carcinoma, dedifferentiated liposarcoma, lymphoma, retinoblastoma, neuroblastoma, osteosarcoma, juvenile myelomonocytic leukemia, gastrointestinal stromal tumor, dysembryoplatic neuroepithelial tumor, adrenocortical cancer, acute leukemia of ambiguous lineage, pheochromocytoma and paraganglioma, glioma, testicular germ cell tumor, supratentorial embryonal tumor NOS, neurofibroma, kidney papillary cell carcinoma, hepatocellular carcinoma, kidney chromophobe, malignant peripheral nerve sheath tumor, ependymoma, adrenocortical carcinoma, nasopharyngeal carcinoma, spindle cells/sclerosing rhabdomyosarcoma, melanoma, choroid plexus carcinoma, undifferentiated spindle cell carcinoma, myoepithelial carcinoma, alveolar rhabdomyosarcoma, rhabdomyosarcoma, atypical teratoid/rhabdoid tumor, desmoplastic small round cell tumor, fibromatosis, synovial sarcoma, wilms tumor, myofibromytosis, fibrolamellar hepatocellular carcinoma, undifferentiated sarcoma NOS, embryonal rhabdomyosarcoma, uveal melanoma, Ewing sarcoma, hepatoblastoma, infantile fibrosarcoma, INI-deficient soft tissue sarcoma NOA, undifferentiated hepatic sarcoma, and medulloblastoma.

In some embodiments, the virus-infected cell is infected with a SARS-CoV-2 virus. In some embodiments, the fibrotic cell is associated with cystic fibrosis.

In some embodiments, the API is siRNA, the siRNA being a double-stranded RNA molecule including an antisense RNA strand and a sense RNA strand, wherein: (a) the antisense RNA strand is 19-29 nucleotides in length and is complementary to contiguous nucleotides in a target mammalian mRNA sequence, the mRNA sequence being selected from the group consisting of SEQ ID NO: 8-747 and 771-824, (b) the sense RNA strand is 19-29 nucleotides in length and is complementary to 14-29 nucleotides from the antisense RNA strand, and (c) the double stranded RNA molecule has a double stranded region of 14-29 nucleotides in length and a 3' overhang region of 0-5 nucleotides in length. In other embodiments, the mRNA sequence is selected from the group consisting of SEQ ID NO: 22-747 and 771-824. In some embodiments, the mRNA sequence is selected from the group consisting of SEQ ID NO: 22-37. In other embodiments, the mRNA sequence is selected from the group consisting of SEQ ID NO: 38-39. In some embodiments, the mRNA sequence is selected from the group consisting of SEQ ID NO: 40-43. In other embodiments, the mRNA sequence is selected from the group consisting of SEQ ID NO: 44-51.

In some embodiments, the API is siRNA, the siRNA being a double-stranded RNA molecule including an antisense RNA strand and a sense RNA strand, wherein: (a) the antisense RNA strand is 19-29 nucleotides in length and is complementary to contiguous nucleotides in a target mammalian mRNA sequence, the mRNA sequence being selected from the group consisting of SEQ ID NO: 8-21, 482-486, and 748-765, (b) the sense RNA strand is 19-29 nucleotides in length and is complementary to 14-29 nucleotides from the antisense RNA strand, and (c) the double stranded RNA molecule has a double stranded region of 14-29 nucleotides in length and a 3' overhang region of 0-5 nucleotides in length. In other embodiments, the mRNA sequence is selected from the group consisting of SEQ ID NO: 482-486 and 748-765.

In some embodiments, the API is siRNA, the siRNA being a double-stranded RNA molecule including an antisense RNA strand and a sense RNA strand, wherein: (a) the antisense RNA strand is 19-29 nucleotides in length and is complementary to contiguous nucleotides in a target mammalian mRNA sequence, the mRNA sequence being selected from the group consisting of SEQ ID NO: 8-21, 40-43, and 766-770, (b) the sense RNA strand is 19-29 nucleotides in length and is complementary to 14-29 nucleotides from the antisense RNA strand, and (c) the double stranded RNA molecule has a double stranded region of 14-29 nucleotides in length and a 3' overhang region of 0-5 nucleotides in length. In other embodiments, the mRNA sequence is selected from the group consisting of SEQ ID NO: 40-43 and 766-770.

The API is shRNA, the shRNA being a single-stranded RNA molecule of 44-71 nucleotides in length, and having, in a 5' to 3' direction: a first region of 19-29 nucleotides at the 5' end of the single-stranded RNA molecule, the first region having a first sequence; a second region of 4-11 nucleotides directly adjacent to the first region, the second region having a second sequence; a third region of 19-29 nucleotides directly adjacent to the second region, the third region having a third sequence; and a fourth region of 2 nucleotides at the 3' end of the single-stranded RNA molecule, directly adjacent to the third region, the fourth region having a fourth sequence, wherein: (a) the first region has the same number of nucleotides as the third region, (b) the third sequence is the reverse-complement of the first sequence, (c) the third region is complementary to contiguous nucleotides in a target mammalian mRNA sequence, the mRNA sequence being selected from the group consisting of SEQ ID NO: 8-747 and 771-824, and (d) the single-stranded RNA molecule is configured to form a stem loop structure, the first region base pairing with the third region to form a stem, the second region forming a loop, and the fourth region forming a 3' overhang. In other embodiments, the mRNA sequence is selected from the group consisting of SEQ ID NO: 22-747 and 771-824. In some embodiments, the mRNA sequence is selected from the group consisting of SEQ ID NO: 22-37. In other embodiments, the mRNA sequence is selected from the group consisting of SEQ ID NO: 38-39. In some embodiments, the mRNA sequence is selected from the group consisting of SEQ ID NO: 40-43. In other embodiments, the mRNA sequence is selected from the group consisting of SEQ ID NO: 44-51.

In some embodiments, the API is shRNA, the shRNA being a single-stranded RNA molecule of 44-71 nucleotides in length, and having, in a 5' to 3' direction: a first region of 19-29 nucleotides at the 5' end of the single-stranded RNA molecule, the first region having a first sequence; a second region of 4-11 nucleotides directly adjacent to the first region, the second region having a second sequence; a third region of 19-29 nucleotides directly adjacent to the second region, the third region having a third sequence; and a fourth region of 2 nucleotides at the 3' end of the single-stranded RNA molecule, directly adjacent to the third region, the fourth region having a fourth sequence, wherein: (a) the first region has the same number of nucleotides as the third region, (b) the third sequence is the reverse-complement of the first sequence, (c) the third region is complementary to contiguous nucleotides in a target mammalian mRNA sequence, the mRNA sequence being selected from the group consisting of SEQ ID NO: 8-21, 482-486, and 748-765, and (d) the single-stranded RNA molecule is configured to form a stem loop structure, the first region base pairing with the third region to form a stem, the second region forming a loop, and the fourth region forming a 3' overhang. In other embodiments, the mRNA sequence is selected from the group consisting of SEQ ID NO: 482-486 and 748-765.

In some embodiments, the API is shRNA, the shRNA being a single-stranded RNA molecule of 44-71 nucleotides in length, and having, in a 5' to 3' direction: a first region of 19-29 nucleotides at the 5' end of the single-stranded RNA molecule, the first region having a first sequence; a second region of 4-11 nucleotides directly adjacent to the first region, the second region having a second sequence; a third region of 19-29 nucleotides directly adjacent to the second region, the third region having a third sequence; and a fourth region of 2 nucleotides at the 3' end of the single-stranded RNA molecule, directly adjacent to the third region, the fourth region having a fourth sequence, wherein: (a) the first region has the same number of nucleotides as the third region, (b) the third sequence is the reverse-complement of the first sequence, (c) the third region is complementary to contiguous nucleotides in a target mammalian mRNA sequence, the mRNA sequence being selected from the group consisting of SEQ ID NO: 8-21, 40-43, and 766-770, and (d) the single-stranded RNA molecule is configured to form a stem loop structure, the first region base pairing with the third region to form a stem, the second region forming a loop, and the fourth region forming a 3' overhang. In other embodiments, the mRNA sequence is selected from the group consisting of SEQ ID NO: 40-43 and 766-770.

In some embodiments, the API is an miRNA selected from the group consisting of SEQ ID NO: 825-844, 849-851, 853, 855, 857, 864, 865, and 867-883.

In some embodiments, the API is an antimiR, the antimiR being a single-stranded nucleic acid molecule of 12-25 nucleotides in length, the antimiR having a sequence of 12-25 contiguous nucleotides that is complementary to contiguous nucleotides in a target mature miRNA product sequence, the mature miRNA product sequence being selected from the group consisting of SEQ ID NO: 884-908, wherein the contiguous nucleotides in the mature miRNA product sequence includes, in a 5' to 3' direction, nucleotides 2 to 8 of the mature miRNA product sequence.

In some embodiments, the API is a small molecule selected from the group consisting of methotrexate; doxorubicin; vinca alkaloids; camptothecin analogues; microtubule-disrupting agents such as auristatins (e.g., MMAE and MMAF) and maytansinoids (e.g., DM1 and DM4); and DNA-damaging agents such as DNA topoisomerase I inhibitors (e.g., SN-38 and exatecan), double-strand break agents (e.g., calicheamicin), cross-linkers (e.g., pyrrolobenzodiazepine dimer-PBD), and alkylators (e.g., duocarmycin and indolinobenzodiazepine dimer-IGN).

In some embodiments, the API is a protein, the protein having an amino acid sequence selected from the group consisting of SEQ ID NO: 909-929 and homologs thereof. In other embodiments, the protein consists of an amino acid sequence selected from the group consisting of SEQ ID NO: 909-929 and homologs thereof.

In some embodiments, the API is an mRNA encoding an amino acid sequence selected from the group consisting of SEQ ID NO: 909-929 and homologs thereof, the mRNA being configured to be translated in the target cell to produce a protein comprising the amino acid sequence. In other embodiments, the mRNA is configured to be translated in the target cell to produce a protein consisting of the amino acid sequence. In some embodiments, the mRNA is codon optimized.

In accordance with one embodiment of the invention, a method of treating cancer in a mammalian subject in need thereof, the method comprising administering a therapeutically effective amount of a therapeutic compound described herein. The mammalian subject may be a human.

In accordance with another embodiment of the invention, a method of treating viral infection in a mammalian subject in need thereof, the method comprising administering a therapeutically effective amount of a therapeutic compound described herein. The mammalian subject may be a human.

In accordance with an embodiment of the invention, a method of treating fibrotic disease in a mammalian subject in need thereof, the method comprising administering a therapeutically effective amount of a therapeutic compound described herein. The mammalian subject may be a human.

In accordance with another embodiment of the invention, a pharmaceutical composition comprising a therapeutic compound described herein.

BRIEF DESCRIPTION OF THE DRAWINGS

The foregoing features of embodiments will be more readily understood by reference to the following detailed description, taken with reference to the accompanying drawings, in which:

Figures 1A, 1B:
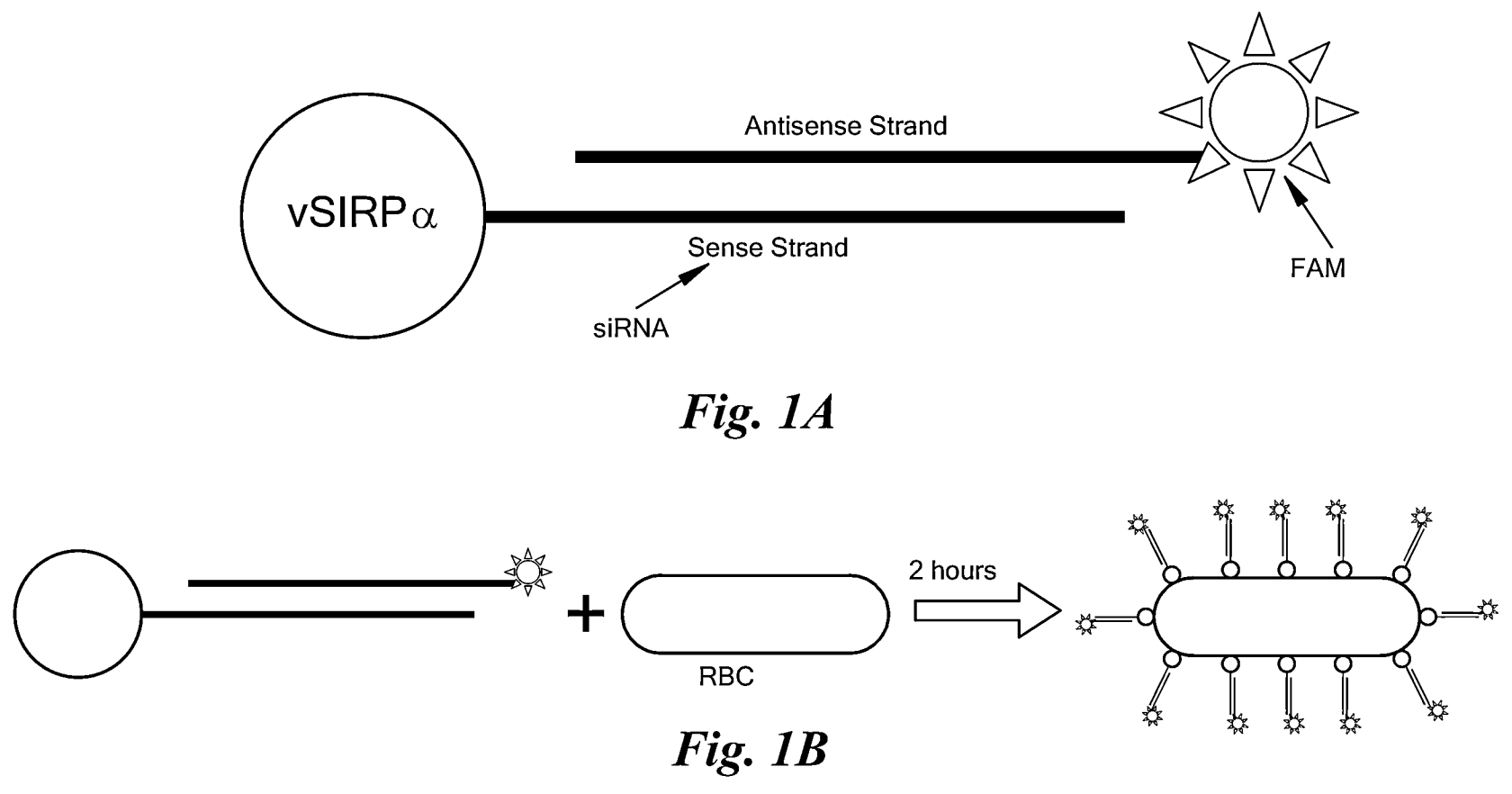

FIG. 1A illustrates a FAM-tagged vSIRPα-siRNA conjugate in accordance with embodiments of the invention. FIG. 1B is an illustration of the incubation of red blood cells with the FAM-tagged vSIRPα-siRNA conjugate of FIG. 1A.

FIG. 3A shows flow cytometry results of CaCO2 cells before and after being incubated with red blood cells bound with an Alexa Fluor® 647 anti-mouse CD47 monoclonal antibody, in accordance with embodiments of the invention. FIG. 3B shows flow cytometry results of CT26.CL25 cells before and after being incubated with red blood cells bound with an Alexa Fluor® 647 anti-mouse CD47 monoclonal antibody.

DETAILED DESCRIPTION OF SPECIFIC EMBODIMENTS

Figure 1C:
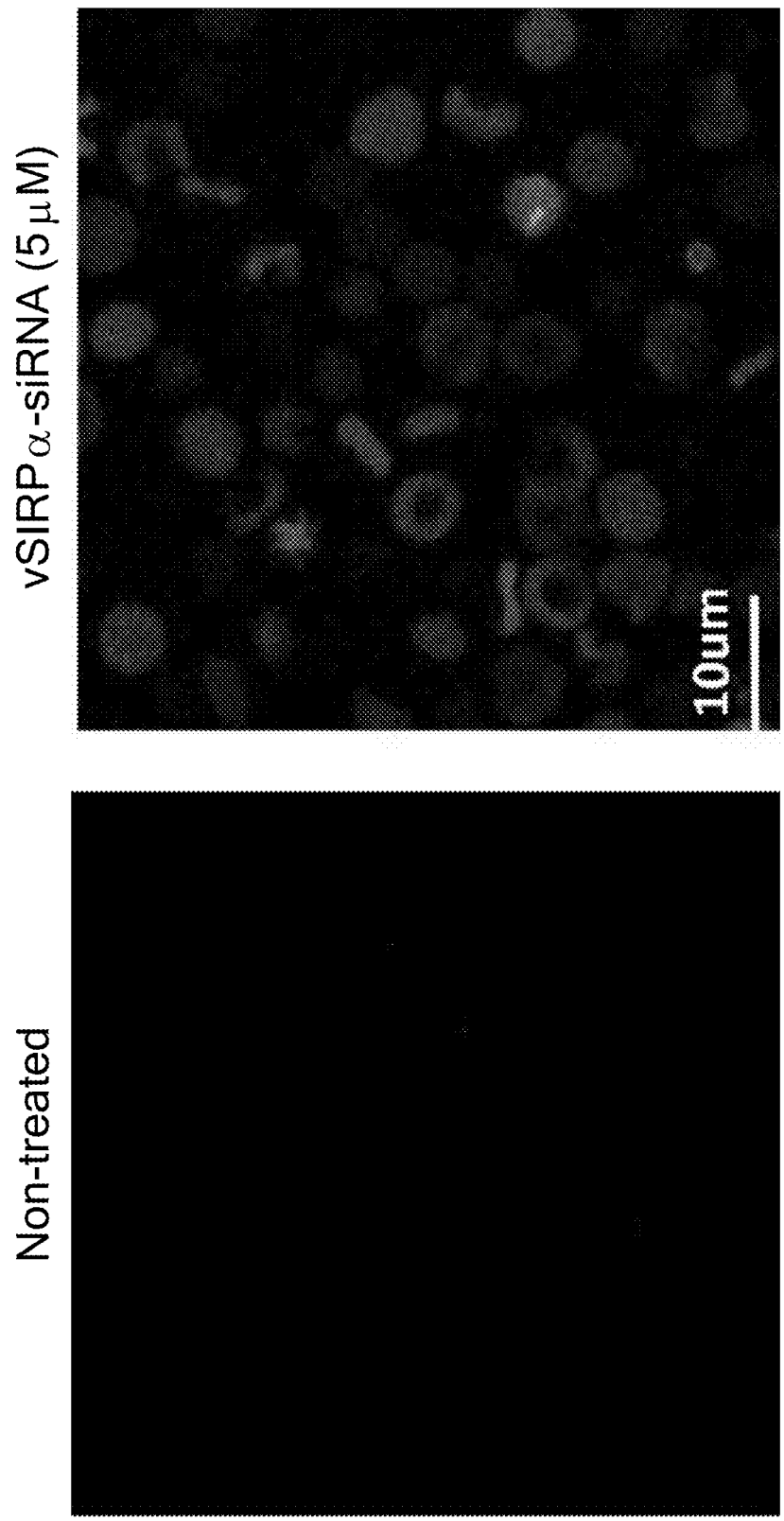
FIG. 1C shows fluorescence microscopy images of red blood cells that were not incubated with the FAM-tagged vSIRPα-siRNA conjugate shown in FIG. 1A (left) and red blood cells that were incubated with the FAM-tagged vSIRPα-siRNA conjugate shown in FIG. 1A (right).

As used in this description and the accompanying claims, the following terms shall have the meanings indicated, unless the context otherwise requires:

The terms "a" and "an" and "the" and similar reference used in the context of describing the invention (especially in the context of the claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. No language in the specification should be construed as indicating any non-claimed element essential to the practice of the invention A "set" includes at least one member.

The term "mammal," and the like, refers to any animal species of the Mammalian class. Examples of mammals include humans; laboratory animals such as rats, mice, simians and guinea pigs; domestic animals such as rabbits, cattle, sheep, goats, cats, dogs, horses, pigs, and the like.

"Active pharmaceutical ingredient," "API," and the like, means the non-CD47-binding protein portion and the non-linker portion of a therapeutic compound, in accordance with embodiments of the invention, that is biologically active. Suitable active pharmaceutical ingredients ("APIs") include RNA (siRNA, miRNA, shRNA, and mRNA), DNA, antimiR oligonucleotides (RNA, DNA, and derivatives thereof), RNA and DNA derivatives (including, but not limited to, modified RNA and DNA comprising a modified backbone, sugar, and/or base), proteins, and small molecules.

As used herein, a "homolog" of a given protein, and the like, shall mean a protein having at least 95% sequence identity with the given protein.

"Complementarity," as used herein regarding nucleic acid sequences, refers to the ability of a nucleic acid to forms hydrogen bonds with another nucleic acid sequence by Watson-Crick base pairing or wobble base pairing. A percent complementarity indicates the percentage of nucleotides in a nucleic acid molecule that can form hydrogen bonds (e.g., Watson-Crick base pairing) with the nucleotides of a second nucleic acid sequence (e.g., 5, 6, 7, 8, 9, 10 out of 10 being 50%, 60%, 70%, 80%, 90%, and 100% complementarity). "Perfectly complementary," and the like, means that all the contiguous nucleotides of a nucleic acid sequence will hydrogen bond with the same number of contiguous nucleotides in a second nucleic acid sequence (i.e., the nucleic acid sequence has 100% complementarity). "Complementary," as used herein without further qualification, means that contiguous nucleotides of a nucleic acid sequence has a percent complementarity with contiguous nucleotides of a second nucleic acid sequence that is selected from the group consisting of 95%, 96%, 97%, 98%, 99%, and 100% complementarity over a region of 12, 13, 14, 15, 16, 17, 18, 19, 20, 21, 22, 23, 24, 25, 26, 27, 28, 29, or more nucleotides of the nucleic acid sequence. For example, a nucleic acid sequence that is 19 nucleotides in length and complementary to 14 nucleotides of a second nucleic acid sequence means that 14 contiguous nucleotides of the nucleic acid sequence has a percent complementarity with contiguous nucleotides of the second nucleic acid sequence that is selected from the group consisting of 95%, 96%, 97%, 98%, 99%, and 100% complementarity. A nucleic acid sequence that is 19 nucleotides in length and complementary to contiguous nucleotides in a second nucleic acid sequence means that 19 contiguous nucleotides of the nucleic acid sequence has a percent complementarity with contiguous nucleotides of the second nucleic acid sequence that is selected from the group consisting of 95%, 96%, 97%, 98%, 99%, and 100% complementarity.

"Codon-optimized" means that the coding sequence of an mRNA transcript contains the most or second most preferred codon, for the species of a given target cell/host cell, for at least 60% of the codons of the coding sequence such that the codon-optimized sequence is more efficiently translated in the target cell/host cell relative to a non-optimized sequence.

The term "antibody" refers to an immunoglobulin molecule that is typically composed of two identical pairs of polypeptide chains, each pair having one "heavy" (H) chain and one "light" (L) chain. Human light chains are classified as kappa (κ) and lambda (λ). Heavy chains are classified as mu, delta, gamma, alpha, or epsilon, and define the antibody's isotype as IgM, IgD, IgG, IgA, and IgE, respectively. Each heavy chain is comprised of a heavy chain variable region (VH) and a heavy chain constant region. The heavy chain constant regions of IgD, IgG, and IgA are comprised of three domains, CH1, CH2 and CH3, and the heavy chain constant regions of IgM and IgE are comprised of four domains, CH1, CH2, CH3, and CH4. Each light chain is comprised of a light chain variable region (VL) and a light chain constant region. The light chain constant region is comprised of one domain, CL. The constant regions of the antibodies may mediate the binding of the immunoglobulin to host tissues or factors, including various cells of the immune system (e.g., effector cells). The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from the amino-terminus to carboxy-terminus in the following order: FR1, CDR1, FR2, CDR2, FR3, CDR3, FR4. The variable regions of each heavy/light chain pair (VH/VL) typically form an antibody's antigen-binding site. The term "antibody" is not limited by any particular method of producing the antibody. For example, it includes monoclonal antibodies, recombinant antibodies, and polyclonal antibodies.

The term "human antibody" refers to an antibody consisting of amino acid sequences of human immunoglobulin sequences only. A human antibody may contain murine carbohydrate chains if produced in a mouse, in a mouse cell or in a hybridoma derived from a mouse cell. Human antibodies may be prepared in a variety of ways known in the art.

The term "humanized antibody" refers to an antibody that contains some or all of the CDRs from a non-human animal antibody, while the framework and constant regions of the antibody contain amino acid residues derived from human antibody sequences. Humanized antibodies are typically produced by grafting CDRs from a mouse antibody into human framework sequences followed by back substitution of certain human framework residues for the corresponding mouse residues from the source antibody. The term "humanized antibody" also refers to an antibody of non-human origin in which, typically in one or more variable regions, one or more epitopes have been removed that have a high propensity of constituting a human T-cell and/or B-cell epitope, for purposes of reducing immunogenicity. The amino acid sequence of the epitope can be removed in full or in part. However, typically the amino acid sequence is altered by substituting one or more of the amino acids constituting the epitope for one or more other amino acids, thereby changing the amino acid sequence into a sequence that does not constitute a human T-cell and/or B-cell epitope. The amino acids are substituted by amino acids that are present at the corresponding position(s) in a corresponding human variable heavy or variable light chain as the case may be.

The term "pharmaceutically acceptable carrier" means solvents, carrier agents, diluting agents and the like which are usually used in the administration of pharmaceutical compounds.

CD47 is overexpressed in various cancer cells, in virus-infected cells, and in fibrotic cells, offering a promising target for the treatment of various cancers, viral infections, and fibrotic diseases. By blocking CD47 signaling in these cells, and even the expression of CD47 itself, these cells' evasion of the immune system can be suppressed, allowing for their elimination and the subsequent recovery of a patient from disease.

For example, intravenous injection of a variant SIRPα ("vSIRPα"), having high affinity for CD47 and conjugated to a probe, has been found to be taken up by tumorigenic cells of mice. In addition, vSIRPα, conjugated to a siRNA targeting CD47, has been shown to enhance phagocytosis of CT26.CL25 cancer cells in culture (Ko et al. *Control Release* 323:376-386 (2020) and U.S. Publication No. 2021/0015931, each of which is hereby incorporated by reference herein in its entirety).

We have unexpectedly found that CD47 present on the cell surface of red blood cells ("RBC") and on the cell surface of target cells, such as cancer cells, virus-infected cells, and fibrotic cells, can be utilized to deliver various APIs to said target cells via a novel mechanism.

Here, we describe novel therapeutic compounds for RBC-mediated delivery of an API to a target cell expressing CD47 in a mammalian subject. The therapeutic compound is a conjugate comprising a CD47-binding protein conjugated to an API. The CD47-binding protein of the conjugate binds the conjugate to CD47 present on the surface of the subject's red blood cells, thereby allowing transport of the conjugate through the subject's circulatory system to the target cell. The conjugate is transferred from the RBC to CD47 present on the surface of the target cell. Upon binding of the conjugate to CD47 of the target cell, the ability of the target cell to evade attack by the subject's immune system is reduced. Furthermore, upon binding of the conjugate to CD47 of the target cell, the conjugate-CD47 complex is internalized via endocytosis, further reducing the ability of the target cell to evade attack by the subject's immune system, and delivering the API into the target cell. Surprisingly, when the conjugate is bound to CD47 on the surface of the RBC, the conjugate-CD47 is not internalized by the RBC. In some embodiments, the mammalian subject is a human.

The CD47-binding protein may be conjugated to the API by a linker. A linker connects a CD47-binding protein to an API. The linker may be a cleavable linker that is cleaved upon internalization of conjugate by the target cell, thereby releasing the API from the CD47-binding protein In some embodiments, the target cell is a cancer cell and the therapeutic compound may be used to treat a cancer in a mammalian subject.

The cancer cell may be in a tumor attributable to a cancer selected from the group consisting of brain tumor, spinal cord tumor, retinoblastoma, oral cancer, nasal cavity cancer, paranasal sinus cancer, pharyngeal cancer, laryngeal cancer, neck cancer, head and neck cancer, melanoma, skin cancer, breast cancer, thyroid cancer, malignant adrenal tumor, endocrine cancer, lung cancer, pleural tumor, respiratory tract cancer, esophageal cancer, stomach cancer, small intestine cancer, colon cancer, anal cancer, liver cancer, biliary tract cancer, pancreatic cancer, kidney cancer, bladder cancer, prostate cancer, testicular cancer, penile cancer, cervical cancer, endometrial cancer, choriocarcinoma, ovarian cancer, blood cancer including acute/chronic leukemia, malignant lymphoma and multiple myeloma, bone tumor, soft tissue tumor, childhood leukemia, and childhood cancer.

The cancer cell may attributable to a cancer selected from the group consisting of ovarian serous cystadenocarcinoma, lung adenocarcinoma, cervical and endocervical cancer, head and neck squamous cell carcinoma, thyroid carcinoma, uterine corpus endometrioid carcinoma, prostate adenocarcinoma, mesothelioma, diffuse large B-cell lymphoma, acute leukemia, lung squamous cell carcinoma, acute lymphoblastic leukemia, esophageal carcinoma, myxofibrosarcoma, pancreatic adenocarcinoma, rectum adenocarcinoma, colon adenocarcinoma, acute megakaryoblastic leukemia, breast invasive carcinoma, stomach adenocarcinoma, bladder urothelial carcinoma, cholangiocarcinoma, leukemia, thymic carcinoma, leiomyosarcoma, thymoma, undifferentiated pleomorphic sarcoma, uterine carcinosarcoma, acute myeloid leukemia, glioblastoma multiforme, sarcoma, skin cutaneous melanoma, kidney clear cell carcinoma, dedifferentiated liposarcoma, lymphoma, retinoblastoma, neuroblastoma, osteosarcoma, juvenile myelomonocytic leukemia, gastrointestinal stromal tumor, dysembryoplatic neuroepithelial tumor, adrenocortical cancer, acute leukemia of ambiguous lineage, pheochromocytoma and paraganglioma, glioma, testicular germ cell tumor, supratentorial embryonal tumor NOS, neurofibroma, kidney papillary cell carcinoma, hepatocellular carcinoma, kidney chromophobe, malignant peripheral nerve sheath tumor, ependymoma, adrenocortical carcinoma, nasopharyngeal carcinoma, spindle cells/sclerosing rhabdomyosarcoma, melanoma, choroid plexus carcinoma, undifferentiated spindle cell carcinoma, myoepithelial carcinoma, alveolar rhabdomyosarcoma, rhabdomyosarcoma, atypical teratoid/rhabdoid tumor, desmoplastic small round cell tumor, fibromatosis, synovial sarcoma, wilms tumor, myofibromytosis, fibrolamellar hepatocellular carcinoma, undifferentiated sarcoma NOS, embryonal rhabdomyosarcoma, uveal melanoma, Ewing sarcoma, hepatoblastoma, infantile fibrosarcoma, INI-deficient soft tissue sarcoma NOA, undifferentiated hepatic sarcoma, and medulloblastoma. See Gupta et al. *Cancer Drug Resist* 3:550-62 (2020), which is hereby incorporated by reference herein in its entirety.

In other embodiments, the target cell is a virus-infected cell and the therapeutic compound may be used to treat a viral infection in a mammalian subject. The virus-infected cell may be infected with the SARS-CoV-2 virus.

In some embodiments, the target cell is a fibrotic cell and the therapeutic compound may be used to treat a fibrotic disease in a mammalian subject. The fibrotic cell may be a fibrotic fibroblast. In some embodiments, the fibrotic disease is cystic fibrosis.

CD47-Binding Proteins

Suitable CD47-binding proteins for the conjugates described herein include wild type ("wt") SIRPα (SEQ ID NO:1), variant SIRPα ("vSIRPα") (SEQ ID NO:3), wt TSP-1 (SEQ ID NO:7), wt SIRPγ (SEQ ID NO:4), variant SIRPγ-1 ("vSIRPγ-1") (SEQ ID NO:5), variant SIRPγ-2 ("vSIRPγ-2") (SEQ ID NO:6), and homologs of any of the foregoing. ALX148 (SEQ ID NO: 962), TTI-661 (SEQ ID NO: 963), TTI-662 (SEQ ID NO: 964), and homologs thereof are also suitable CD47-binding proteins for the conjugates described herein. ALX148 is a SIRPα D1 variant fused to an Fc domain monomer. See, e.g., U.S. Pat. No. 10,696,730, which is hereby incorporated by reference herein in its entirety. TTI-661 is an IgV domain of human SIRPα variant 2 fused to a constant region of human IgG1 antibody, and TTI-662 is an IgV domain of human SIRPα variant 2 fused to a constant region of human IgG4 antibody. See, e.g., U.S. Pat. No. 9,969,789, which is hereby incorporated by reference herein in its entirety.

Other suitable CD47-binding proteins include anti-CD47 antibodies.

In some embodiments, the CD47-binding protein is an anti-CD47 antibody, such as B6H12, 5F9, 8B6, C3, and Hu5F9-G4, described in U.S. Pat. Nos. 9,017,675 and 9,623,079, each of which is hereby incorporated by reference herein in its entirety.

In some embodiments, the anti-CD47 antibody includes a heavy chain variable region comprising SEQ ID NO: 930 and a light chain variable region comprising SEQ ID NO: 931. In some embodiments, the anti-CD47 antibody includes a heavy chain variable region comprising SEQ ID NO: 938 and a light chain variable region comprising SEQ ID NO: 939. In some embodiments, the anti-CD47 antibody includes a heavy chain variable region comprising SEQ ID NO: 946 and a light chain variable region comprising SEQ ID NO: 947. In some embodiments, the anti-CD47 antibody includes a heavy chain variable region comprising SEQ ID NO: 954 and a light chain variable region comprising SEQ ID NO: 955.

In some embodiments, the anti-CD47 antibody comprises a heavy chain variable region including complementarity determining regions CDR1, CDR2, and CDR3 comprising SEQ ID NO: 932, SEQ ID NO: 933, and SEQ ID NO: 934, respectively, and a light chain variable region including complementarity determining regions CDR1, CDR2, and CDR3 comprising SEQ ID NO: 935, SEQ ID NO: 936, and SEQ ID NO: 937, respectively.

In some embodiments, the anti-CD47 antibody comprises a heavy chain variable region including complementarity determining regions CDR1, CDR2, and CDR3 comprising SEQ ID NO: 940, SEQ ID NO: 941, and SEQ ID NO: 942, respectively, and a light chain variable region including complementarity determining regions CDR1, CDR2, and CDR3 comprising SEQ ID NO: 943, SEQ ID NO: 944, and SEQ ID NO: 945, respectively.

In some embodiments, the anti-CD47 antibody comprises a heavy chain variable region including complementarity determining regions CDR1, CDR2, and CDR3 comprising SEQ ID NO: 948, SEQ ID NO: 949, and SEQ ID NO: 950, respectively, and a light chain variable region including complementarity determining regions CDR1, CDR2, and CDR3 comprising SEQ ID NO: 951, SEQ ID NO: 952, and SEQ ID NO: 953, respectively.

In some embodiments, the anti-CD47 antibody comprises a heavy chain variable region including complementarity determining regions CDR1, CDR2, and CDR3 comprising SEQ ID NO: 956, SEQ ID NO: 957, and SEQ ID NO: 958, respectively, and a light chain variable region including complementarity determining regions CDR1, CDR2, and CDR3 comprising SEQ ID NO: 959, SEQ ID NO: 960, and SEQ ID NO: 961, respectively.

In some embodiments, the anti-CD47 antibody is a human antibody. In some embodiments, the anti-CD47 antibody is a humanized antibody.

Each of these CD47-binding proteins binds to CD47 present on the surface of a target cell.

In some embodiments, a CD47-binding protein is conjugated to an API by a bond selected from the group consisting of a covalent bond, a hydrogen bond, an ionic bond, a van der Waals interaction, and combinations thereof. Examples of linkers that covalently bond a CD47-binding protein to an API are described below.

Linkers

Suitable linkers include, but are not limited to, cleavable linkers such as hydrazone linkers, imine linkers, oxime linkers, carbonate linkers, acetal linkers, orthoester linkers, silyl ether linkers, disulfide linkers, trioxolane linkers, beta-glucuronide linkers, beta-galactoside linkers, pyrophosphate linkers, phosphoramidate linkers, arylsulfate linkers, heptamethine cyanine linkers, nitrobenzyl linkers, aryl boronic acid linkers, boronate linkers, thioether linkers, maleimidocaproyl-containing linkers, enzyme-cleavable peptide linkers, and para-amino benzyl carbamate-containing linkers, as well as non-cleavable linkers such as polyethylene glycol.

The CD47-binding protein-API conjugates described herein may be made by joining the CD47-binding protein to the API via a linker using coupling reactions such as bis(vinylsulfonyl)piperazine-disulfide coupling, N-methyl-N-phenylvinylsulfonamide-cysteine coupling, platinum (II) compound-histidine coupling, and tetrazine-trans-cyclooctene coupling. Suitable linkers and coupling reactions are known to those of skill in art. See, e.g., Su et al. *Acta Pharmaceutica Sinica B* (2021), ISSN 2211-3835; Pan et al. *Med Res Rev.* 40:2682-2713 (2020); Khongorzul et al. *Mol Cancer Res* 18:3-19 (2020); Bargh et al. *Chem Soc Rev* 48:4361-4374 (2019); and Smith et al. *Pharm Res* 32:3526-3540 (2015), each of which is hereby incorporated by reference herein in its entirety.

Various enzyme-cleavable peptide linkers, such as those described below, can be used to couple a CD47-binding protein to an API to form a CD47-binding protein-API conjugate, in accordance with embodiments of the invention. These linkers comprise amino acid residues and are cleaved by specific enzymes within a cell, such as lysosomal degradative enzymes. See, e.g., Kong et al. *J Biol Chem* 290:7160-7168 (2015); Poreba *FEBS J* 287:1936-1969 (2020); and Singh et al., *Current Medicinal Chemistry* 15(18) (2008), each of which is hereby incorporated by reference herein in its entirety. Exemplary peptide linkers suitable for use in accordance with embodiments of the invention are described below.

For example, di-peptide linkers are comprised of two amino acid residues that serve as a recognition motif for cleavage by the enzyme cathepsin B, which cleaves the amide bond after the second amino acid residue between the carbonyl and amine. Di-peptide linkers cleaved by cathepsin B include Phe-Arg, Phe-Cit, Phe-Lys, Ala-Arg, Ala-Cit, Val-Ala, Val-Arg, Val-Lys, Val-Cit, and Arg-Arg. Cathepsin B similarly recognizes and cleaves the tetra-peptide linkers Gly-Phe-Leu-Gly and Ala-Leu-Ala-Leu after the fourth amino acid residue.

In addition, the tri-peptide linker Ala-Ala-Asn is cleaved by the enzyme legumain after the last amino acid residue. The tetra-peptide linkers Lys-Ala-Gly-Gly, Leu-Arg-Gly-Gly, and Arg-Lys-Arg-Arg are cleaved by the papain-like protease enzyme.

Peptide linkers Arg-Arg-X, Ala-Leu-X, Gly-Leu-Phe-Gly-X, Gly-Phe-Leu-Gly-X, and Ala-Leu-Ala-Leu-X, where X is any amino acid, are cleaved by the enzymes cathepsin B, H, and L. Cathepsin B, H, and L are responsible for lysosomal degradation of proteins.

Peptide linkers Phe-Ala-Ala-Phe($NO_2$)-Phe-Val-Leu-OM4P-X and Bz-Arg-Gly-Phe-Phe-Pro-4mβNA, where X is any amino acid, are cleaved by the enzyme cathepsin D.

Serum plasminogen activator is produced in many tumor cells. Plasminogen is converted to plasmin, thus producing a high-level of plasmin in the tumor cells. This plasmin is degraded rapidly in the plasma and hence tissues remote to the tumor are not exposed to plasmin. Plasmin is responsible for the fibrinolysis and degradation of blood plasma proteins and cleaves the peptide linkers D-Val-Leu-Lys-X, D-Ala-Phe-Lys-X, and D-Ala-Trp-Lys-X, where X is any amino acid.

Tissue plasminogen activator (tPA) and urokinase (uPA) are responsible for activation of plasmin formation and can each cleave the peptide linker Gly-Gly-Gly-Arg-Arg-Arg-Val-X, where X is any amino acid.

Prostate-specific antigen is responsible for liquefaction of semen and cleaves the peptide linker morpholinocarbonyl-His-Ser-Ser-Lys-Leu-Gln-Leu-X, where X is any amino acid.

Matrix metalloproteases (MMP-2 and MM-9) are responsible for degradation of extracellular matrix and collagens and cleave the peptide linkers Ac-Pro-Leu-Gln-Leu-X and Gly-Pro-Leu-Gly-Ile-Ala-Gly-Gln-X, where X is any amino acid.

APIs

In accordance with some embodiments, the API may be a small molecule. For example, small molecule APIs useful in the treatment of cancer include, but are not limited to, methotrexate; doxorubicin; vinca alkaloids; camptothecin analogues; microtubule-disrupting agents such as auristatins (e.g., MMAE and MMAF) and maytansinoids (e.g., DM1 and DM4); and DNA-damaging agents such as DNA topoisomerase I inhibitors (e.g., SN-38 and exatecan), double-strand break agents (e.g., calicheamicin), cross-linkers (e.g., pyrrolobenzodiazepine dimer-PBD), and alkylators (e.g., duocarmycin and indolinobenzodiazepine dimer-IGN). See, e.g., Khongorzul et al. *Mol Cancer Res* 18:3-19 (2020); Salomon et al. *Mol Pharm* 16(12):4817-4825 (2019); and Drago et al. *Nat Rev Clin Oncol* 18, 327-344 (2021), each of which is hereby incorporated by reference herein in its entirety.

In accordance with other embodiments, the API may be small-interfering RNA ("siRNA"). siRNA is a double-stranded RNA molecule that can reduce the expression of a specific gene by causing the degradation of the gene's mRNA transcript(s), which shares partial complementarity with a strand of the double-stranded siRNA molecule. The process of reducing the expression of a gene using siRNA is referred to as RNA interference ("RNAi"). See U.S. Pat. Nos. 7,056,704, 7,078,196, 8,372,968 each of which is hereby incorporated by reference herein its entirety.

Several genes have been implicated in promoting cancer progression and cancer cell proliferation through various mechanisms. These genes, and their mRNA transcripts are listed in Table 1. By reducing the expression of one or more genes from Table 1, cancer progression and cancer cell proliferation may be inhibited. Thus, the transcripts of the genes listed in Table 1 represent key targets for the treatment of cancer using siRNA-mediated RNAi.

In some embodiments, an API useful for the treatment of cancer in a mammal is siRNA, the siRNA being a double-stranded RNA molecule including an antisense RNA strand and a sense RNA strand, wherein: (a) the antisense RNA strand is 19-29 nucleotides in length and is complementary to contiguous nucleotides in a target mammalian mRNA sequence, the mRNA sequence being selected from the group consisting of SEQ ID NO: 8-747 and 771-824, (b) the sense RNA strand is 19-29 nucleotides in length and is complementary to 14-29 nucleotides from the antisense RNA strand, and (c) the double stranded RNA molecule has a double stranded region of 14-29 nucleotides in length and a 3' overhang region of 0-5 nucleotides in length.

In some embodiments, an API useful for the treatment of cancer in a mammal is siRNA, the siRNA being a double-stranded RNA molecule including an antisense RNA strand and a sense RNA strand, wherein: (a) the antisense RNA strand is 19-29 nucleotides in length and is complementary to contiguous nucleotides in a target mammalian mRNA sequence, the mRNA sequence being selected from the group consisting of SEQ ID NO: 22-747 and 771-824, (b) the sense RNA strand is 19-29 nucleotides in length and is complementary to 14-29 nucleotides from the antisense RNA strand, and (c) the double stranded RNA molecule has a double stranded region of 14-29 nucleotides in length and a 3' overhang region of 0-5 nucleotides in length.

In some embodiments, an API useful for the treatment of cancer in a mammal is siRNA, the siRNA being a double-stranded RNA molecule including an antisense RNA strand and a sense RNA strand, wherein: (a) the antisense RNA strand is 19-29 nucleotides in length and is complementary to contiguous nucleotides in a target mammalian mRNA sequence, the mRNA sequence selected from the group consisting of SEQ ID NO: 22-37, (b) the sense RNA strand is 19-29 nucleotides in length and is complementary to 14-29 nucleotides from the antisense RNA strand, and (c) the double stranded RNA molecule has a double stranded region of 14-29 nucleotides in length and a 3' overhang region of 0-5 nucleotides in length.

In some embodiments, an API useful for the treatment of cancer in a mammal is siRNA, the siRNA being a double-stranded RNA molecule including an antisense RNA strand and a sense RNA strand, wherein: (a) the antisense RNA strand is 19-29 nucleotides in length and is complementary to contiguous nucleotides in a target mammalian mRNA sequence, the mRNA sequence selected from the group consisting of SEQ ID NO: 38-39, (b) the sense RNA strand is 19-29 nucleotides in length and is complementary to 14-29 nucleotides from the antisense RNA strand, and (c) the double stranded RNA molecule has a double stranded region of 14-29 nucleotides in length and a 3' overhang region of 0-5 nucleotides in length.

In some embodiments, an API useful for the treatment of cancer in a mammal is siRNA, the siRNA being a double-stranded RNA molecule including an antisense RNA strand and a sense RNA strand, wherein: (a) the antisense RNA strand is 19-29 nucleotides in length and is complementary to contiguous nucleotides in a target mammalian mRNA sequence, the mRNA sequence selected from the group consisting of SEQ ID NO: 40-43, (b) the sense RNA strand is 19-29 nucleotides in length and is complementary to 14-29 nucleotides from the antisense RNA strand, and (c) the double stranded RNA molecule has a double stranded region of 14-29 nucleotides in length and a 3' overhang region of 0-5 nucleotides in length.

In some embodiments, an API useful for the treatment of cancer in a mammal is siRNA, the siRNA being a double-stranded RNA molecule including an antisense RNA strand and a sense RNA strand, wherein: (a) the antisense RNA strand is 19-29 nucleotides in length and is complementary to contiguous nucleotides in a target mammalian mRNA sequence, the mRNA sequence selected from the group consisting of SEQ ID NO: 44-51, (b) the sense RNA strand is 19-29 nucleotides in length and is complementary to 14-29 nucleotides from the antisense RNA strand, and (c) the double stranded RNA molecule has a double stranded region of 14-29 nucleotides in length and a 3' overhang region of 0-5 nucleotides in length.

TABLE 1 siRNA and shRNA Cancer (Cancer Cell) Target Transcripts

| Gene | GenBank Gene ID | GenBank cDNA RefSeq Accession | (mRNA) SEQ ID NO |
|---|---|---|---|
| CD47 | 961 | NM_001777.4 | 8 |
| | | NM_198793.3 | 9 |
| | | NM_001382306.1 | 10 |
| | | XM_005247909.2 | 11 |
| | | XM_017007536.1 | 12 |
| | | XR_241521.2 | 13 |
| | | XR_241522.2 | 14 |
| | | XR_924218.2 | 15 |
| | | XR_924219.2 | 16 |
| | | XR_924220.2 | 17 |
| | | XR_001740374.2 | 18 |
| | | XR_001740375.2 | 19 |
| | | XR_002959610.1 | 20 |
| | | XR_002959611.1 | 21 |

TABLE 1-continued siRNA and shRNA Cancer (Cancer Cell) Target Transcripts

| Gene | GenBank Gene ID | GenBank cDNA RefSeq Accession | (mRNA) SEQ ID NO |
|---|---|---|---|
| KRAS | 3845 | NM_004985.5 | 22 |
| | | NM_033360.4 | 23 |
| | | NM_001369786.1 | 24 |
| | | NM_001369787.1 | 25 |
| | | NM_004985.5 w/G→T substitution at position 34 | 26 |
| | | NM_033360.4 w/G→T substitution at position 34 | 27 |
| | | NM_001369786.1 w/G→T substitution at position 34 | 28 |
| | | NM_001369787.1 w/G→T substitution at position 34 | 29 |
| | | NM_004985.5 w/G→A substitution at position 35 | 30 |
| | | NM_033360.4 w/G→A substitution at position 35 | 31 |
| | | NM_001369786.1 w/G→A substitution at position 35 | 32 |
| | | NM_001369787.1 w/G→A substitution at position 35 | 33 |
| | | NM_004985.5 w/G→T substitution at position 35 | 34 |
| | | NM_033360.4 w/G→T substitution at position 35 | 35 |
| | | NM_001369786.1 w/G→T substitution at position 35 | 36 |
| | | NM_001369787.1 w/G→T substitution at position 35 | 37 |
| c-MYC | 4609 | NM_002467.6 | 38 |
| | | NM_001354870.1 | 39 |
| CD274 | 29126 | NM_014143.4 | 40 |
| | | NM_001267706.2 | 41 |
| | | NM_001314029.2 | 42 |
| | | NR_052005.2 | 43 |
| CD24 | 100133941 | NM_001359084.1 | 44 |
| | | NM_013230.3 | 45 |
| | | NM_001291737.1 | 46 |
| | | NM_001291738.1 | 47 |
| | | NM_001291739.1 | 48 |
| | | NR_117089.1 | 49 |
| | | NR_117090.1 | 50 |
| | | XM_024446293.1 | 51 |
| BIRC5 | 332 | NM_001168.3 | 52 |
| | | NM_001012270.2 | 53 |
| | | NM_001012271.2 | 54 |
| | | XR_243654.5 | 55 |
| | | XR_934452.3 | 56 |
| PKN3 | 29941 | NM_013355.5 | 57 |
| | | NM_001317926.2 | 58 |
| | | XM_005251946.3 | 59 |
| | | XM_006717080.3 | 60 |
| | | XM_017014649.2 | 61 |
| | | XM_017014650.1 | 62 |
| PLK1 | 5347 | NM_005030.6 | 63 |
| FGF1 | 2246 | NM_000800.5 | 64 |
| | | NM_033136.4 | 65 |
| | | NM_033137.4 | 66 |
| | | NM_001144892.3 | 67 |
| | | NM_001144934.2 | 68 |
| | | NM_001144935.2 | 69 |
| | | NM_001257205.1 | 70 |
| | | NM_001257206.2 | 71 |
| | | NM_001257207.2 | 72 |
| | | NM_001257208.2 | 73 |
| | | NM_001257209.1 | 74 |
| | | NM_001257210.2 | 75 |
| | | NM_001257211.2 | 76 |
| | | NM_001257212.2 | 77 |
| | | NM_001354951.2 | 78 |
| | | NM_001354952.2 | 79 |
| | | NM_001354953.2 | 80 |
| | | NM_001354954.2 | 81 |
| | | NM_001354955.2 | 82 |
| | | NM_001354956.2 | 83 |
| | | NM_001354957.2 | 84 |
| | | NM_001354958.2 | 85 |
| | | NM_001354959.2 | 86 |
| | | NM_001354961.2 | 87 |
| | | NM_001354962.2 | 88 |
| | | NM_001354963.2 | 89 |
| | | NM_001354964.2 | 90 |
| FGF2 | 2247 | NM_001361665.2 | 91 |
| | | NM_002006.5 | 92 |
| FGF5 | 2250 | NM_004464.4 | 93 |
| | | NM_033143.2 | 94 |
| | | NM_001291812.2 | 95 |
| EGFR | 1956 | NM_005228.5 | 96 |
| | | NM_201282.2 | 97 |
| | | NM_201283.2 | 98 |
| | | NM_201284.2 | 99 |
| | | NM_001346897.2 | 100 |
| | | NM_001346898.2 | 101 |
| | | NM_001346899.2 | 102 |
| | | NM_001346900.2 | 103 |
| | | NM_001346941.2 | 104 |
| VEGFA | 7422 | NM_003376.6 | 105 |
| | | NM_001025366.3 | 106 |
| | | NM_001025367.3 | 107 |
| | | NM_001025368.3 | 108 |
| | | NM_001025369.3 | 109 |
| | | NM_001025370.3 | 110 |
| | | NM_001033756.3 | 111 |
| | | NM_001171622.2 | 112 |
| | | NM_001171623.2 | 113 |
| | | NM_001171624.2 | 114 |
| | | NM_001171625.2 | 115 |
| | | NM_001171626.2 | 116 |
| | | NM_001171627.2 | 117 |
| | | NM_001171628.2 | 118 |
| | | NM_001171629.2 | 119 |
| | | NM_001171630.2 | 120 |
| | | NM_001204384.2 | 121 |
| | | NM_001204385.2 | 122 |
| | | NM_001287044.2 | 123 |
| | | NM_001317010.1 | 124 |
| VEGFB | 7423 | NM_003377.5 | 125 |
| | | NM_001243733.2 | 126 |
| KDR | 3791 | NM_002253.4 | 127 |
| ERBB2 | 2064 | NM_004448.4 | 128 |
| | | NM_001005862.3 | 129 |
| | | NM_001289936.2 | 130 |
| | | NM_001289937.2 | 131 |
| | | NM_001289938.2 | 132 |
| | | NM_001382782.1 | 133 |
| | | NM_001382783.1 | 134 |
| | | NM_001382784.1 | 135 |
| | | NM_001382785.1 | 136 |
| | | NM_001382786.1 | 137 |
| | | NM_001382787.1 | 138 |
| | | NM_001382788.1 | 139 |
| | | NM_001382789.1 | 140 |
| | | NM_001382790.1 | 141 |
| | | NM_001382791.1 | 142 |
| | | NM_001382792.1 | 143 |
| | | NM_001382793.1 | 144 |
| | | NM_001382794.1 | 145 |
| | | NM_001382795.1 | 146 |
| | | NM_001382796.1 | 147 |
| | | NM_001382797.1 | 148 |
| | | NM_001382798.1 | 149 |
| | | NM_001382799.1 | 150 |
| | | NM_001382800.1 | 151 |
| | | NM_001382801.1 | 152 |
| | | NM_001382802.1 | 153 |
| | | NM_001382803.1 | 154 |
| | | NM_001382804.1 | 155 |
| | | NM_001382805.1 | 156 |
| | | NM_001382806.1 | 157 |

TABLE 1-continued siRNA and shRNA Cancer (Cancer Cell) Target Transcripts

| Gene | GenBank Gene ID | GenBank cDNA RefSeq Accession | (mRNA) SEQ ID NO |
|---|---|---|---|
|  |  | NR_110535.2 | 158 |
|  |  | XM_024450641.1 | 159 |
|  |  | XM_024450642.1 | 160 |
|  |  | XM_024450643.1 | 161 |
| EPHA2 | 1969 | NM_004431.5 | 162 |
|  |  | NM_001329090.2 | 163 |
|  |  | XM_017000537.1 | 164 |
| RRM2 | 6241 | NM_001034.4 | 165 |
|  |  | NM_001165931.1 | 166 |
|  |  | NR_164157.1 | 167 |
| PSMB9 | 5698 | NM_002800.5 | 168 |
| PSMB8 | 5696 | NM_148919.4 | 169 |
|  |  | NM_004159.5 | 170 |
| MCL1 | 4170 | NM_021960.5 | 171 |
|  |  | NM_182763.3 | 172 |
|  |  | NM_001197320.2 | 173 |
| CBLB | 868 | NM_170662.5 | 174 |
|  |  | NM_001321786.1 | 175 |
|  |  | NM_001321788.2 | 176 |
|  |  | NM_001321789.1 | 177 |
|  |  | NM_001321790.2 | 178 |
|  |  | NM_001321791.2 | 179 |
|  |  | NM_001321793.2 | 180 |
|  |  | NM_001321794.2 | 181 |
|  |  | NM_001321795.2 | 182 |
|  |  | NM_001321796.2 | 183 |
|  |  | NM_001321797.2 | 184 |
|  |  | NM_001321798.2 | 185 |
|  |  | NM_001321799.2 | 186 |
|  |  | NM_001321806.2 | 187 |
|  |  | NM_001321807.2 | 188 |
|  |  | NM_001321808.2 | 189 |
|  |  | NM_001321811.2 | 190 |
|  |  | NM_001321813.1 | 191 |
|  |  | NM_001321816.2 | 192 |
|  |  | NM_001321820.2 | 193 |
|  |  | NM_001321822.2 | 194 |
|  |  | NR_135806.2 | 195 |
|  |  | NR_135807.2 | 196 |
|  |  | NR_135808.2 | 197 |
|  |  | NR_135809.2 | 198 |
|  |  | NR_135810.2 | 199 |
|  |  | NR_135811.2 | 200 |
|  |  | NR_135812.1 | 201 |
|  |  | XM_011513257.1 | 202 |
|  |  | XM_011513259.3 | 203 |
|  |  | XM_017007395.1 | 204 |
|  |  | XM_017007397.1 | 205 |
|  |  | XM_017007396.1 | 206 |
|  |  | XM_017007399.1 | 207 |
|  |  | XM_017007398.1 | 208 |
|  |  | XM_017007400.1 | 209 |
|  |  | XR_001740338.1 | 210 |
|  |  | XR_001740339.1 | 211 |
| RHOA | 387 | NM_001664.4 | 212 |
|  |  | NM_001313941.2 | 213 |
|  |  | NM_001313943.2 | 214 |
|  |  | NM_001313944.2 | 215 |
|  |  | NM_001313945.2 | 216 |
|  |  | NM_001313946.2 | 217 |
|  |  | NM_001313947.2 | 218 |
| FLI1 | 2313 | NM_002017.5 | 219 |
|  |  | NM_001167681.3 | 220 |
|  |  | NM_001271010.2 | 221 |
|  |  | NM_001271012.2 | 222 |
|  |  | XM_011542701.2 | 223 |
|  |  | XM_011542702.1 | 224 |
|  |  | XM_017017405.1 | 225 |
|  |  | XM_017017406.1 | 226 |
| EWSR1 | 2130 | NM_005243.4 | 227 |
|  |  | NM_013986.4 | 228 |
|  |  | NM_001163285.2 | 229 |
|  |  | NM_001163286.2 | 230 |
|  |  | NM_001163287.2 | 231 |
|  |  | XM_005261389.4 | 232 |
|  |  | XM_005261390.4 | 233 |
|  |  | XM_011529995.3 | 234 |
|  |  | XM_011529996.3 | 235 |
|  |  | XM_011529997.2 | 236 |
|  |  | XM_011529998.2 | 237 |
|  |  | XM_011529999.2 | 238 |
|  |  | XM_011530000.2 | 239 |
|  |  | XM_011530001.2 | 240 |
|  |  | XM_011530002.3 | 241 |
|  |  | XM_017028644.2 | 242 |
|  |  | XM_017028645.2 | 243 |
|  |  | XM_017028646.2 | 244 |
|  |  | XM_017028647.2 | 245 |
|  |  | XM_017028649.2 | 246 |
|  |  | XM_017028648.2 | 247 |
|  |  | XM_017028650.2 | 248 |
|  |  | XM_017028651.2 | 249 |
|  |  | XM_017028652.2 | 250 |
|  |  | XM_017028653.2 | 251 |
|  |  | XM_017028654.1 | 252 |
|  |  | XM_017028655.1 | 253 |
|  |  | XM_017028656.2 | 254 |
|  |  | XM_017028657.2 | 255 |
|  |  | XM_017028659.1 | 256 |
|  |  | XM_017028658.1 | 257 |
|  |  | XM_017028660.2 | 258 |
|  |  | XM_017028661.2 | 259 |
|  |  | XM_017028662.2 | 260 |
|  |  | XM_017028663.1 | 261 |
|  |  | XM_017028664.2 | 262 |
|  |  | XM_017028665.2 | 263 |
|  |  | XM_017028666.2 | 264 |
|  |  | XM_024452180.1 | 265 |
|  |  | XM_024452181.1 | 266 |
|  |  | XR_002958676.1 | 267 |
| STAT3 | 6774 | NM_139276.3 | 268 |
|  |  | NM_003150.4 | 269 |
|  |  | NM_213662.2 | 270 |
|  |  | NM_001369512.1 | 271 |
|  |  | NM_001369513.1 | 272 |
|  |  | NM_001369514.1 | 273 |
|  |  | NM_001369516.1 | 274 |
|  |  | NM_001369517.1 | 275 |
|  |  | NM_001369518.1 | 276 |
|  |  | NM_001369519.1 | 277 |
|  |  | NM_001369520.1 | 278 |
|  |  | NM_001384984.1 | 279 |
|  |  | NM_001384985.1 | 280 |
|  |  | NM_001384986.1 | 281 |
|  |  | NM_001384987.1 | 282 |
|  |  | NM_001384988.1 | 283 |
|  |  | NM_001384989.1 | 284 |
|  |  | NM_001384990.1 | 285 |
|  |  | NM_001384991.1 | 286 |
|  |  | NM_001384992.1 | 287 |
|  |  | NM_001384993.1 | 288 |
|  |  | XM_017024973.2 | 289 |
|  |  | XM_024450896.1 | 290 |
| TWIST1 | 7291 | NM_000474.4 | 291 |
|  |  | NR_149001.2 | 292 |
| FOLH1 | 2346 | NM_004476.3 | 293 |
|  |  | NM_001014986.3 | 294 |
|  |  | NM_001193471.3 | 295 |
|  |  | NM_001193472.3 | 296 |
|  |  | NM_001193473.3 | 297 |
|  |  | NM_001351236.2 | 298 |
|  |  | XM_011519958.3 | 299 |
|  |  | XM_017017432.1 | 300 |
|  |  | XM_017017433.2 | 301 |
|  |  | XM_017017434.1 | 302 |
|  |  | XM_017017435.2 | 303 |
|  |  | XM_017017444.2 | 304 |
|  |  | XM_017017445.1 | 305 |

TABLE 1-continued siRNA and shRNA Cancer (Cancer Cell) Target Transcripts

| Gene | GenBank Gene ID | GenBank cDNA RefSeq Accession | (mRNA) SEQ ID NO |
|---|---|---|---|
| | | XM_017017446.1 | 306 |
| | | XM_017017447.1 | 307 |
| | | XM_017017448.1 | 308 |
| | | XM_017017449.2 | 309 |
| | | XM_017017450.2 | 310 |
| | | XM_017017451.2 | 311 |
| | | XM_024448411.1 | 312 |
| | | XR_001747818.1 | 313 |
| | | XR_001747819.1 | 314 |
| HIF1A | 3091 | NM_001530.4 | 315 |
| | | NM_181054.3 | 316 |
| | | NM_001243084.2 | 317 |
| SERPINH1 | 871 | NM_001235.5 | 318 |
| | | NM_001207014.3 | 319 |
| | | XM_011545327.1 | 320 |
| | | XM_024448756.1 | 321 |
| PTK2 | 5747 | NM_001387646.1 | 322 |
| | | NM_005607.5 | 323 |
| | | NM_153831.4 | 324 |
| | | NM_001199649.2 | 325 |
| | | NM_001316342.2 | 326 |
| | | NM_001352694.2 | 327 |
| | | NM_001352695.2 | 328 |
| | | NM_001352696.2 | 329 |
| | | NM_001352697.2 | 330 |
| | | NM_001352698.2 | 331 |
| | | NM_001352699.2 | 332 |
| | | NM_001352700.2 | 333 |
| | | NM_001352701.2 | 334 |
| | | NM_001352702.2 | 335 |
| | | NM_001352703.2 | 336 |
| | | NM_001352704.2 | 337 |
| | | NM_001352705.2 | 338 |
| | | NM_001352706.2 | 339 |
| | | NM_001352707.2 | 340 |
| | | NM_001352708.2 | 341 |
| | | NM_001352709.2 | 342 |
| | | NM_001352710.2 | 343 |
| | | NM_001352711.2 | 344 |
| | | NM_001352712.2 | 345 |
| | | NM_001352713.2 | 346 |
| | | NM_001352714.2 | 347 |
| | | NM_001352715.2 | 348 |
| | | NM_001352716.2 | 349 |
| | | NM_001352717.2 | 350 |
| | | NM_001352718.2 | 351 |
| | | NM_001352719.2 | 352 |
| | | NM_001352720.2 | 353 |
| | | NM_001352721.2 | 354 |
| | | NM_001352722.2 | 355 |
| | | NM_001352723.2 | 356 |
| | | NM_001352724.2 | 357 |
| | | NM_001352725.2 | 358 |
| | | NM_001352726.2 | 359 |
| | | NM_001352727.2 | 360 |
| | | NM_001352728.2 | 361 |
| | | NM_001352729.2 | 362 |
| | | NM_001352730.2 | 363 |
| | | NM_001352731.2 | 364 |
| | | NM_001352732.2 | 365 |
| | | NM_001352733.2 | 366 |
| | | NM_001352734.2 | 367 |
| | | NM_001352735.2 | 368 |
| | | NM_001352736.2 | 369 |
| | | NM_001352737.2 | 370 |
| | | NM_001352738.2 | 371 |
| | | NM_001352739.2 | 372 |
| | | NM_001352740.2 | 373 |
| | | NM_001352741.2 | 374 |
| | | NM_001352742.2 | 375 |
| | | NM_001352743.2 | 376 |
| | | NM_001352744.2 | 377 |
| | | NM_001352745.2 | 378 |
| | | NM_001352746.2 | 379 |
| | | NM_001352747.2 | 380 |
| | | NM_001352748.2 | 381 |
| | | NM_001352749.2 | 382 |
| | | NM_001352750.2 | 383 |
| | | NM_001352751.2 | 384 |
| | | NM_001352752.2 | 385 |
| | | NM_001387584.1 | 386 |
| | | NM_001387585.1 | 387 |
| | | NM_001387586.1 | 388 |
| | | NM_001387587.1 | 389 |
| | | NM_001387588.1 | 390 |
| | | NM_001387589.1 | 391 |
| | | NM_001387590.1 | 392 |
| | | NM_001387591.1 | 393 |
| | | NM_001387592.1 | 394 |
| | | NM_001387603.1 | 395 |
| | | NM_001387604.1 | 396 |
| | | NM_001387605.1 | 397 |
| | | NM_001387606.1 | 398 |
| | | NM_001387607.1 | 399 |
| | | NM_001387608.1 | 400 |
| | | NM_001387609.1 | 401 |
| | | NM_001387610.1 | 402 |
| | | NM_001387611.1 | 403 |
| | | NM_001387612.1 | 404 |
| | | NM_001387613.1 | 405 |
| | | NM_001387614.1 | 406 |
| | | NM_001387615.1 | 407 |
| | | NM_001387616.1 | 408 |
| | | NM_001387617.1 | 409 |
| | | NM_001387618.1 | 410 |
| | | NM_001387619.1 | 411 |
| | | NM_001387620.1 | 412 |
| | | NM_001387621.1 | 413 |
| | | NM_001387622.1 | 414 |
| | | NM_001387623.1 | 415 |
| | | NM_001387624.1 | 416 |
| | | NM_001387625.1 | 417 |
| | | NM_001387627.1 | 418 |
| | | NM_001387628.1 | 419 |
| | | NM_001387629.1 | 420 |
| | | NM_001387630.1 | 421 |
| | | NM_001387631.1 | 422 |
| | | NM_001387632.1 | 423 |
| | | NM_001387633.1 | 424 |
| | | NM_001387634.1 | 425 |
| | | NM_001387635.1 | 426 |
| | | NM_001387636.1 | 427 |
| | | NM_001387637.1 | 428 |
| | | NM_001387638.1 | 429 |
| | | NM_001387639.1 | 430 |
| | | NM_001387640.1 | 431 |
| | | NM_001387641.1 | 432 |
| | | NM_001387642.1 | 433 |
| | | NM_001387643.1 | 434 |
| | | NM_001387644.1 | 435 |
| | | NM_001387645.1 | 436 |
| | | NM_001387647.1 | 437 |
| | | NM_001387648.1 | 438 |
| | | NM_001387649.1 | 439 |
| | | NM_001387650.1 | 440 |
| | | NM_001387651.1 | 441 |
| | | NM_001387652.1 | 442 |
| | | NM_001387653.1 | 443 |
| | | NM_001387654.1 | 444 |
| | | NM_001387655.1 | 445 |
| | | NM_001387656.1 | 446 |
| | | NM_001387657.1 | 447 |
| | | NM_001387658.1 | 448 |
| | | NM_001387659.1 | 449 |
| | | NM_001387660.1 | 450 |
| | | NM_001387661.1 | 451 |
| | | NM_001387662.1 | 452 |
| | | NR_148036.2 | 453 |

TABLE 1-continued siRNA and shRNA Cancer (Cancer Cell) Target Transcripts

| Gene | GenBank Gene ID | GenBank cDNA RefSeq Accession | (mRNA) SEQ ID NO |
|---|---|---|---|
| | | NR_148037.2 | 454 |
| | | NR_148038.2 | 455 |
| | | NR_148039.2 | 456 |
| | | NR_170670.1 | 457 |
| | | NR_170671.1 | 458 |
| | | NR_170672.1 | 459 |
| | | NR_170673.1 | 460 |
| | | XM_017013654.2 | 461 |
| | | XM_017013656.2 | 462 |
| | | XM_017013666.1 | 463 |
| | | XM_017013669.2 | 464 |
| | | XM_017013684.2 | 465 |
| | | XM_017013688.2 | 466 |
| | | XM_024447199.1 | 467 |
| | | XM_024447200.1 | 468 |
| | | XM_024447202.1 | 469 |
| | | XM_024447201.1 | 470 |
| | | XM_024447204.1 | 471 |
| | | XM_024447203.1 | 472 |
| | | XM_024447206.1 | 473 |
| | | XM_024447205.1 | 474 |
| | | XM_024447208.1 | 475 |
| | | XM_024447207.1 | 476 |
| | | XM_024447210.1 | 477 |
| | | XM_024447209.1 | 478 |
| | | XM_024447211.1 | 479 |
| CEACAM6 | 4680 | NM_002483.7 | 480 |
| | | XM_011526990.2 | 481 |
| CXCR4 | 7852 | NM_003467.3 | 482 |
| | | NM_001008540.2 | 483 |
| | | NM_001348056.2 | 484 |
| | | NM_001348059.2 | 485 |
| | | NM_001348060.2 | 486 |
| CTNNB1 | 1499 | NM_001904.4 | 487 |
| | | NM_001098209.2 | 488 |
| | | NM_001098210.2 | 489 |
| | | NM_001330729.2 | 490 |
| | | XM_006712983.2 | 491 |
| | | XM_006712985.1 | 492 |
| | | XM_017005738.1 | 493 |
| | | XM_024453356.1 | 494 |
| | | XM_024453357.1 | 495 |
| | | XM_024453358.1 | 496 |
| | | XM_024453359.1 | 497 |
| | | XM_024453360.1 | 498 |
| BCL2 | 596 | NM_000633.3 | 499 |
| | | NM_000657.3 | 500 |
| | | XM_011526135.3 | 501 |
| | | XM_017025917.2 | 502 |
| | | XR_935248.3 | 503 |
| BCL2L1 | 598 | NM_138578.3 | 504 |
| | | NM_001191.4 | 505 |
| | | NM_001317919.2 | 506 |
| | | NM_001317920.2 | 507 |
| | | NM_001317921.2 | 508 |
| | | NM_001322239.2 | 509 |
| | | NM_001322240.2 | 510 |
| | | NM_001322242.2 | 511 |
| | | NR_134257.1 | 512 |
| | | XM_011528964.2 | 513 |
| | | XM_017027993.1 | 514 |
| | | XR_936599.3 | 515 |
| | | XR_001754364.2 | 516 |
| SST | 6750 | NM_001048.4 | 517 |
| RAF1 | 5894 | NM_001354689.3 | 518 |
| | | NM_002880.4 | 519 |
| | | NM_001354690.3 | 520 |
| | | NM_001354691.3 | 521 |
| | | NM_001354692.3 | 522 |
| | | NM_001354693.3 | 523 |
| | | NM_001354694.3 | 524 |
| | | NM_001354695.3 | 525 |
| | | NR_148940.3 | 526 |
| | | NR_148941.3 | 527 |
| | | NR_148942.3 | 528 |
| | | XM_011533974.3 | 529 |
| | | XM_017006966.1 | 530 |
| | | XR_001740227.1 | 531 |
| SKP2 | 6502 | NM_005983.4 | 532 |
| | | NM_032637.4 | 533 |
| | | NM_001243120.2 | 534 |
| | | XM_011514082.3 | 535 |
| | | XM_011514083.3 | 536 |
| | | XM_017009753.1 | 537 |
| | | XR_001742203.2 | 538 |
| PLAUR | 5329 | NM_002659.4 | 539 |
| | | NM_001005376.3 | 540 |
| | | NM_001005377.3 | 541 |
| | | NM_001301037.2 | 542 |
| | | XM_005258990.5 | 543 |
| | | XM_011527027.2 | 544 |
| | | XM_011527028.3 | 545 |
| | | XM_011527029.2 | 546 |
| | | XM_011527030.2 | 547 |
| | | XM_011527031.3 | 548 |
| | | XM_017026872.2 | 549 |
| | | XM_017026873.1 | 550 |
| MDM2 | 4193 | NM_002392.6 | 551 |
| | | NM_001145337.3 | 552 |
| | | NM_001145339.2 | 553 |
| | | NM_001145340.3 | 554 |
| | | NM_001278462.2 | 555 |
| | | NM_001367990.1 | 556 |
| | | XM_006719399.4 | 557 |
| | | XM_006719400.4 | 558 |
| RAD51 | 5888 | NM_002875.5 | 559 |
| | | NM_133487.4 | 560 |
| | | NM_001164269.2 | 561 |
| | | NM_001164270.2 | 562 |
| | | XM_006720626.3 | 563 |
| | | XM_011521857.2 | 564 |
| | | XM_011521858.2 | 565 |
| | | XM_011521859.2 | 566 |
| | | XM_011521860.2 | 567 |
| | | XM_011521861.2 | 568 |
| | | XM_011521862.3 | 569 |
| EZH2 | 2146 | NM_004456.5 | 570 |
| | | NM_152998.3 | 571 |
| | | NM_001203247.2 | 572 |
| | | NM_001203248.2 | 573 |
| | | NM_001203249.2 | 574 |
| | | XM_005249962.4 | 575 |
| | | XM_005249963.4 | 576 |
| | | XM_005249964.4 | 577 |
| | | XM_011515883.2 | 578 |
| | | XM_011515884.2 | 579 |
| | | XM_011515885.2 | 580 |
| | | XM_011515886.2 | 581 |
| | | XM_011515887.3 | 582 |
| | | XM_011515888.2 | 583 |
| | | XM_011515889.2 | 584 |
| | | XM_011515890.2 | 585 |
| | | XM_011515891.3 | 586 |
| | | XM_011515892.2 | 587 |
| | | XM_011515893.2 | 588 |
| | | XM_011515894.2 | 589 |
| | | XM_011515895.2 | 590 |
| | | XM_011515896.2 | 591 |
| | | XM_011515897.2 | 592 |
| | | XM_011515898.2 | 593 |
| | | XM_011515899.3 | 594 |
| | | XM_011515901.3 | 595 |
| | | XM_017011817.2 | 596 |
| | | XM_017011818.1 | 597 |
| | | XM_017011819.1 | 598 |
| | | XM_017011820.2 | 599 |
| | | XM_017011821.1 | 600 |
| | | XM_024446680.1 | 601 |

TABLE 1-continued siRNA and shRNA Cancer (Cancer Cell) Target Transcripts

| Gene | GenBank Gene ID | GenBank cDNA RefSeq Accession | (mRNA) SEQ ID NO |
|---|---|---|---|
| | | XR_001744581.1 | 602 |
| | | XR_002956413.1 | 603 |
| | | XR_002956414.1 | 604 |
| TP53 | 7157 | NM_000546.6 | 605 |
| | | NM_001126112.3 | 606 |
| | | NM_001126113.3 | 607 |
| | | NM_001126114.3 | 608 |
| | | NM_001126115.2 | 609 |
| | | NM_001126116.2 | 610 |
| | | NM_001126117.2 | 611 |
| | | NM_001126118.2 | 612 |
| | | NM_001276695.3 | 613 |
| | | NM_001276696.3 | 614 |
| | | NM_001276697.3 | 615 |
| | | NM_001276698.3 | 616 |
| | | NM_001276699.3 | 617 |
| | | NM_001276760.3 | 618 |
| | | NM_001276761.3 | 619 |
| CCNB1 | 891 | NM_031966.4 | 620 |
| | | NM_001354844.2 | 621 |
| | | NM_001354845.2 | 622 |
| MAD2L1 | 4085 | NM_002358.4 | 623 |
| AKT1 | 207 | NM_001382430.1 | 624 |
| | | NM_005163.2 | 625 |
| | | NM_001014431.2 | 626 |
| | | NM_001014432.2 | 627 |
| | | NM_001382431.1 | 628 |
| | | NM_001382432.1 | 629 |
| | | NM_001382433.1 | 630 |
| | | XR_002957536.1 | 631 |
| AKT2 | 208 | NM_001626.6 | 632 |
| | | NM_001243027.3 | 633 |
| | | NM_001243028.3 | 634 |
| | | NM_001330511.1 | 635 |
| | | XM_011526614.1 | 636 |
| | | XM_011526615.1 | 637 |
| | | XM_011526616.1 | 638 |
| | | XM_011526618.1 | 639 |
| | | XM_011526619.1 | 640 |
| | | XM_011526620.1 | 641 |
| | | XM_011526622.2 | 642 |
| | | XM_017026470.2 | 643 |
| | | XM_024451416.1 | 644 |
| | | XM_024451417.1 | 645 |
| AKT3 | 10000 | NM_005465.7 | 646 |
| | | NM_181690.2 | 647 |
| | | NM_001206729.2 | 648 |
| | | NM_001370074.1 | 649 |
| | | XM_011544014.2 | 650 |
| | | XM_016999985.1 | 651 |
| | | XM_024446000.1 | 652 |
| | | XM_024446892.1 | 653 |
| | | XM_024447938.1 | 654 |
| PECAM1 | 5175 | NM_000442.5 | 655 |
| | | XM_005276880.1 | 656 |
| | | XM_005276881.1 | 657 |
| | | XM_005276882.1 | 658 |
| | | XM_005276883.2 | 659 |
| | | XM_011524889.2 | 660 |
| | | XM_011524890.1 | 661 |
| | | XM_017024738.1 | 662 |
| | | XM_017024739.1 | 663 |
| | | XM_017024740.1 | 664 |
| | | XM_017024741.1 | 665 |
| KLF5 | 688 | NM_001730.5 | 666 |
| | | NM_001286818.2 | 667 |
| PLXDC1 | 57125 | NM_020405.5 | 668 |
| UBE3A | 7337 | NM_130839.5 | 669 |
| | | NM_000462.5 | 670 |
| | | NM_130838.4 | 671 |
| | | NM_001354505.1 | 672 |
| | | NM_001354506.2 | 673 |
| | | NM_001354507.2 | 674 |
| | | NM_001354508.2 | 675 |
| | | NM_001354509.2 | 676 |
| | | NM_001354511.2 | 677 |
| | | NM_001354512.2 | 678 |
| | | NM_001354513.2 | 679 |
| | | NM_001354523.2 | 680 |
| | | NM_001354526.1 | 681 |
| | | NM_001354538.2 | 682 |
| | | NM_001354539.2 | 683 |
| | | NM_001354540.2 | 684 |
| | | NM_001354541.2 | 685 |
| | | NM_001354542.2 | 686 |
| | | NM_001354543.2 | 687 |
| | | NM_001354544.2 | 688 |
| | | NM_001354545.2 | 689 |
| | | NM_001354546.2 | 690 |
| | | NM_001354547.2 | 691 |
| | | NM_001354548.2 | 692 |
| | | NM_001354549.2 | 693 |
| | | NM_001354550.2 | 694 |
| | | NM_001354551.2 | 695 |
| | | NM_001374461.1 | 696 |
| | | NR_148916.2 | 697 |
| | | XM_011521995.3 | 698 |
| | | XM_017022547.2 | 699 |
| | | XM_017022548.2 | 700 |
| | | XM_017022550.2 | 701 |
| | | XM_017022556.2 | 702 |
| | | XM_024450043.1 | 703 |
| RET | 5979 | NM_020975.6 | 704 |
| | | NM_020630.6 | 705 |
| | | NM_001355216.1 | 706 |
| SSX1 | 6756 | NM_005635.4 | 707 |
| | | NM_001278691.2 | 708 |
| SS18 | 6760 | NM_001007559.3 | 709 |
| | | NM_005637.4 | 710 |
| | | NM_001308201.2 | 711 |
| | | XM_006722527.2 | 712 |
| | | XM_011526145.1 | 713 |
| | | XM_011526147.2 | 714 |
| | | XM_011526148.2 | 715 |
| | | XM_011526149.2 | 716 |
| | | XM_011526150.2 | 717 |
| | | XM_011526151.2 | 718 |
| | | XM_011526152.2 | 719 |
| RECQL | 5965 | NM_002907.4 | 720 |
| | | NM_032941.3 | 721 |
| | | XM_005253461.3 | 722 |
| | | XM_005253462.5 | 723 |
| | | XM_005253463.4 | 724 |
| | | XM_005253464.4 | 725 |
| RAN | 5901 | NM_006325.5 | 726 |
| | | NM_001300796.2 | 727 |
| | | NM_001300797.2 | 728 |
| | | XM_017019772.1 | 729 |
| | | XM_017019773.1 | 730 |
| ABCB1 | 5243 | NM_001348946.2 | 731 |
| | | NM_000927.5 | 732 |
| | | NM_001348944.2 | 733 |
| | | NM_001348945.2 | 734 |
| ACTB | 60 | NM_001101.5 | 735 |
| POSTN | 10631 | NM_006475.3 | 736 |
| | | NM_001135934.2 | 737 |
| | | NM_001135935.2 | 738 |
| | | NM_001135936.2 | 739 |
| | | NM_001286665.2 | 740 |
| | | NM_001286666.2 | 741 |
| | | NM_001286667.2 | 742 |
| | | NM_001330517.2 | 743 |
| | | XM_005266232.2 | 744 |
| | | XM_017020355.1 | 745 |
| | | XM_017020356.1 | 746 |
| KIF11 | 3832 | NM_004523.4 | 747 |
| XIAP | 331 | NM_001167.4 | 771 |
| | | NM_001204401.2 | 772 |

TABLE 1-continued siRNA and shRNA Cancer (Cancer Cell) Target Transcripts

| Gene | GenBank Gene ID | GenBank cDNA RefSeq Accession | (mRNA) SEQ ID NO |
|---|---|---|---|
| | | NM_001378590.1 | 773 |
| | | NM_001378591.1 | 774 |
| | | NM_001378592.1 | 775 |
| | | NR_037916.2 | 776 |
| | | NR_165803.1 | 777 |
| TERT | 7015 | NM_198253.3 | 778 |
| | | NM_001193376.3 | 779 |
| | | NR_149162.3 | 780 |
| | | NR_149163.3 | 781 |
| IGF1R | 3480 | NM_000875.5 | 782 |
| | | NM_001291858.2 | 783 |
| | | XM_011521516.2 | 784 |
| | | XM_011521517.2 | 785 |
| | | XM_017022136.1 | 786 |
| | | XM_017022137.1 | 787 |
| | | XM_017022138.1 | 788 |
| | | XM_017022139.1 | 789 |
| | | XM_024449913.1 | 790 |
| MMP9 | 4318 | NM_004994.3 | 791 |
| CCDC6 | 8030 | NM_005436.5 | 792 |
| NCOA4 | 8031 | NM_001145263.2 | 793 |
| | | NM_005437.4 | 794 |
| | | NM_001145260.2 | 795 |
| | | NM_001145261.2 | 796 |
| | | NM_001145262.2 | 797 |
| CD44 | 960 | NM_000610.4 | 798 |
| | | NM_001001389.2 | 799 |
| | | NM_001001390.2 | 800 |
| | | NM_001001391.2 | 801 |
| | | NM_001001392.2 | 802 |
| | | NM_001202555.2 | 803 |
| | | NM_001202556.2 | 804 |
| | | NM_001202557.2 | 805 |
| | | XM_005253231.3 | 806 |
| | | XM_005253232.3 | 807 |
| | | XM_005253235.3 | 808 |
| | | XM_005253238.3 | 809 |
| | | XM_005253239.3 | 810 |
| | | XM_005253240.3 | 811 |
| | | XM_006718388.2 | 812 |
| | | XM_006718390.4 | 813 |
| | | XM_011520482.2 | 814 |
| | | XM_011520483.2 | 815 |
| | | XM_011520484.2 | 816 |
| | | XM_011520485.2 | 817 |
| | | XM_011520486.2 | 818 |
| | | XM_011520487.3 | 819 |
| | | XM_011520488.2 | 820 |
| | | XM_011520489.3 | 821 |
| | | XM_017018583.2 | 822 |
| | | XM_017018584.2 | 823 |
| | | XM_017018585.2 | 824 |

Reducing the expression of genes using siRNA-mediated RNAi is also useful in the treatment of viral infections. For example, reducing the expression of a set of genes that enables an infected cell to evade the host's immune system, or a set of genes that is required for viral replication, hinders proliferation of the virus in the host. Such genes, and their mRNA transcripts, are listed in Table 2. Thus, the transcripts of the genes listed in Table 2 are key targets for the treatment of a viral infection using siRNA-mediated RNAi.

Accordingly, in some embodiments, an API useful for the treatment of viral infections in a mammal is siRNA, the siRNA being a double-stranded RNA molecule including an antisense RNA strand and a sense RNA strand, wherein: (a) the antisense RNA strand is 19-29 nucleotides in length and is complementary to contiguous nucleotides in a target mammalian mRNA sequence, the mRNA sequence being selected from the group consisting of SEQ ID NO: 8-21, 482-486, and 748-765, (b) the sense RNA strand is 19-29 nucleotides in length and is complementary to 14-29 nucleotides from the antisense RNA strand, and (c) the double stranded RNA molecule has a double stranded region of 14-29 nucleotides in length and a 3' overhang region of 0-5 nucleotides in length.

In some embodiments, an API useful for the treatment of viral infections in a mammal is siRNA, the siRNA being a double-stranded RNA molecule including an antisense RNA strand and a sense RNA strand, wherein: (a) the antisense RNA strand is 19-29 nucleotides in length and is complementary to contiguous nucleotides in a target mammalian mRNA sequence, the cDNA sequence being selected from the group consisting of SEQ ID NO: 482-486 and 748-765, (b) the sense RNA strand is 19-29 nucleotides in length and is complementary to 14-29 nucleotides from the antisense RNA strand, and (c) the double stranded RNA molecule has a double stranded region of 14-29 nucleotides in length and a 3' overhang region of 0-5 nucleotides in length.

TABLE 2 siRNA and shRNA Viral Infection (Virus-Infected Cell) Target Transcripts

| Gene | GenBank Gene ID | GenBank cDNA RefSeq Accession | (cDNA) SEQ ID NO |
|---|---|---|---|
| CD47 | 961 | NM_001777.4 | 8 |
| | | NM_198793.3 | 9 |
| | | NM_001382306.1 | 10 |
| | | XM_005247909.2 | 11 |
| | | XM_017007536.1 | 12 |
| | | XR_241521.2 | 13 |
| | | XR_241522.2 | 14 |
| | | XR_924218.2 | 15 |
| | | XR_924219.2 | 16 |
| | | XR_924220.2 | 17 |
| | | XR_001740374.2 | 18 |
| | | XR_001740375.2 | 19 |
| | | XR_002959610.1 | 20 |
| | | XR_002959611.1 | 21 |
| ACE2 | 59272 | NM_001371415.1 | 748 |
| | | NM_021804.3 | 749 |
| | | NM_001386259.1 | 750 |
| | | NM_001386260.1 | 751 |
| | | NM_001388452.1 | 752 |
| | | NM_001389402.1 | 753 |
| CCR5 | 1234 | NM_001394783.1 | 754 |
| | | NM_000579.4 | 755 |
| | | NM_001100168.2 | 756 |
| CXCR4 | 7852 | NM_003467.3 | 482 |
| | | NM_001008540.2 | 483 |
| | | NM_001348056.2 | 484 |
| | | NM_001348059.2 | 485 |
| | | NM_001348060.2 | 486 |
| TAT | 6898 | NM_000353.3 | 757 |
| PKN2 | 5586 | NM_006256.4 | 758 |
| | | NM_001320707.2 | 759 |
| | | NM_001320708.2 | 760 |
| | | NM_001320709.2 | 761 |
| | | XM_011541772.2 | 762 |
| | | XM_017001782.2 | 763 |
| | | XM_017001783.2 | 764 |
| EPHA1 | 2041 | NM_005232.5 | 765 |

Increased CD47 expression has been observed in fibrotic fibroblast cells, and blocking CD47 reverses fibrosis by increasing phagocytosis of profibrotic fibroblasts and by eliminating suppressive effects on adaptive immunity. In addition to CD47, expression of other the genes listed in Table 3 has been associated with the promotion of fibrosis. Reducing the expression of these genes using siRNA-mediated RNAi is also useful in the treatment of fibrotic diseases. Such genes, and their mRNA transcripts, are listed in Table 3. Thus, the transcripts of the genes listed in Table 3 represent key targets for the treatment of fibrotic diseases using siRNA-mediated RNAi.

In some embodiments, an API useful for the treatment of fibrotic disease in a mammal is siRNA, the siRNA being a double-stranded RNA molecule including an antisense RNA strand and a sense RNA strand, wherein: (a) the antisense RNA strand is 19-29 nucleotides in length and is complementary to contiguous nucleotides in a target mammalian mRNA sequence, the mRNA sequence being selected from the group consisting of SEQ ID NO: 8-21, 40-43, and 766-770, (b) the sense RNA strand is 19-29 nucleotides in length and is complementary to 14-29 nucleotides from the antisense RNA strand, and (c) the double stranded RNA molecule has a double stranded region of 14-29 nucleotides in length and a 3' overhang region of 0-5 nucleotides in length.

In some embodiments, an API useful for the treatment of fibrotic disease in a mammal is siRNA, the siRNA being a double-stranded RNA molecule including an antisense RNA strand and a sense RNA strand, wherein: (a) the antisense RNA strand is 19-29 nucleotides in length and is complementary to contiguous nucleotides in a target mammalian mRNA sequence, the mRNA sequence being selected from the group consisting of SEQ ID NO: 40-43, and 766-770, (b) the sense RNA strand is 19-29 nucleotides in length and is complementary to 14-29 nucleotides from the antisense RNA strand, and (c) the double stranded RNA molecule has a double stranded region of 14-29 nucleotides in length and a 3' overhang region of 0-5 nucleotides in length.

TABLE 3 siRNA and shRNA Fibrotic Disease (Fibrotic Cell) Target Transcripts

| Gene | GenBank Gene ID | GenBank cDNA RefSeq Accession | (mRNA) SEQ ID NO |
|---|---|---|---|
| CD47 | 961 | NM_001777.4 | 8 |
| | | NM_198793.3 | 9 |
| | | NM_001382306.1 | 10 |
| | | XM_005247909.2 | 11 |
| | | XM_017007536.1 | 12 |
| | | XR_241521.2 | 13 |
| | | XR_241522.2 | 14 |
| | | XR_924218.2 | 15 |
| | | XR_924219.2 | 16 |
| | | XR_924220.2 | 17 |
| | | XR_001740374.2 | 18 |
| | | XR_001740375.2 | 19 |
| | | XR_002959610.1 | 20 |
| | | XR_002959611.1 | 21 |
| CD274 | 29126 | NM_014143.4 | 40 |
| | | NM_001267706.2 | 41 |
| | | NM_001314029.2 | 42 |
| | | NR_052005.2 | 43 |
| JUN | 3725 | NM_002228.4 | 766 |
| CFTR | 1080 | NM_000492.4 | 767 |
| SCNN1A | 6337 | NM_001038.6 | 768 |
| | | NM_001159575.2 | 769 |
| | | NM_001159576.2 | 770 |

In accordance with some embodiments, the API may be a short hairpin RNA ("shRNA"). Short hairpin RNA is a single-stranded RNA molecule, forming a stem loop structure, that can reduce the expression of a specific gene by causing the degradation of the gene's mRNA transcript(s), which shares partial complementarity with a region of the shRNA molecule. As with siRNA, the process of reducing the expression of a gene using shRNA is referred to as RNAi. See generally, Rao et al. *Adv Drug Deliv Rev* 61(9):746-59 (2009), which is hereby incorporated by reference herein its entirety.

Several genes have been implicated in promoting cancer progression and cancer cell proliferation through various mechanisms. These genes, and their mRNA transcripts, are listed in Table 1. By reducing the expression of one or more genes from Table 1, cancer progression and cancer cell proliferation may be inhibited. Thus, the transcripts of the genes listed in Table 1 represent key targets for the treatment of cancer using shRNA-mediated RNAi.

Accordingly, in some embodiments, an API useful for the treatment of cancer in a mammal is shRNA, the shRNA being a single-stranded RNA molecule of 44-71 nucleotides in length, and having, in a 5' to 3' direction: a first region of 19-29 nucleotides at the 5' end of the single-stranded RNA molecule, the first region having a first sequence; a second region of 4-11 nucleotides directly adjacent to the first region, the second region having a second sequence; a third region of 19-29 nucleotides directly adjacent to the second region, the third region having a third sequence; and a fourth region of 2 nucleotides at the 3' end of the single-stranded RNA molecule, directly adjacent to the third region, the fourth region having a fourth sequence, wherein: (a) the first region has the same number of nucleotides as the third region, (b) the third sequence is the reverse-complement of the first sequence, (c) the third region is complementary to contiguous nucleotides in a target mammalian mRNA sequence, the mRNA sequence being selected from the group consisting of SEQ ID NO: 8-747 and 771-824, and (d) the single-stranded RNA molecule is configured to form a stem loop structure, the first region base pairing with the third region to form a stem, the second region forming a loop, and the fourth region forming a 3' overhang.

In some embodiments, an API useful for the treatment of cancer in a mammal is shRNA, the shRNA being a single-stranded RNA molecule of 44-71 nucleotides in length, and having, in a 5' to 3' direction: a first region of 19-29 nucleotides at the 5' end of the single-stranded RNA molecule, the first region having a first sequence; a second region of 4-11 nucleotides directly adjacent to the first region, the second region having a second sequence; a third region of 19-29 nucleotides directly adjacent to the second region, the third region having a third sequence; and a fourth region of 2 nucleotides at the 3' end of the single-stranded RNA molecule, directly adjacent to the third region, the fourth region having a fourth sequence, wherein: (a) the first region has the same number of nucleotides as the third region, (b) the third sequence is the reverse-complement of the first sequence, (c) the third region is complementary to contiguous nucleotides in a target mammalian mRNA sequence, the mRNA sequence being selected from the group consisting of SEQ ID NO: 22-747 and 771-824, and (d) the single-stranded RNA molecule is configured to form a stem loop structure, the first region base pairing with the third region to form a stem, the second region forming a loop, and the fourth region forming a 3' overhang.

In some embodiments, an API useful for the treatment of cancer in a mammal is shRNA, the shRNA being a single-stranded RNA molecule of 44-71 nucleotides in length, and having, in a 5' to 3' direction: a first region of 19-29 nucleotides at the 5' end of the single-stranded RNA molecule, the first region having a first sequence; a second region of 4-11 nucleotides directly adjacent to the first region, the second region having a second sequence; a third region of 19-29 nucleotides directly adjacent to the second region, the third region having a third sequence; and a fourth region of 2 nucleotides at the 3' end of the single-stranded RNA molecule, directly adjacent to the third region, the fourth region having a fourth sequence, wherein: (a) the first region has the same number of nucleotides as the third region, (b) the third sequence is the reverse-complement of the first sequence, (c) the third region is complementary to contiguous nucleotides in a target mammalian mRNA sequence, the mRNA sequence being selected from the group consisting of SEQ ID NO: 22-37, and (d) the single-stranded RNA molecule is configured to form a stem loop structure, the first region base pairing with the third region to form a stem, the second region forming a loop, and the fourth region forming a 3' overhang.

In some embodiments, an API useful for the treatment of cancer in a mammal is shRNA, the shRNA being a single-stranded RNA molecule of 44-71 nucleotides in length, and having, in a 5' to 3' direction: a first region of 19-29 nucleotides at the 5' end of the single-stranded RNA molecule, the first region having a first sequence; a second region of 4-11 nucleotides directly adjacent to the first region, the second region having a second sequence; a third region of 19-29 nucleotides directly adjacent to the second region, the third region having a third sequence; and a fourth region of 2 nucleotides at the 3' end of the single-stranded RNA molecule, directly adjacent to the third region, the fourth region having a fourth sequence, wherein: (a) the first region has the same number of nucleotides as the third region, (b) the third sequence is the reverse-complement of the first sequence, (c) the third region is complementary to contiguous nucleotides in a target mammalian mRNA sequence, the mRNA sequence being selected from the group consisting of SEQ ID NO: 38-39, and (d) the single-stranded RNA molecule is configured to form a stem loop structure, the first region base pairing with the third region to form a stem, the second region forming a loop, and the fourth region forming a 3' overhang.

In some embodiments, an API useful for the treatment of cancer in a mammal is shRNA, the shRNA being a single-stranded RNA molecule of 44-71 nucleotides in length, and having, in a 5' to 3' direction: a first region of 19-29 nucleotides at the 5' end of the single-stranded RNA molecule, the first region having a first sequence; a second region of 4-11 nucleotides directly adjacent to the first region, the second region having a second sequence; a third region of 19-29 nucleotides directly adjacent to the second region, the third region having a third sequence; and a fourth region of 2 nucleotides at the 3' end of the single-stranded RNA molecule, directly adjacent to the third region, the fourth region having a fourth sequence, wherein: (a) the first region has the same number of nucleotides as the third region, (b) the third sequence is the reverse-complement of the first sequence, (c) the third region is complementary to contiguous nucleotides in a target mammalian mRNA sequence, the mRNA sequence being selected from the group consisting of SEQ ID NO: 40-43, and (d) the single-stranded RNA molecule is configured to form a stem loop structure, the first region base pairing with the third region to form a stem, the second region forming a loop, and the fourth region forming a 3' overhang.

In some embodiments, an API useful for the treatment of cancer in a mammal is shRNA, the shRNA being a single-stranded RNA molecule of 44-71 nucleotides in length, and having, in a 5' to 3' direction: a first region of 19-29 nucleotides at the 5' end of the single-stranded RNA molecule, the first region having a first sequence; a second region of 4-11 nucleotides directly adjacent to the first region, the second region having a second sequence; a third region of 19-29 nucleotides directly adjacent to the second region, the third region having a third sequence; and a fourth region of 2 nucleotides at the 3' end of the single-stranded RNA molecule, directly adjacent to the third region, the fourth region having a fourth sequence, wherein: (a) the first region has the same number of nucleotides as the third region, (b) the third sequence is the reverse-complement of the first sequence, (c) the third region is complementary to contiguous nucleotides in a target mammalian mRNA sequence, the mRNA sequence being selected from the group consisting of SEQ ID NO: 44-51, and (d) the single-stranded RNA molecule is configured to form a stem loop structure, the first region base pairing with the third region to form a stem, the second region forming a loop, and the fourth region forming a 3' overhang.

Reducing the expression of genes using shRNA-mediated RNAi is also useful in the treatment of viral infections. For example, reducing the expression of a set of genes that enables an infected cell to evade the host's immune system, or a set of genes that is required for viral replication, hinders proliferation of the virus in the host. Such genes, and their mRNA transcripts, are listed in Table 2. Thus, the transcripts of the genes listed in Table 2 are also key targets for the treatment of a viral infection using shRNA-mediated RNAi.

Accordingly, in some embodiments, an API useful for the treatment of viral infections in a mammal is shRNA, the shRNA being a single-stranded RNA molecule of 44-71 nucleotides in length, and having, in a 5' to 3' direction: a first region of 19-29 nucleotides at the 5' end of the single-stranded RNA molecule, the first region having a first sequence; a second region of 4-11 nucleotides directly adjacent to the first region, the second region having a second sequence; a third region of 19-29 nucleotides directly adjacent to the second region, the third region having a third sequence; and a fourth region of 2 nucleotides at the 3' end of the single-stranded RNA molecule, directly adjacent to the third region, the fourth region having a fourth sequence, wherein: (a) the first region has the same number of nucleotides as the third region, (b) the third sequence is the reverse-complement of the first sequence, (c) the third region is complementary to contiguous nucleotides in a target mammalian mRNA sequence, the mRNA sequence being selected from the group consisting of SEQ ID NO: 8-21, 482-486, and 748-765, and (d) the single-stranded RNA molecule is configured to form a stem loop structure, the first region base pairing with the third region to form a stem, the second region forming a loop, and the fourth region forming a 3' overhang.

In some embodiments, an API useful for the treatment of viral infections in a mammal is shRNA, the shRNA being a single-stranded RNA molecule of 44-71 nucleotides in length, and having, in a 5' to 3' direction: a first region of 19-29 nucleotides at the 5' end of the single-stranded RNA molecule, the first region having a first sequence; a second region of 4-11 nucleotides directly adjacent to the first region, the second region having a second sequence; a third region of 19-29 nucleotides directly adjacent to the second region, the third region having a third sequence; and a fourth region of 2 nucleotides at the 3' end of the single-stranded RNA molecule, directly adjacent to the third region, the fourth region having a fourth sequence, wherein: (a) the first region has the same number of nucleotides as the third region, (b) the third sequence is the reverse-complement of the first sequence, (c) the third region is complementary to contiguous nucleotides in a target mammalian mRNA sequence, the mRNA sequence being selected from the group consisting of SEQ ID NO: 482-486 and 748-765, and (d) the single-stranded RNA molecule is configured to form a stem loop structure, the first region base pairing with the third region to form a stem, the second region forming a loop, and the fourth region forming a 3' overhang.

As noted above, increased CD47 expression has been observed in fibrotic fibroblast cells, and blocking CD47 reverses fibrosis by increasing phagocytosis of profibrotic fibroblasts and by eliminating suppressive effects on adaptive immunity. In addition to CD47, expression of the genes listed in Table 3 has been associated with the promotion of fibrosis. Reducing the expression of these genes using shRNA-mediated RNAi is also useful in the treatment of fibrotic diseases. Such genes, and their mRNA transcripts, are listed in Table 3. Thus, the transcripts of the genes listed in Table 3 also represent key targets for the treatment of fibrotic diseases using shRNA-mediated RNAi.

Accordingly, in some embodiments, an API useful for the treatment of fibrotic disease in a mammal is shRNA, the shRNA being a single-stranded RNA molecule of 44-71 nucleotides in length, and having, in a 5' to 3' direction: a first region of 19-29 nucleotides at the 5' end of the single-stranded RNA molecule, the first region having a first sequence; a second region of 4-11 nucleotides directly adjacent to the first region, the second region having a second sequence; a third region of 19-29 nucleotides directly adjacent to the second region, the third region having a third sequence; and a fourth region of 2 nucleotides at the 3' end of the single-stranded RNA molecule, directly adjacent to the third region, the fourth region having a fourth sequence, wherein: (a) the first region has the same number of nucleotides as the third region, (b) the third sequence is the reverse-complement of the first sequence, (c) the third region is complementary to contiguous nucleotides in a target mammalian mRNA sequence, the mRNA sequence being selected from the group consisting of SEQ ID NO: 8-21, 40-43, and 766-770, and (d) the single-stranded RNA molecule is configured to form a stem loop structure, the first region base pairing with the third region to form a stem, the second region forming a loop, and the fourth region forming a 3' overhang.

In some embodiments, an API useful for the treatment of fibrotic disease in a mammal is shRNA, the shRNA being a single-stranded RNA molecule of 44-71 nucleotides in length, and having, in a 5' to 3' direction: a first region of 19-29 nucleotides at the 5' end of the single-stranded RNA molecule, the first region having a first sequence; a second region of 4-11 nucleotides directly adjacent to the first region, the second region having a second sequence; a third region of 19-29 nucleotides directly adjacent to the second region, the third region having a third sequence; and a fourth region of 2 nucleotides at the 3' end of the single-stranded RNA molecule, directly adjacent to the third region, the fourth region having a fourth sequence, wherein: (a) the first region has the same number of nucleotides as the third region, (b) the third sequence is the reverse-complement of the first sequence, (c) the third region is complementary to contiguous nucleotides in a mammalian mRNA sequence, the mRNA sequence being selected from the group consisting of SEQ ID NO: 40-43 and 766-770, and (d) the single-stranded RNA molecule is configured to form a stem loop structure, the first region base pairing with the third region to form a stem, the second region forming a loop, and the fourth region forming a 3' overhang.

MicroRNA ("miRNA")-based therapeutics include miRNAs (and miRNA mimics) and inhibitors of miRNAs ("anti-miRs").

miRNAs are transcribed as single stranded RNA precursors having a stem-loop structure and are subsequently processed in the cytosol by the Dicer enzyme, producing a mature double-stranded product ("mature miRNA product"). These mature miRNA products are thought to have regulatory roles, including RNA silencing and post-transcriptional regulation of gene expression, through their complementarity to mRNA.

Expression of the miRNAs shown in Table 4 is known to be downregulated in various cancers and replenishment of a downregulated miRNA offers a promising therapy for the treatment of cancer.

Accordingly, in some embodiments, an API useful for the treatment of cancer in a mammal is an miRNA selected from the group consisting of SEQ ID NO: 825-844, 849-851, 853, 855, 857, 864, 865, and 867-883.

TABLE 4

Therapeutic Cancer (Cancer Cell) miRNA APIs

| miRNA | miRNA Gene | GenBank cDNA RefSeq Accession | (miRNA) SEQ ID NO |
|---|---|---|---|
| miR-34a | MIR34A | NR_029610.1 | 825 |
| miR-34b | MIR34B | NR_029839.1 | 826 |
| miR-34c | MIR34C | NR_029840.1 | 827 |
| miR-200a | MIR200A | NR_029834.1 | 828 |
| miR-200b | MIR200B | NR_029639.1 | 829 |
| miR-200c | MIR200C | NR_029779.1 | 830 |
| miR-26a-1 | MIR26A1 | NR_029499.1 | 831 |
| miR-506 | MIR506 | NR_030233.1 | 832 |
| miR-520a | MIR520A | NR_030189.1 | 833 |
| miR-520b | MIR520B | NR_030195.1 | 834 |
| miR-520c | MIR520C | NR_030198.1 | 835 |
| miR-520d | MIR520D | NR_030204.1 | 836 |
| miR-520e | MIR520E | NR_030183.1 | 837 |
| miR-520f | MIR520F | NR_030186.1 | 838 |
| miR-520g | MIR520G | NR_030206.1 | 839 |
| miR-520h | MIR520H | NR_030215.1 | 840 |
| miR-15a | MIR15A | NR_029485.1 | 841 |
| miR-15b | MIR15B | NR_029663.1 | 842 |
| miR-16-1 | MIR16-1 | NR_029486.1 | 843 |
| miR-16-2 | MIR16-2 | NR_029525.1 | 844 |
| miR-Let-7a-1 | MIRLET7A1 (LET7A1) | NR_029476.1 | 849 |
| miR-Let-7f-1 | MIRLET7F1 (LET7F1) | NR_029483.1 | 850 |
| miR-Let-7d | MIRLET7D (LET7D) | NR_029481.1 | 851 |
| miR-31 | MIR31 | NR_029505.1 | 853 |
| miR-98 | MIR98 | NR_029513.1 | 855 |
| miR-205 | MIR205 | NR_029622.1 | 857 |
| miR-324 | MIR324 (MIR324-5P) | NR_029896.1 | 864 |
| miR-195 | MIR195 | NR_029712.1 | 865 |
| miR-26a-2 | MIR26A2 | NR_029847.1 | 867 |
| miR-101-1 | MIR101-1 | NR_029516.1 | 868 |
| miR-101-2 | MIR101-2 | NR_029836.1 | 869 |
| miR-145 | MIR145 | NR_029686.1 | 870 |
| miR-331 | MIR331 | NR_029895.1 | 871 |
| miR-29b-1 | MIR29B1 | NR_029517.1 | 872 |
| miR-29b-2 | MIR29B2 | NR_029518.1 | 873 |
| miR-7-1 | MIR7-1 | NR_029605.1 | 874 |
| miR-7-2 | MIR7-2 | NR_029606.1 | 875 |
| miR-7-3 | MIR7-3 | NR_029607.1 | 876 |
| miR-33a | MIR33A | NR_029507.1 | 877 |
| miR-21 | MIR21 | NR_029493.1 | 878 |
| miR-203a | MIR203A | NR_029620.1 | 879 |
| miR-203b | MIR203B | NR_039859.1 | 880 |
| miR-4711 | MIR4711 | NR_039861.1 | 881 |
| miR-4689 | MIR4689 | NR_039838.1 | 882 |
| miR-122 | MIR122 | NR_029667.1 | 883 |

In contrast to miRNA, an antimiR (also known as an "antagomir") is a single stranded antisense oligonucleotide ("ASO") having a sequence that is complementary to the sequence of a region of a target mature miRNA product. Mature miRNA products are short single-stranded RNA molecules that are produced after an miRNA molecule is processed in the cytosol. Typically, two mature miRNA products are produced from an miRNA molecule: a 5p RNA molecule (so named because it is processed from the 5' arm of the duplex formed as the stem of an miRNA), and a 3p RNA molecule (so named because it is processed from the 3' arm of the duplex formed as the stem of an miRNA). The 5p and 3p molecules may base pair with each other to form a duplex, and each molecule may be functional—and indeed, may serve a separate function-within a cell through their complementarity to mRNA. In some instances, an miRNA molecule is processed such that only a single functional mature miRNA product is produced.

By binding to their target mature miRNA product through complementary base pairing, antimiRs are able to block the mature miRNA product from binding to its target, thereby inhibiting the functioning of the mature miRNA product. Using antimiR to inhibit mature miRNA products is referred to as miRNA knockdown. See generally Quemener et al. *Wiley Interdiscip Rev RNA* (5):e1594 (2020), which is hereby incorporated by reference herein in its entirety.

antimiRs are 12-25 nucleotides in length and are complementary to consecutive nucleotides of a target mature miRNA product. Different types of nucleic acids may be used to generate an antimiR. Preferably, the antimiR comprises RNA, as RNA/RNA hybrids are very stable. In addition, antimiR may comprise DNA, or comprise both RNA and DNA nucleotides (referred to herein as a "chimera"). An antimiR should bind with high affinity, through complementary base pairing, to the "seed region" of a mature miRNA product, which spans nucleotides 2-8 from the 5'-end of the mature miRNA product (Lennox et al. *Gene Therapy* 18: 1111-20 (2011), which is hereby incorporated by reference herein in its entirety.)

Over the years, significant improvements in binding affinity, stability, and target modulation effects of antimiRs have been achieved through chemical modifications to the oligonucleotide backbone. An antimiR may therefore be an RNA derivative or a DNA derivative. In some embodiments, the antimiR comprises a modification providing the antimiR with an additional property, for instance resistance to endonucleases and RNaseH, stability (for instance in a bodily fluid), and reduced toxicity. In some embodiments, the modification is a 2'-O-methyl-phosphorothioate oligoribonucleotide modification, a 2'-O-methoxyethyl oligoribonucleotide modification, and combinations thereof. In some embodiments, the antimiR comprises a peptide nucleic acid, locked nucleic acid, or a morpholino phosphorodiamidate. See generally Wahlestedt et al. PNAS 97, 5633-5638 (2000); Elayadi et al. *Curr Opin Investig Drugs* 2, 558-61 (2001); Larsen et al. *Biochim Biophys Acta* 1489, 159-166 (1999); Braasch et al. *Biochemistry* 41, 4503-4510 (2002); Summerton et al. *Antisense Nucleic Acid Drug Dev* 7, 187-195 (1997), each of which is hereby incorporated by reference herein in its entirety.

Expression of the miRNAs shown in Table 5 is known to be upregulated in various cancers and their mature miRNA products, as shown in Table 6, are preferred targets for miRNA knockdown for the treatment of cancer.

Accordingly, in some embodiments, an API useful for the treatment of cancer in a mammal is an antimiR, the antimiR being a single-stranded nucleic acid molecule of 12-25 nucleotides in length, the antimiR having a sequence of 12-25 contiguous nucleotides that is complementary to contiguous nucleotides in a target mature miRNA product sequence, the mature miRNA product sequence being selected from the group consisting of SEQ ID NO: 884-908, wherein the contiguous nucleotides in the mature miRNA product sequence includes, in a 5' to 3' direction, nucleotides 2 to 8 of the mature miRNA product sequence.

TABLE 5

Upregulated miRNA Expression in Cancer

| miRNA Gene | GenBank cDNA RefSeq Accession | miRNA | (miRNA) SEQ ID NO |
|---|---|---|---|
| MIR10B | NR_029609.1 | miR-10b | 845 |
| MIR221 | NR_029635.1 | miR-221 | 846 |
| MIR155 | NR_030784.1 | miR-155 | 847 |
| MIR630 | NR_030359.1 | miR-630 | 848 |
| MIR27A | NR_029501.1 | miR-27a | 852 |
| MIR96 | NR_029512.1 | miR-96 | 854 |
| MIR182 | NR_029614.1 | miR-182 | 856 |
| MIR93 | NR_029510.1 | miR-93 | 858 |
| MIR375 | NR_029867.1 | miR-375 | 859 |
| MIR25 | NR_029498.1 | miR-25 | 860 |
| MIR106B | NR_029831.1 | miR-106b | 861 |
| MIR512-1 | NR_030180.1 | miR-512-1 | 862 |
| MIR512-2 | NR_030181.1 | miR-512-2 | 863 |
| MIR18A | NR_029488.1 | miR-18a | 866 |

TABLE 6 antimiR Cancer (Cancer Cell) Target Mature miRNA Products

| miRNA | Mature miRNA Product | (Mature miRNA Product) SEQ ID NO |
|---|---|---|
| miR-10b | hsa-miR-10b-5p | 884 |
|  | hsa-miR-10b-3p | 885 |
| miR-221 | hsa-miR-221-5p | 886 |
|  | hsa-miR-221-3p | 887 |
| miR-155 | hsa-miR-155-5p | 888 |
|  | hsa-miR-155-3p | 889 |
| miR-630 | hsa-miR-630 | 890 |
| miR-27a | hsa-miR-27a-5p | 891 |
|  | hsa-miR-27a-3p | 892 |
| miR-96 | hsa-miR-96-5p | 893 |
|  | hsa-miR-96-3p | 894 |
| miR-182 | hsa-miR-182-5p | 895 |
|  | hsa-miR-182-3p | 896 |
| miR-93 | hsa-miR-93-5p | 897 |
|  | hsa-miR-93-3p | 898 |
| miR-375 | hsa-miR-375-5p | 899 |
|  | hsa-miR-375-3p | 900 |
| miR-25 | hsa-miR-25-5p | 901 |
|  | hsa-miR-25-3p | 902 |
| miR-106b | hsa-miR-106b-5p | 903 |
|  | hsa-miR-106b-3p | 904 |
| miR-512-1 | hsa-miR-512-5p | 905 |
|  | hsa-miR-512-5p | 906 |
| miR-512-2 | hsa-miR-512-5p | 905 |
|  | hsa-miR-512-5p | 906 |
| miR-18a | hsa-miR-18a-5p | 907 |
|  | hsa-miR-18a-3p | 908 |

In other embodiments, an API useful for the treatment of cancer in a mammal is a protein having anti-cancer properties. Anti-cancer properties include inhibiting the proliferation of a cancer cell, inhibiting the proliferation of a tumor, causing the death of a cancer cell, reducing the size of a tumor, or causing the elimination of a tumor. The proteins listed in Table 7 possess anti-cancer properties. Accordingly, a protein having an amino acid sequence selected from the group consisting of SEQ ID NO: 909-929 and homologs thereof is a suitable APIs for use in accordance with embodiments of the invention. In other embodiments, a protein consisting of an amino acid sequence selected from the group consisting of SEQ ID NO: 909-929 and homologs thereof is a suitable APIs for use in accordance with embodiments of the invention.

In some embodiments, an API suitable for the treatment of cancer in a mammal is an mRNA encoding an amino acid sequence selected from the group consisting of SEQ ID NO: 909-929 and homologs thereof, the mRNA being configured to be translated in a target cell of the mammal to produce a protein comprising the amino acid sequence. In other embodiments, an API suitable for the treatment of cancer in a mammal is an mRNA encoding an amino acid sequence selected from the group consisting of SEQ ID NO: 909-929 and homologs thereof, the mRNA being configured to be translated in a target cell of the mammal to produce a protein consisting of the amino acid sequence. The mRNA may be codon-optimized for translation in the target cell of the mammal.

TABLE 7

Therapeutic Cancer (Cancer Cell) Protein APIs

| Protein | SEQ ID NO |
|---|---|
| Cyclin-dependent kinase 9 (CDK9) | 909 |
| Histidine-rich glycoprotein (HRG) | 910 |
| Interferon alpha-2 (IFNA2) | 911 |
| Interferon beta (IFNB1) | 912 |
| Interferon gamma (IFNG) | 913 |
| Interferon lambda-2 (IFNL2) | 914 |
| Interferon lambda-3 (IFNL3) | 915 |
| Interleukin-27 subunit alpha (IL27) | 916 |
| Interleukin-27 subunit beta (EBI3) | 917 |
| Guanylate kinase (GUK1) | 918 |
| LanC-like protein 2 (LANCL2) | 919 |
| GATOR complex protein NPRL2 (NPRL2) | 920 |
| Solute carrier family 22 member 2 (SLC22A2) | 921 |
| Equilibrative nucleoside transporter 1 (SLC29A1) | 922 |
| Beclin-1 (BECN1) | 923 |
| FK506-binding protein-like (FKBPL) | 924 |
| Ribonuclease pancreatic (RNASE1) | 925 |
| Probable global transcription activator SNF2L2 (SMARCA2) | 926 |
| Metalloproteinase inhibitor 3 (TIMP3) | 927 |
| Tumor necrosis factor ligand superfamily member 10 (TNFSF10) | 928 |
| Collagen alpha-1(XVIII) chain (COL18A1) | 929 |

Example 1: VSIRPα-siRNA Conjugate Binds Red Blood Cells

FAM-tagged siRNA (FIG. 1A) (SEQ TD NO:965 (sense strand) and SEQ TD NO:966 (antisense strand)) was mixed with vSIRPα at a 1:1 molar ratio (50 pmol of vSIRPα and 50 pmol siRNA). The siRNA was modified at its 3' end with maleimide. The vSIRPα was designed with cysteine near its C-terminus. Thiol from the cysteine and maleimide were reacted at a neutral pH via click chemistry. The reaction was held overnight in 4° C. shaker, resulting in the vSIRPα-siRNA conjugate shown in FIG. 1A.

The vSIRPα-siRNA conjugate was isolated using a NAP-5 column using the manufacturer's protocol.

To assess the ability of the vSIRPα-siRNA conjugate to bind red blood cells ("RBC"), the vSIRPα-siRNA conjugate was mixed with mouse RBC, as depicted in FIG. 1B. For this experiment, 6×10⁶ red blood cells, in a volume of 2 µl phosphate-buffered saline ("PBS"), were mixed with 2.5 µl of PBS containing the vSIRPα-siRNA conjugate (totaling 50 pmol of the vSIRPα-siRNA conjugate) and 5.5 µl of PBS.

A negative control was made by mixing 6×10⁶ red blood cells, in a volume of 2 µl PBS, with 8 µl of PBS. Each mixture was then incubated at room temperature (20-25° C.) for 2 hours (FIG. 1B).

After the incubation, 5 µl of each mixture was diluted 20-fold with PBS, for a total volume of 100 µl for each mixture, and each dilution was placed in a glass-bottom dish and fluorescently imaged at 494-567 nm with a microscope (488 nm excitation wavelength).

As can be seen in FIG. 1C, the negative control shows no fluorescence, whereas the mixture containing the vSIRPα-siRNA conjugate shows a strong fluorescence signal associated with the red blood cells, indicating that the vSIRPα-siRNA conjugate binds RBC.

Example 2: vSIRPα-siRNA Conjugate is Transferred from RBC to Cancer Cells as Demonstrated by Flow Cytometry 500 pmol of the vSIRPα-siRNA conjugate from Example 1 was incubated with 5×10³ mouse RBC in Dulbecco's phosphate-buffered saline ("DPBS") at a total volume of 20 µl for 30 min at room temperature (20-25° C.).

After 30 min, the mixture was washed with DPBS by centrifugation at 500×g for 10 minutes and the supernatant was removed. The RBC bound with the vSIRPα-siRNA conjugate were then resuspended to 20 µl PBS.

Two cell lines were used, CT26.CL25 (ATCC CRL-2639) and CaCO2 (ATCC HTB-37). CT26.CL25 is a mouse colon carcinoma cell line. CaCO2 is a human colorectal adenocarcinoma cell line that is deficient in expressing CD47, and was thus used as a negative control (Liu et al. *J Biol Chem* 276(43):40156-66 (2001), which is hereby incorporated by reference herein in its entirety).

Each cell line, grown independently in a cell culture dish, was detached from the dish with trypsin-EDTA. The cells from each dish were then washed with DPBS, counted, and diluted to 10⁵ cells/100 µl PBS. 4 µl of the FAM-vSIRPα-siRNA/RBC resuspension (totaling 10³ RBC and 100 pmol of the vSIRPα-siRNA) was mixed, independently, with each 100 µl dilution of CT26.CL25 cells and CaCO2 cells. Each mixture was incubated for 30 minutes at room temperature (20-25° C.).

After 30 minutes, each mixture was centrifuged, and the supernatants were removed. The cell pellets were resuspended with 200 µl of flow cytometry buffer for flow cytometer analysis.

Figure 2B:
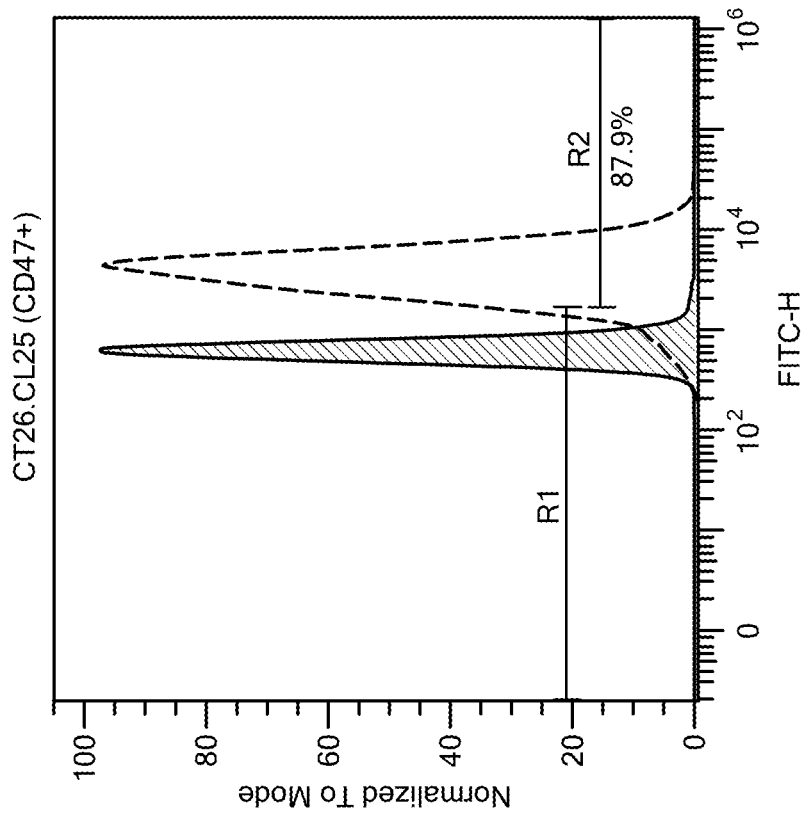
FIG. 2B shows flow cytometry results of CT26.CL25 cells before and after being incubated with red blood cells bound with FAM-tagged vSIRPα-siRNA.
Figure 2A:
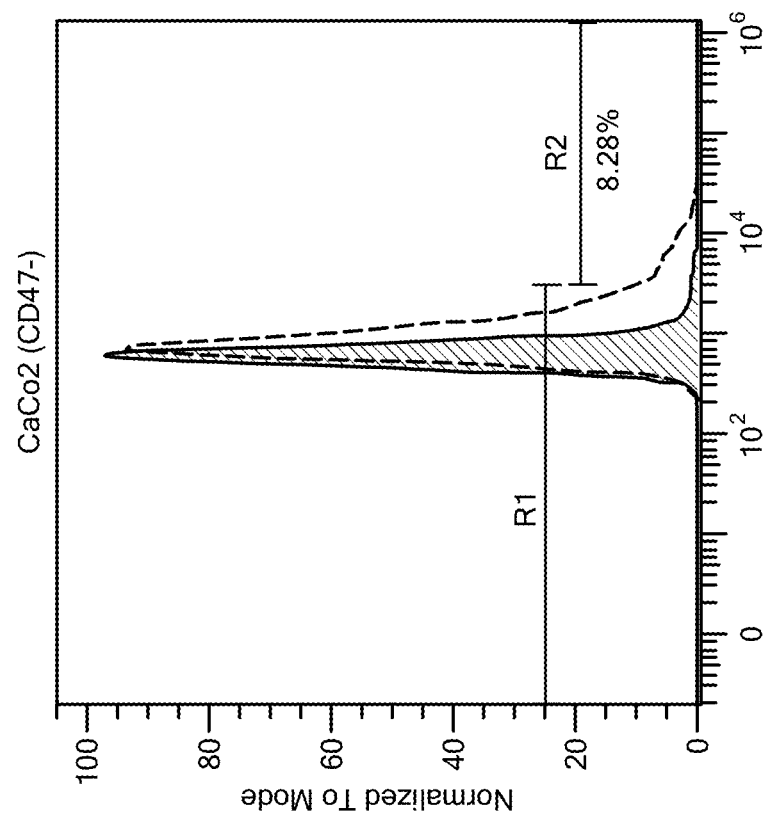
FIG. 2A shows flow cytometry results of CaCO2 cells before and after being incubated with red blood cells bound with FAM-tagged vSIRPα-siRNA, in accordance with embodiments of the invention.

FIGS. 2A and 2B show flow cytometry results for CaCO2 cells and CT26.CL25 cells, respectively. Flow cytometry was conducted using a 488 nm laser for excitation of the FAM tag, and detected at 525-565 nm wavelength. After the incubation with RBCs bound with FAM-tagged vSIRPα-siRNA, each cancer cell line showed different levels of a shift in florescence. These results show a significant fluorescence shift for CT26.CL25 after incubation with RBC and little shift for CaCO2 after incubation with RBC, indicating that the degree of fluorescence shift is dependent on the level of CD47 on the cancer cells. These results strongly suggest that FAM-tagged vSIRPα-siRNA has been transferred from RBC to CD47 present on the surface of the CT26.CL25 cells.

Example 3: Anti-CD47 Antibody is Transferred from RBC to Cancer Cells as Demonstrated by Flow Cytometry First, 0.1 µg of Alexa Fluor® 647 anti-mouse CD47 monoclonal antibody (Biolegend, #127510) was incubated with 4×10³ mouse RBC in a total volume of 100 μl DPBS for 30 minutes at room temperature. After incubation, the RBC-antibody mixture was centrifuged at 500 g for 5 minutes. The supernatant was then decanted and the cells resuspended in 20 μl DPBS.

We then mixed 2×10⁵ CT26.CL25 cells (in 100 μl DPBS) with 10 μl of the resuspended RBC-antibody mixture, for a total volume of 110 μl (mixture #1). Similarly, 2×10⁵ CaCO2 cells (in 100 μl DPBS) were mixed with 10 μl of the resuspended RBC-antibody mixture, for a total volume of 110 μl (mixture #2).

Mixture #1 and mixture #2 were incubated for 30 minutes at room temperature. After incubation, 1 ml of DPBS was added to each mixture, followed by centrifugation at 500 g for 5 minutes. For each mixture, after centrifugation, the supernatant was decanted, and the remaining cells were resuspended in 100 μl DPBS and subject to flow cytometry (Beckman, laser 488 nm, detected 650-670 nm).

FIGS. 3A and 3B show these flow cytometry results for CaCO2 cells and CT26.CL25 cells, respectively. Although not as pronounced as the fluorescence shift observed in Example 2, a greater fluorescence shift was observed for CT26.CL25 cells after incubation with RBC compared to the fluorescence shift for CaCO2 cells after incubation with RBC. This, again, indicates that the degree of fluorescence shift is dependent on the level of CD47 on the cancer cells. These results suggest that the Alexa Fluor® 647 anti-mouse CD47 monoclonal antibody was transferred from RBC to CD47 present on the surface of the CT26.CL25 cells.

Example 4: vSIRPα-siRNA Conjugate is Transferred from RBC to Cancer Cells as Demonstrated by Flow Cytometry The vSIRPα-siRNA-FAM conjugate of Example 1 was further tested for its ability to be transferred from RBC to CD47 present on the surface of CT26.CL25 cells. Experiments were carried out as in Example 2, except that 100 pmol of the conjugate, rather than 500 pmol, was incubated with the RBC.

Figure 4:
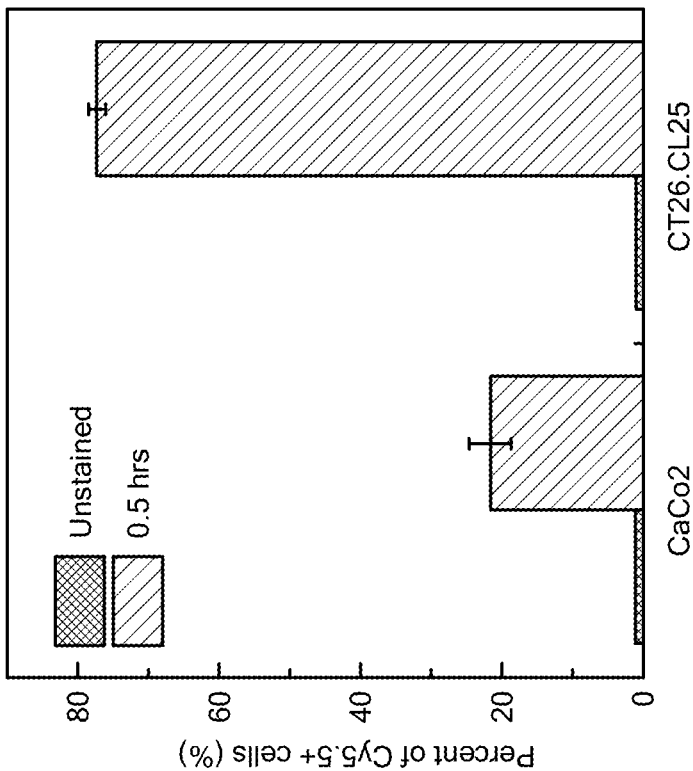
FIG. 4 shows flow cytometry results of CaCO2 cells and CT26.CL25 cells before ("unstained") and after being incubated with red blood cells bound with FAM-tagged vSIRPα-siRNA, in accordance with embodiments of the invention.

As shown in the flow cytometry results of FIG. 4, a significantly greater percentage of CT26.CL25 cells demonstrate FAM fluorescence compared to CaCO2 cells, again, strongly suggesting that FAM-tagged vSIRPα-siRNA has been transferred from RBC to CD47 present on the surface of the CT26.CL25 cells.

Example 5: Cy5.5-labeled vSIRPα is Transferred from RBC to Cancer Cells as Demonstrated by Flow Cytometry vSIRPα labeled with Cy5.5 was tested for its ability to be transferred from RBC to CD47 present on the surface of CT26.CL25 cells. Experiments were carried out as in Example 2, except that 200 pmol of the labeled vSIRPα, rather than 500 pmol of conjugate, was incubated with the RBC.

Figure 5:
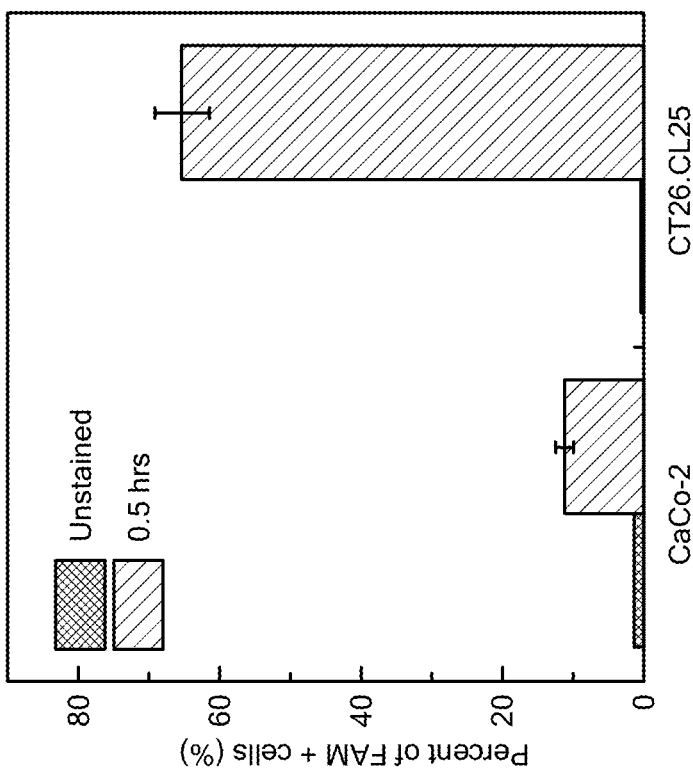
FIG. 5 shows flow cytometry results of CaCO2 cells and CT26.CL25 cells before ("unstained") and after being incubated with red blood cells bound with Cy5.5-labeled vSIRPα, in accordance with embodiments of the invention.

As shown in the flow cytometry results of FIG. 5, a significantly greater percentage of CT26.CL25 cells demonstrate Cy5.5 fluorescence compared to CaCO2 cells, strongly suggesting that vSIRPα labeled with Cy5.5 has been transferred from RBC to CD47 present on the surface of the CT26.CL25 cells.

Example 6: Anti-CD47 Antibody is Transferred from RBC to Cancer Cells as Demonstrated by Flow Cytometry An anti-mouse CD47 monoclonal antibody (Biolegend, #127510) labeled with Alexa Flour® 647 was tested for its ability to be transferred from RBC to CD47 present on the surface of CT26.CL25 cells. Experiments were carried out as in Example 3, except that 1 μg of the labeled antibody, rather than 0.1 μg, was incubated with the RBC.

Figure 6:
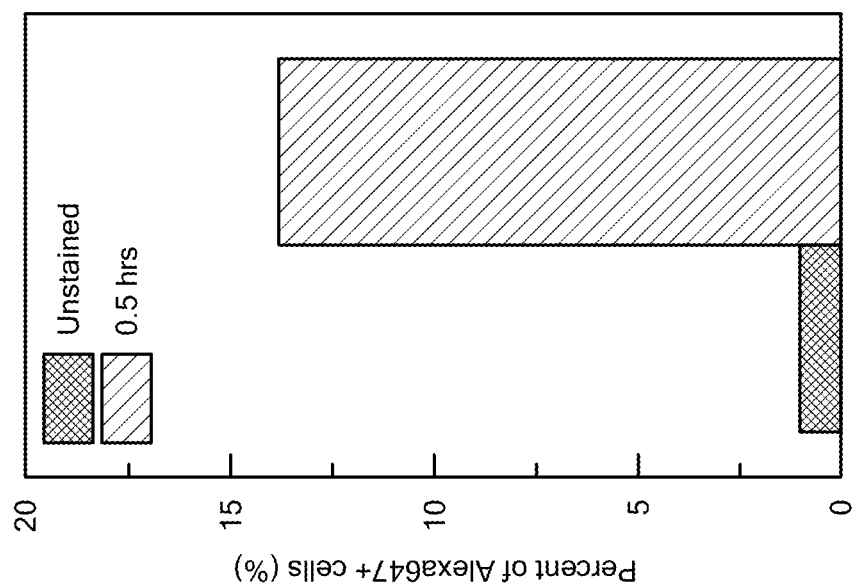
FIG. 6 shows flow cytometry results of CT26.CL25 cells before ("unstained") and after being incubated with red blood cells bound with an Alexa Fluor® 647 anti-mouse CD47 monoclonal antibody, in accordance with embodiments of the invention.

As shown in the flow cytometry results of FIG. 6, a significantly greater percentage of CT26.CL25 cells demonstrate Alexa Fluor® 647 fluorescence compared to unstained cells, strongly suggesting that the anti-CD47 antibody conjugated to Alexa Flour® 647 has been transferred from RBC to CD47 present on the surface of the CT26.CL25 cells. This experiment also demonstrates that monoclonal antibodies against CD47 are capable of being transferred from RBC to CD47 present on the surface of cancer cells.

Example 7: An Antibody-miR21 Conjugate is Transferred from RBC to Cancer Cells as Demonstrated by Flow Cytometry An anti-CD47 monoclonal antibody (Bioxcell, #BE0270) conjugated to Cy5 labeled miR21 (SEQ ID NO:878) was tested for its ability to be transferred from RBC to CD47 present on the surface of CT26.CL25 cells. Experiments were carried out as in Example 3, except that 15.8 μg of the antibody conjugate, rather than 0.1 μg, was incubated with the RBC.

Figure 7:
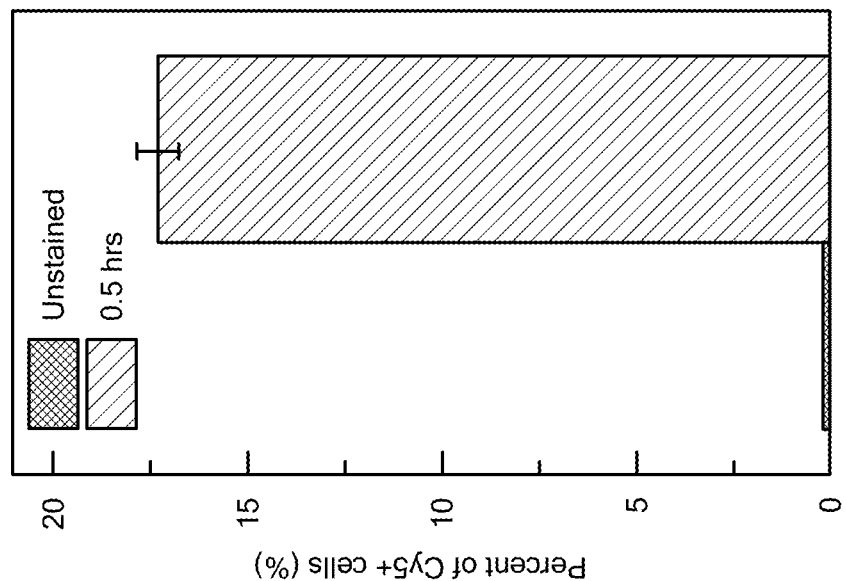
FIG. 7 shows flow cytometry results of CT26.CL25 cells before ("unstained") and after being incubated with red blood cells bound with a CD47mAb-miR21-Cy5 conjugate, in accordance with embodiments of the invention.

As shown in the flow cytometry results of FIG. 7, a greater percentage of CT26.CL25 cells demonstrate Cy5 fluorescence compared to unstained cells, strongly suggesting that the CD47mAb-miR21-Cy5 conjugate has been transferred from RBC to CD47 present on the surface of the CT26.CL25 cells.

Example 8: Thrombospondin-1 is Transferred from RBC to Cancer Cells as Demonstrated by Flow Cytometry Thrombospondin-1 (TSP-1) is a matricellular protein that inhibits angiogenesis and endothelial cell proliferation. TSP-1 binds CD47. The TSP-1 signaling pathway has been found to be involved in various conditions, such as renal disease, cardiovascular disease, inflammation, and cancer. The underlying mechanisms and pathways for TSP-1 are yet to be fully elucidated. However, the function of TSP-1 on several key receptors CD36/VEGF and CD47 has been demonstrated. Especially in cancer, the activated TSP-1 and CD47 pathway has been found to reduce tumor growth and metastasis. See Kale et al. Int J Mol Sci, 22(8) (2021) and Kaur et al. J Biol Chem, 285(50), 38923-38932 (2010). Here, we show that a labeled murine TSP-1 is transferred from RBC to the CT26.CL25 cancer cells.

Murine TSP-1 (7859-TH, R&D Systems) labeled with Cy5.5 was tested for its ability to be transferred from RBC to CD47 present on the surface of CT26.CL25 cells. Experiments were carried out as in Example 2, except that 5 μg of Cy5.5 labeled TSP-1, rather than 500 pmol of conjugate, was incubated with the RBC.

Figure 8:
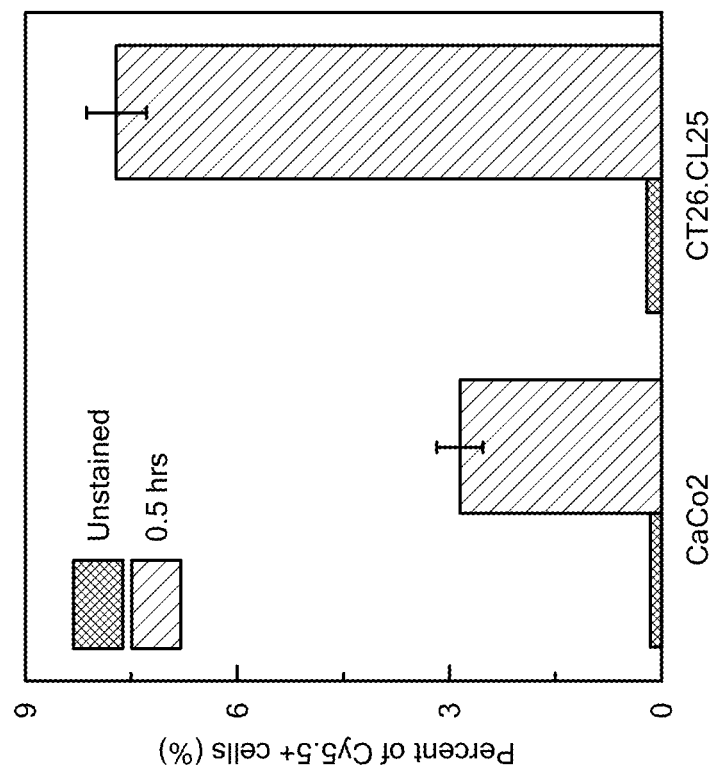
FIG. 8 shows flow cytometry results of CaCO2 cells and CT26.CL25 cells before ("unstained") and after being incubated with red blood cells bound with Cy5.5-labeled murine thrombospondin-1, in accordance with embodiments of the invention.

As shown in the flow cytometry results of FIG. 8, a significantly greater percentage of CT26.CL25 cells demonstrate Cy5.5 fluorescence compared to CaCO2 cells, strongly suggesting that Cy5.5-labeled TSP-1 has been transferred from RBC to CD47 present on the surface of the CT26.CL25 cells.

Example 9: vSIRPα-siRNA Conjugate Binds RBC In Vivo 5 nmol of the vSIRPα-siRNA conjugate from Example 1 and 5 nmol of unconjugated siRNA from Example 1 were each stained with the intercalating dye YOYO™_1 Iodide in a molar ratio of 1:1 in a total volume of 120 µl of RNAse-free water. After incubation for 30 minutes at room temperature, the stained conjugate and siRNA were injected into mice as detailed below.

Three Balb/c mice were used for the experiment: one untreated mouse was used as a negative control; one mouse was injected intravenously at the tail vein with 5 nmol of the unconjugated stained siRNA, and one mouse was injected intravenously at the tail vein with 5 nmol of the stained of the vSIRPα-siRNA conjugate.

45 minutes after injection, blood was collected from the mice. 50 µl of whole blood from each sample was washed twice with 1 ml of DPBS by centrifugation at 500×g for 10 minutes and resuspended in DPBS. The resuspended blood was imaged via confocal microscopy using confocal dishes (SPL 100350) and RBC-associated YOYO™-1 Iodide fluorescence signals were compared between different groups (control, siRNA, and conjugate). A 488 nm laser was used (YOYO™-1 Iodide has an excitation wavelength of 491 nm).

Figure 9:
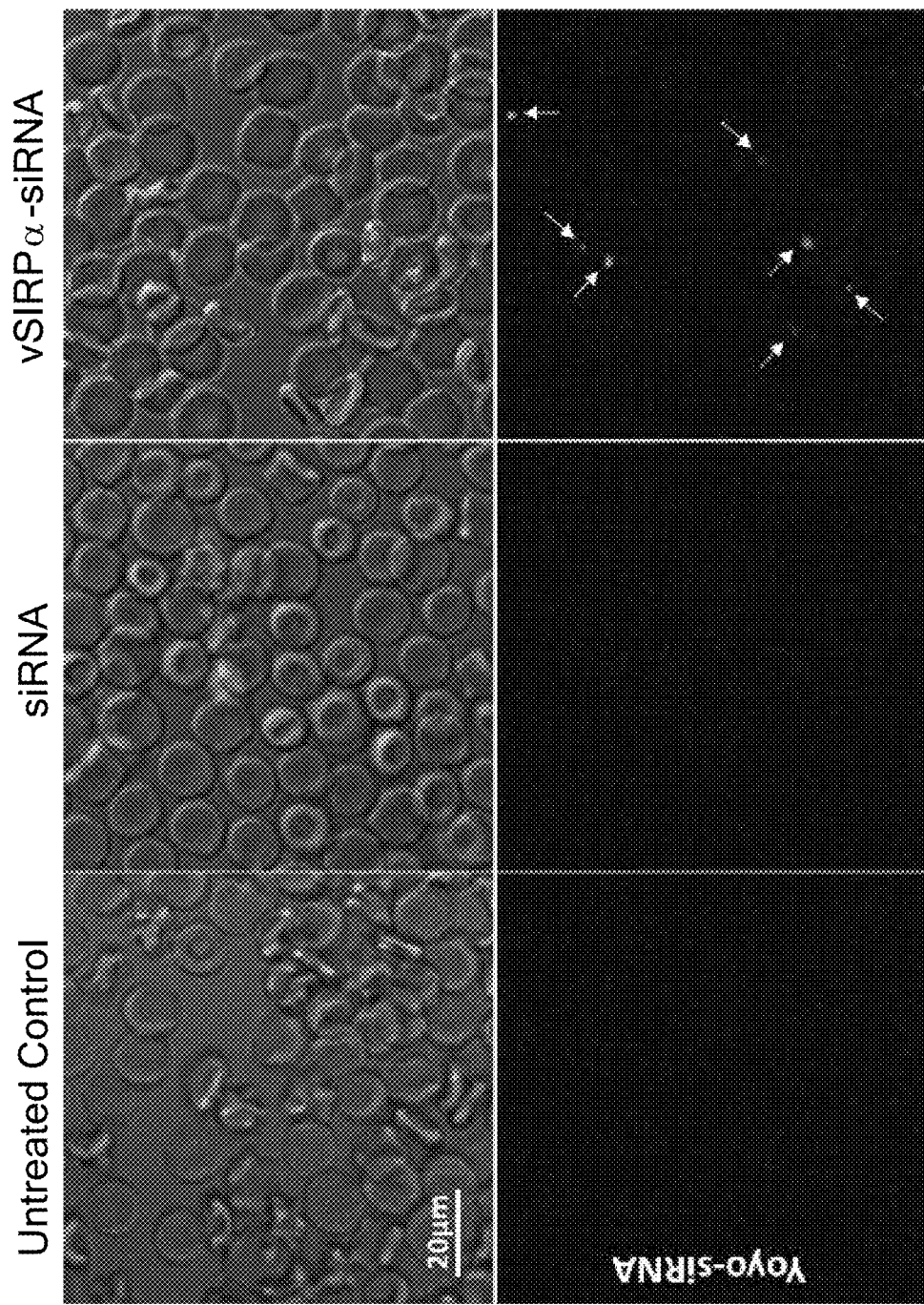
FIG. 9 shows red blood cells isolated from an untreated mouse, a mouse injected with a fluorescently labeled siRNA conjugate, and a mouse injected with a fluorescently labeled vSIRPα-siRNA conjugate, in accordance with embodiments of the invention.

As shown in FIG. 9, RBCs from the mouse injected with the vSIRPα-siRNA conjugate shows fluorescent punctate (arrows of FIG. 9), indicating that binding between the vSIRPα-siRNA conjugate and RBCs occurs in vivo.

Potential Claims

Various embodiments of the present invention may be characterized by the potential claims listed in the paragraphs following this paragraph (and before the actual claims provided at the end of this application). These potential claims form a part of the written description of this application. Accordingly, subject matter of the following potential claims may be presented as actual claims in later proceedings involving this application or any application claiming priority based on this application. Inclusion of such potential claims should not be construed to mean that the actual claims do not cover the subject matter of the potential claims. Thus, a decision to not present these potential claims in later proceedings should not be construed as a donation of the subject matter to the public.

Without limitation, potential subject matter that may be claimed (prefaced with the letter "P" so as to avoid confusion with the actual claims presented below) includes:

P1. A therapeutic compound for RBC-mediated delivery in a mammalian subject to a target cell expressing CD47, the therapeutic compound comprising:
  a CD47-binding protein conjugated to an API so as to form a conjugate;
  wherein the CD47-binding protein is selected from the group consisting of wild type SIRPα (SEQ ID NO: 1), vSIRPα (SEQ ID NO: 3), wild type thrombospondin-1 (TSP-1) (SEQ ID NO: 7), wild type SIRPγ (SEQ ID NO: 4), vSIRPγ-1 (SEQ ID NO: 5), vSIRPγ-2 (SEQ ID NO: 6), ALX148 (SEQ ID NO: 962), TTI-661 (SEQ ID NO: 963), TTI-662 (SEQ ID NO: 964), a homolog of any of the foregoing, and combinations thereof, and is configured to bind the conjugate to CD47 of a red blood cell of the subject so as to enable transport of the conjugate, through the subject's circulatory system, to the target cell, so that (i) the CD47-binding protein, being configured to bind the conjugate to the CD47 of the red blood cell, binds the CD47 of the target cell, thus transferring the conjugate from the red blood cell to the target cell so as to form a conjugate-CD47 complex on the target cell, thereby blocking CD47 and inhibiting CD47 activity as an immune escape mechanism of the target cell, and (ii) the conjugate is taken up by the target cell via endocytosis of the conjugate-CD47 complex, thereby further inhibiting the immune escape mechanism of the target cell and delivering the API into the target cell.

P2. A therapeutic compound for RBC-mediated delivery in a mammalian subject to a target cell expressing CD47, the therapeutic compound comprising:
  a CD47-binding protein conjugated to an API so as to form a conjugate;
  wherein the CD47-binding protein is selected from the group consisting of wild type thrombospondin-1 (TSP-1) (SEQ ID NO: 7), wild type SIRPγ (SEQ ID NO: 4), vSIRPγ-1 (SEQ ID NO: 5), vSIRPγ-2 (SEQ ID NO: 6), ALX148 (SEQ ID NO: 962), TTI-661 (SEQ ID NO: 963), TTI-662 (SEQ ID NO: 964), a homolog of any of the foregoing, and combinations thereof, and is configured to bind the conjugate to CD47 of a red blood cell of the subject so as to enable transport of the conjugate, through the subject's circulatory system, to the target cell, so that (i) the CD47-binding protein, being configured to bind the conjugate to the CD47 of the red blood cell, binds the CD47 of the target cell, thus transferring the conjugate from the red blood cell to the target cell so as to form a conjugate-CD47 complex on the target cell, thereby blocking CD47 and inhibiting CD47 activity as an immune escape mechanism of the target cell, and (ii) the conjugate is taken up by the target cell via endocytosis of the conjugate-CD47 complex, thereby further inhibiting the immune escape mechanism of the target cell and delivering the API into the target cell.

P3. A therapeutic compound for RBC-mediated delivery in a mammalian subject to a target cell expressing CD47, the therapeutic compound comprising:
  a CD47-binding protein conjugated to an API so as to form a conjugate;
  wherein the CD47-binding protein is an anti-CD47 antibody, the anti-CD47 antibody comprising:
  (a) a heavy chain variable region including complementarity determining regions CDR1, CDR2, and CDR3 comprising SEQ ID NO: 932, SEQ ID NO: 933, and SEQ ID NO: 934, respectively, and a light chain variable region including complementarity determining regions CDR1, CDR2, and CDR3 comprising SEQ ID NO: 935, SEQ ID NO: 936, and SEQ ID NO: 937, respectively;
  (b) a heavy chain variable region including complementarity determining regions CDR1, CDR2, and CDR3 comprising SEQ ID NO: 940, SEQ ID NO: 941, and SEQ ID NO: 942, respectively, and a light chain variable region including complementarity determining regions CDR1, CDR2, and CDR3 comprising SEQ ID NO: 943, SEQ ID NO: 944, and SEQ ID NO: 945, respectively;
  (c) a heavy chain variable region including complementarity determining regions CDR1, CDR2, and CDR3 comprising SEQ ID NO: 948, SEQ ID NO: 949, and SEQ ID NO: 950, respectively, and a light chain variable region including complementarity determining regions CDR1, CDR2, and CDR3 comprising SEQ ID NO: 951, SEQ ID NO: 952, and SEQ ID NO: 953, respectively; or
  (d) a heavy chain variable region including complementarity determining regions CDR1, CDR2, and CDR3 comprising SEQ ID NO: 956, SEQ ID NO: 957, and SEQ ID NO: 958, respectively, and a light chain variable region including complementarity determining regions CDR1, CDR2, and CDR3 comprising SEQ ID NO: 959, SEQ ID NO: 960, and SEQ ID NO: 961, respectively; and being configured to bind the conjugate to CD47 of a red blood cell of the subject so as to enable transport of the conjugate, through the subject's circulatory system, to the target cell, so that (i) the CD47-binding protein, being configured to bind the conjugate to the CD47 of the red blood cell, binds the CD47 of the target cell, thus transferring the conjugate from the red blood cell to the target cell so as to form a conjugate-CD47 complex on the target cell, thereby blocking CD47 and inhibiting CD47 activity as an immune escape mechanism of the target cell, and (ii) the conjugate is taken up by the target cell via endocytosis of the conjugate-CD47 complex, thereby further inhibiting the immune escape mechanism of the target cell and delivering the API into the target cell.

P3.5 The therapeutic compound according to claim P3, wherein the anti-CD47 antibody is a humanized antibody.

P4. The therapeutic compound according to any one of the preceding claims, wherein the CD47-binding protein is conjugated to the API by a bond selected from the group consisting of a covalent bond, a hydrogen bond, an ionic bond, a van der Waals interaction, and combinations thereof.

P5. The therapeutic compound according to any one of the preceding potential claims, wherein the CD47-binding protein is conjugated to the API by a linker.

P6. The therapeutic compound according to claim P5, wherein the linker is cleavable.

P7. The therapeutic compound according to any one of claims P5 and P6, wherein the linker is configured to be cleaved by a lysosomal degradative enzyme.

P8. The therapeutic compound according to any one of the preceding potential claims, wherein the API is selected from the group consisting of RNA, DNA, an RNA derivative, a DNA derivative, a protein, and a small molecule.

P9. The therapeutic compound according to any one of claims P1-P7, wherein the API is selected from the group consisting of siRNA, shRNA, miRNA, antimiR, and mRNA.

P10. The therapeutic compound according to any one of the preceding potential claims, wherein the target cell is a cell selected from the group consisting of a cancer cell, a virus infected cell, a fibrotic cell, and combinations thereof.

P11. The therapeutic compound according to any one of claims P1-P9, wherein the target cell is a cancer cell.

P12. The therapeutic compound according to any one of claims P1-P9, wherein the target cell is a virus-infected cell.

P13. The therapeutic compound according to any one of claims P1-P9, wherein the target cell is a fibrotic cell.

P14. The therapeutic compound according to claim P11, wherein the cancer cell is in a tumor attributable to a cancer selected from the group consisting of brain tumor, spinal cord tumor, retinoblastoma, oral cancer, nasal cavity cancer, paranasal sinus cancer, pharyngeal cancer, laryngeal cancer, neck cancer, head and neck cancer, melanoma, skin cancer, breast cancer, thyroid cancer, malignant adrenal tumor, endocrine cancer, lung cancer, pleural tumor, respiratory tract cancer, esophageal cancer, stomach cancer, small intestine cancer, colon cancer, anal cancer, liver cancer, biliary tract cancer, pancreatic cancer, kidney cancer, bladder cancer, prostate cancer, testicular cancer, penile cancer, cervical cancer, endometrial cancer, choriocarcinoma, ovarian cancer, blood cancer including acute/chronic leukemia, malignant lymphoma and multiple myeloma, bone tumor, soft tissue tumor, childhood leukemia, and childhood cancer.

P15. The therapeutic compound according to claim P11, wherein the cancer cell is attributable to a cancer selected from the group consisting of ovarian serous cystadenocarcinoma, lung adenocarcinoma, cervical and endocervical cancer, head and neck squamous cell carcinoma, thyroid carcinoma, uterine corpus endometrioid carcinoma, prostate adenocarcinoma, mesothelioma, diffuse large B-cell lymphoma, acute leukemia, lung squamous cell carcinoma, acute lymphoblastic leukemia, esophageal carcinoma, myxofibrosarcoma, pancreatic adenocarcinoma, rectum adenocarcinoma, colon adenocarcinoma, acute megakaryoblastic leukemia, breast invasive carcinoma, stomach adenocarcinoma, bladder urothelial carcinoma, cholangiocarcinoma, leukemia, thymic carcinoma, leiomyosarcoma, thymoma, undifferentiated pleomorphic sarcoma, uterine carcinosarcoma, acute myeloid leukemia, glioblastoma multiforme, sarcoma, skin cutaneous melanoma, kidney clear cell carcinoma, dedifferentiated liposarcoma, lymphoma, retinoblastoma, neuroblastoma, osteosarcoma, juvenile myelomonocytic leukemia, gastrointestinal stromal tumor, dysembryoplatic neuroepithelial tumor, adrenocortical cancer, acute leukemia of ambiguous lineage, pheochromocytoma and paraganglioma, glioma, testicular germ cell tumor, supratentorial embryonal tumor NOS, neurofibroma, kidney papillary cell carcinoma, hepatocellular carcinoma, kidney chromophobe, malignant peripheral nerve sheath tumor, ependymoma, adrenocortical carcinoma, nasopharyngeal carcinoma, spindle cells/sclerosing rhabdomyosarcoma, melanoma, choroid plexus carcinoma, undifferentiated spindle cell carcinoma, myoepithelial carcinoma, alveolar rhabdomyosarcoma, rhabdomyosarcoma, atypical teratoid/rhabdoid tumor, desmoplastic small round cell tumor, fibromatosis, synovial sarcoma, wilms tumor, myofibromytosis, fibrolamellar hepatocellular carcinoma, undifferentiated sarcoma NOS, embryonal rhabdomyosarcoma, uveal melanoma, Ewing sarcoma, hepatoblastoma, infantile fibrosarcoma, INI-deficient soft tissue sarcoma NOA, undifferentiated hepatic sarcoma, and medulloblastoma.

P16. The therapeutic compound according to claim P12, wherein the virus-infected cell is infected with a SARS-CoV-2 virus.

P17. The therapeutic compound according to claim P13, wherein the fibrotic cell is associated with cystic fibrosis.

P18. The therapeutic compound according to any one of claims P1-P7, P10, P11, P14, and P15, wherein the API is siRNA, the siRNA being a double-stranded RNA molecule including an antisense RNA strand and a sense RNA strand, wherein:

(a) the antisense RNA strand is 19-29 nucleotides in length and is complementary to contiguous nucleotides in a target mammalian mRNA sequence, the mRNA sequence being selected from the group consisting of SEQ ID NO: 8-747 and 771-824, (b) the sense RNA strand is 19-29 nucleotides in length and is complementary to 14-29 nucleotides from the antisense RNA strand, and (c) the double stranded RNA molecule has a double stranded region of 14-29 nucleotides in length and a 3' overhang region of 0-5 nucleotides in length.

P19. The therapeutic compound according to any one of claims P1-P7, P10, P11, P14, and P15, wherein the API is siRNA, the siRNA being a double-stranded RNA molecule including an antisense RNA strand and a sense RNA strand, wherein:

(a) the antisense RNA strand is 19-29 nucleotides in length and is complementary to contiguous nucleotides in a target mammalian mRNA sequence, the mRNA sequence being selected from the group consisting of SEQ ID NO: 22-747 and 771-824,
(b) the sense RNA strand is 19-29 nucleotides in length and is complementary to 14-29 nucleotides from the antisense RNA strand, and
(c) the double stranded RNA molecule has a double stranded region of 14-29 nucleotides in length and a 3' overhang region of 0-5 nucleotides in length.

P20. The therapeutic compound according to any one of claims P1-P7, P10, P11, P14, and P15, wherein the API is siRNA, the siRNA being a double-stranded RNA molecule including an antisense RNA strand and a sense RNA strand, wherein:
(a) the antisense RNA strand is 19-29 nucleotides in length and is complementary to contiguous nucleotides in a target mammalian mRNA sequence, the mRNA sequence being selected from the group consisting of SEQ ID NO: 22-37,
(b) the sense RNA strand is 19-29 nucleotides in length and is complementary to 14-29 nucleotides from the antisense RNA strand, and
(c) the double stranded RNA molecule has a double stranded region of 14-29 nucleotides in length and a 3' overhang region of 0-5 nucleotides in length.

P21. The therapeutic compound according to any one of claims P1-P7, P10, P11, P14, and P15, wherein the API is siRNA, the siRNA being a double-stranded RNA molecule including an antisense RNA strand and a sense RNA strand, wherein:
(a) the antisense RNA strand is 19-29 nucleotides in length and is complementary to contiguous nucleotides in a target mammalian mRNA sequence, the mRNA sequence being selected from the group consisting of SEQ ID NO: 38-39,
(b) the sense RNA strand is 19-29 nucleotides in length and is complementary to 14-29 nucleotides from the antisense RNA strand, and
(c) the double stranded RNA molecule has a double stranded region of 14-29 nucleotides in length and a 3' overhang region of 0-5 nucleotides in length.

P22. The therapeutic compound according to any one of claims P1-P7, P10, P11, P14, and P15, wherein the API is siRNA, the siRNA being a double-stranded RNA molecule including an antisense RNA strand and a sense RNA strand, wherein:
(a) the antisense RNA strand is 19-29 nucleotides in length and is complementary to contiguous nucleotides in a target mammalian mRNA sequence, the mRNA sequence being selected from the group consisting of SEQ ID NO: 40-43,
(b) the sense RNA strand is 19-29 nucleotides in length and is complementary to 14-29 nucleotides from the antisense RNA strand, and
(c) the double stranded RNA molecule has a double stranded region of 14-29 nucleotides in length and a 3' overhang region of 0-5 nucleotides in length.

P23. The therapeutic compound according to any one of claims P1-P7, P10, P11, P14, and P15, wherein the API is siRNA, the siRNA being a double-stranded RNA molecule including an antisense RNA strand and a sense RNA strand, wherein:
(a) the antisense RNA strand is 19-29 nucleotides in length and is complementary to contiguous nucleotides in a target mammalian mRNA sequence, the mRNA sequence being selected from the group consisting of SEQ ID NO: 44-51,
(b) the sense RNA strand is 19-29 nucleotides in length and is complementary to 14-29 nucleotides from the antisense RNA strand, and
(c) the double stranded RNA molecule has a double stranded region of 14-29 nucleotides in length and a 3' overhang region of 0-5 nucleotides in length.

P24. The therapeutic compound according to any one of claims P1-P7, P10, P12, and P16, wherein the API is siRNA, the siRNA being a double-stranded RNA molecule including an antisense RNA strand and a sense RNA strand, wherein:
(a) the antisense RNA strand is 19-29 nucleotides in length and is complementary to contiguous nucleotides in a target mammalian mRNA sequence, the mRNA sequence being selected from the group consisting of SEQ ID NO: 8-21, 482-486, and 748-765,
(b) the sense RNA strand is 19-29 nucleotides in length and is complementary to 14-29 nucleotides from the antisense RNA strand, and
(c) the double stranded RNA molecule has a double stranded region of 14-29 nucleotides in length and a 3' overhang region of 0-5 nucleotides in length.

P25. The therapeutic compound according to any one of claims P1-P7, P10, P12, and P16, wherein the API is siRNA, the siRNA being a double-stranded RNA molecule including an antisense RNA strand and a sense RNA strand, wherein:
(a) the antisense RNA strand is 19-29 nucleotides in length and is complementary to contiguous nucleotides in a target mammalian mRNA sequence, the mRNA sequence being selected from the group consisting of SEQ ID NO: 482-486 and 748-765,
(b) the sense RNA strand is 19-29 nucleotides in length and is complementary to 14-29 nucleotides from the antisense RNA strand, and
(c) the double stranded RNA molecule has a double stranded region of 14-29 nucleotides in length and a 3' overhang region of 0-5 nucleotides in length.

P26. The therapeutic compound according to any one of claims P1-P7, P10, P13, and P17, wherein the API is siRNA, the siRNA being a double-stranded RNA molecule including an antisense RNA strand and a sense RNA strand, wherein:
(a) the antisense RNA strand is 19-29 nucleotides in length and is complementary to contiguous nucleotides in a target mammalian mRNA sequence, the mRNA sequence being selected from the group consisting of SEQ ID NO: 8-21, 40-43, and 766-770,
(b) the sense RNA strand is 19-29 nucleotides in length and is complementary to 14-29 nucleotides from the antisense RNA strand, and
(c) the double stranded RNA molecule has a double stranded region of 14-29 nucleotides in length and a 3' overhang region of 0-5 nucleotides in length.

P27. The therapeutic compound according to any one of claims P1-P7, P10, P13, and P17, wherein the API is siRNA, the siRNA being a double-stranded RNA molecule including an antisense RNA strand and a sense RNA strand, wherein:
(a) the antisense RNA strand is 19-29 nucleotides in length and is complementary to contiguous nucleotides in a target mammalian mRNA sequence, the mRNA sequence being selected from the group consisting of SEQ ID NO: 40-43 and 766-770,
(b) the sense RNA strand is 19-29 nucleotides in length and is complementary to 14-29 nucleotides from the antisense RNA strand, and (c) the double stranded RNA molecule has a double stranded region of 14-29 nucleotides in length and a 3' overhang region of 0-5 nucleotides in length.

P28. The therapeutic compound according to any one of claims P1-P7, P10, P11, P14, and P15, wherein the API is shRNA, the shRNA being a single-stranded RNA molecule of 44-71 nucleotides in length, and having, in a 5' to 3' direction:
- a first region of 19-29 nucleotides at the 5' end of the single-stranded RNA molecule, the first region having a first sequence;
- a second region of 4-11 nucleotides directly adjacent to the first region, the second region having a second sequence;
- a third region of 19-29 nucleotides directly adjacent to the second region, the third region having a third sequence; and
- a fourth region of 2 nucleotides at the 3' end of the single-stranded RNA molecule, directly adjacent to the third region, the fourth region having a fourth sequence, wherein:
(a) the first region has the same number of nucleotides as the third region,
(b) the third sequence is the reverse-complement of the first sequence,
(c) the third region is complementary to contiguous nucleotides in a target mammalian mRNA sequence, the mRNA sequence being selected from the group consisting of SEQ ID NO: 8-747 and 771-824, and
(d) the single-stranded RNA molecule is configured to form a stem loop structure, the first region base pairing with the third region to form a stem, the second region forming a loop, and the fourth region forming a 3' overhang.

P29. The therapeutic compound according to any one of claims P1-P7, P10, P11, P14, and P15, wherein the API is shRNA, the shRNA being a single-stranded RNA molecule of 44-71 nucleotides in length, and having, in a 5' to 3' direction:
- a first region of 19-29 nucleotides at the 5' end of the single-stranded RNA molecule, the first region having a first sequence;
- a second region of 4-11 nucleotides directly adjacent to the first region, the second region having a second sequence;
- a third region of 19-29 nucleotides directly adjacent to the second region, the third region having a third sequence; and
- a fourth region of 2 nucleotides at the 3' end of the single-stranded RNA molecule, directly adjacent to the third region, the fourth region having a fourth sequence, wherein:
(a) the first region has the same number of nucleotides as the third region,
(b) the third sequence is the reverse-complement of the first sequence,
(c) the third region is complementary to contiguous nucleotides in a target mammalian mRNA sequence, the mRNA sequence being selected from the group consisting of SEQ ID NO: 22-747 and 771-824, and
(d) the single-stranded RNA molecule is configured to form a stem loop structure, the first region base pairing with the third region to form a stem, the second region forming a loop, and the fourth region forming a 3' overhang.

P30. The therapeutic compound according to any one of claims P1-P7, P10, P11, P14, and P15, wherein the API is shRNA, the shRNA being a single-stranded RNA molecule of 44-71 nucleotides in length, and having, in a 5' to 3' direction:
- a first region of 19-29 nucleotides at the 5' end of the single-stranded RNA molecule, the first region having a first sequence;
- a second region of 4-11 nucleotides directly adjacent to the first region, the second region having a second sequence;
- a third region of 19-29 nucleotides directly adjacent to the second region, the third region having a third sequence; and
- a fourth region of 2 nucleotides at the 3' end of the single-stranded RNA molecule, directly adjacent to the third region, the fourth region having a fourth sequence, wherein:
(a) the first region has the same number of nucleotides as the third region,
(b) the third sequence is the reverse-complement of the first sequence,
(c) the third region is complementary to contiguous nucleotides in a target mammalian mRNA sequence, the mRNA sequence being selected from the group consisting of SEQ ID NO: 22-37, and
(d) the single-stranded RNA molecule is configured to form a stem loop structure, the first region base pairing with the third region to form a stem, the second region forming a loop, and the fourth region forming a 3' overhang.

P31. The therapeutic compound according to any one of claims P1-P7, P10, P11, P14, and P15, wherein the API is shRNA, the shRNA being a single-stranded RNA molecule of 44-71 nucleotides in length, and having, in a 5' to 3' direction:
- a first region of 19-29 nucleotides at the 5' end of the single-stranded RNA molecule, the first region having a first sequence;
- a second region of 4-11 nucleotides directly adjacent to the first region, the second region having a second sequence;
- a third region of 19-29 nucleotides directly adjacent to the second region, the third region having a third sequence; and
- a fourth region of 2 nucleotides at the 3' end of the single-stranded RNA molecule, directly adjacent to the third region, the fourth region having a fourth sequence, wherein:
(a) the first region has the same number of nucleotides as the third region,
(b) the third sequence is the reverse-complement of the first sequence,
(c) the third region is complementary to contiguous nucleotides in a target mammalian mRNA sequence, the mRNA sequence being selected from the group consisting of SEQ ID NO: 38-39, and
(d) the single-stranded RNA molecule is configured to form a stem loop structure, the first region base pairing with the third region to form a stem, the second region forming a loop, and the fourth region forming a 3' overhang.

P32. The therapeutic compound according to any one of claims P1-P7, P10, P11, P14, and P15, wherein the API is shRNA, the shRNA being a single-stranded RNA molecule of 44-71 nucleotides in length, and having, in a 5' to 3' direction:
- a first region of 19-29 nucleotides at the 5' end of the single-stranded RNA molecule, the first region having a first sequence;
- a second region of 4-11 nucleotides directly adjacent to the first region, the second region having a second sequence;
- a third region of 19-29 nucleotides directly adjacent to the second region, the third region having a third sequence; and
- a fourth region of 2 nucleotides at the 3' end of the single-stranded RNA molecule, directly adjacent to the third region, the fourth region having a fourth sequence, wherein:
- (a) the first region has the same number of nucleotides as the third region,
- (b) the third sequence is the reverse-complement of the first sequence,
- (c) the third region is complementary to contiguous nucleotides in a target mammalian mRNA sequence, the mRNA sequence being selected from the group consisting of SEQ ID NO: 40-43, and
- (d) the single-stranded RNA molecule is configured to form a stem loop structure, the first region base pairing with the third region to form a stem, the second region forming a loop, and the fourth region forming a 3' overhang.

P33. The therapeutic compound according to any one of claims P1-P7, P10, P11, P14, and P15, wherein the API is shRNA, the shRNA being a single-stranded RNA molecule of 44-71 nucleotides in length, and having, in a 5' to 3' direction:
- a first region of 19-29 nucleotides at the 5' end of the single-stranded RNA molecule, the first region having a first sequence;
- a second region of 4-11 nucleotides directly adjacent to the first region, the second region having a second sequence;
- a third region of 19-29 nucleotides directly adjacent to the second region, the third region having a third sequence; and
- a fourth region of 2 nucleotides at the 3' end of the single-stranded RNA molecule, directly adjacent to the third region, the fourth region having a fourth sequence, wherein:
- (a) the first region has the same number of nucleotides as the third region,
- (b) the third sequence is the reverse-complement of the first sequence,
- (c) the third region is complementary to contiguous nucleotides in a target mammalian mRNA sequence, the mRNA sequence being selected from the group consisting of SEQ ID NO: 44-51, and
- (d) the single-stranded RNA molecule is configured to form a stem loop structure, the first region base pairing with the third region to form a stem, the second region forming a loop, and the fourth region forming a 3' overhang.

P34. The therapeutic compound according to any one of claims P1-P7, P10, P12, and P16, wherein the API is shRNA, the shRNA being a single-stranded RNA molecule of 44-71 nucleotides in length, and having, in a 5' to 3' direction:
- a first region of 19-29 nucleotides at the 5' end of the single-stranded RNA molecule, the first region having a first sequence;
- a second region of 4-11 nucleotides directly adjacent to the first region, the second region having a second sequence;
- a third region of 19-29 nucleotides directly adjacent to the second region, the third region having a third sequence; and
- a fourth region of 2 nucleotides at the 3' end of the single-stranded RNA molecule, directly adjacent to the third region, the fourth region having a fourth sequence, wherein:
- (a) the first region has the same number of nucleotides as the third region,
- (b) the third sequence is the reverse-complement of the first sequence,
- (c) the third region is complementary to contiguous nucleotides in a target mammalian mRNA sequence, the mRNA sequence being selected from the group consisting of SEQ ID NO: 8-21, 482-486, and 748-765, and
- (d) the single-stranded RNA molecule is configured to form a stem loop structure, the first region base pairing with the third region to form a stem, the second region forming a loop, and the fourth region forming a 3' overhang.

P35. The therapeutic compound according to any one of claims P1-P7, P10, P12, and P16, wherein the API is shRNA, the shRNA being a single-stranded RNA molecule of 44-71 nucleotides in length, and having, in a 5' to 3' direction:
- a first region of 19-29 nucleotides at the 5' end of the single-stranded RNA molecule, the first region having a first sequence;
- a second region of 4-11 nucleotides directly adjacent to the first region, the second region having a second sequence;
- a third region of 19-29 nucleotides directly adjacent to the second region, the third region having a third sequence; and
- a fourth region of 2 nucleotides at the 3' end of the single-stranded RNA molecule, directly adjacent to the third region, the fourth region having a fourth sequence, wherein:
- (a) the first region has the same number of nucleotides as the third region,
- (b) the third sequence is the reverse-complement of the first sequence,
- (c) the third region is complementary to contiguous nucleotides in a target mammalian mRNA sequence, the mRNA sequence being selected from the group consisting of SEQ ID NO: 482-486 and 748-765, and
- (d) the single-stranded RNA molecule is configured to form a stem loop structure, the first region base pairing with the third region to form a stem, the second region forming a loop, and the fourth region forming a 3' overhang.

P36. The therapeutic compound according to any one of claims P1-P7, P10, P13, and P17, wherein the API is shRNA, the shRNA being a single-stranded RNA molecule of 44-71 nucleotides in length, and having, in a 5' to 3' direction:

a first region of 19-29 nucleotides at the 5' end of the single-stranded RNA molecule, the first region having a first sequence;

a second region of 4-11 nucleotides directly adjacent to the first region, the second region having a second sequence;

a third region of 19-29 nucleotides directly adjacent to the second region, the third region having a third sequence; and a fourth region of 2 nucleotides at the 3' end of the single-stranded RNA molecule, directly adjacent to the third region, the fourth region having a fourth sequence, wherein:

(a) the first region has the same number of nucleotides as the third region, (b) the third sequence is the reverse-complement of the first sequence, (c) the third region is complementary to contiguous nucleotides in a target mammalian mRNA sequence, the mRNA sequence being selected from the group consisting of SEQ ID NO: 8-21, 40-43, and 766-770, and (d) the single-stranded RNA molecule is configured to form a stem loop structure, the first region base pairing with the third region to form a stem, the second region forming a loop, and the fourth region forming a 3' overhang.

P37. The therapeutic compound according to any one of claims P1-P7, P10, P13, and P17, wherein the API is shRNA, the shRNA being a single-stranded RNA molecule of 44-71 nucleotides in length, and having, in a 5' to 3' direction:

a first region of 19-29 nucleotides at the 5' end of the single-stranded RNA molecule, the first region having a first sequence;

a second region of 4-11 nucleotides directly adjacent to the first region, the second region having a second sequence;

a third region of 19-29 nucleotides directly adjacent to the second region, the third region having a third sequence; and a fourth region of 2 nucleotides at the 3' end of the single-stranded RNA molecule, directly adjacent to the third region, the fourth region having a fourth sequence, wherein:

(a) the first region has the same number of nucleotides as the third region, (b) the third sequence is the reverse-complement of the first sequence, (c) the third region is complementary to contiguous nucleotides in a target mammalian mRNA sequence, the mRNA sequence being selected from the group consisting of SEQ ID NO: 40-43 and 766-770, and (d) the single-stranded RNA molecule is configured to form a stem loop structure, the first region base pairing with the third region to form a stem, the second region forming a loop, and the fourth region forming a 3' overhang.

P38. The therapeutic compound according to any one of claims P1-P7, P10, P11, P14, and P15, wherein the API is an miRNA selected from the group consisting of SEQ ID NO: 825-844, 849-851, 853, 855, 857, 864, 865, and 867-883.

P39. The therapeutic compound according to any one of claims P1-P7, P10, P11, P14, and P15, wherein the API is an antimiR, the antimiR being a single-stranded nucleic acid molecule of 12-25 nucleotides in length, the antimiR having a sequence of 12-25 contiguous nucleotides that is complementary to contiguous nucleotides in a target mature miRNA product sequence, the mature miRNA product sequence being selected from the group consisting of SEQ ID NO: 884-908, wherein the contiguous nucleotides in the mature miRNA product sequence includes, in a 5' to 3' direction, nucleotides 2 to 8 of the mature miRNA product sequence.

P40. The therapeutic compound according to any one of claims P1-P7, P10, P11, P14, and P15, wherein the API is a small molecule selected from the group consisting of methotrexate; doxorubicin; vinca alkaloids; camptothecin analogues; microtubule-disrupting agents such as auristatins (e.g., MMAE and MMAF) and maytansinoids (e.g., DM1 and DM4); and DNA-damaging agents such as DNA topoisomerase I inhibitors (e.g., SN-38 and exatecan), double-strand break agents (e.g., calicheamicin), cross-linkers (e.g., pyrrolobenzodiazepine dimer-PBD), and alkylators (e.g., duocarmycin and indolinobenzodiazepine dimer-IGN).

P41. The therapeutic compound according to any one of claims P1-P7, P10, P11, P14, and P15, wherein the API is a protein, the protein having an amino acid sequence selected from the group consisting of SEQ ID NO: 909-929 and homologs thereof.

P42. The therapeutic compound according to any one of claims P1-P7, P10, P11, P14, and P15, wherein the API is a protein, the protein consisting of an amino acid sequence selected from the group consisting of SEQ ID NO: 909-929 and homologs thereof.

P43. The therapeutic compound according to any one of claims P1-P7, P10, P11, P14, and P15, wherein the API is an mRNA encoding an amino acid sequence selected from the group consisting of SEQ ID NO: 909-929 and homologs thereof, the mRNA being configured to be translated in the target cell to produce a protein comprising the amino acid sequence.

P44. The therapeutic compound according to any one of claims P1-P7, P10, P11, P14, and P15, wherein the API is an mRNA encoding an amino acid sequence selected from the group consisting of SEQ ID NO: 909-929 and homologs thereof, the mRNA being configured to be translated in the target cell to produce a protein consisting of the amino acid sequence.

P45. The therapeutic compound according to any one of claims P43 and P44, wherein the mRNA is codon optimized.

P46. A method of treating cancer in a mammalian subject in need thereof, the method comprising administering a therapeutically effective amount of the therapeutic compound according to any one of claims P1-P1, P14, P15, P18-P23, P28-P33, and P38-P45.

P47. A method of treating viral infection in a mammalian subject in need thereof, the method comprising administering a therapeutically effective amount of the therapeutic compound according to any one of claims P1-P10, P12, P16, P24, P25, P34, and P35.

P48. A method of treating fibrotic disease in a mammalian subject in need thereof, the method comprising administering a therapeutically effective amount of the therapeutic compound according to any one of claims P1-P10, P13, P17, P26, P27, P36, and P37.

P49. The therapeutic compound according to any one of claims P1-P45, wherein the mammalian subject is a human.

P50. The method according to any one of claims P46-P48, wherein the mammalian subject is a human.

P51. A pharmaceutical composition comprising the therapeutic compound according to any one of claims P1-P45 and P49 and a pharmaceutically acceptable carrier.

The embodiments of the invention described above are intended to be merely exemplary; numerous variations and modifications will be apparent to those skilled in the art. All such variations and modifications are intended to be within the scope of the present invention as defined in any appended claims.

SEQUENCE LISTING

The patent contains a lengthy sequence listing. A copy of the sequence listing is available in electronic form from the USPTO web site (https://seqdata.uspto.gov/?pageRequest=docDetail&DocID=US12006502B2). An electronic copy of the sequence listing will also be available from the USPTO upon request and payment of the fee set forth in 37 CFR 1.19(b)(3).

What is claimed is:

1. A therapeutic compound for red blood cell-mediated (RBC-mediated) delivery in a mammalian subject to a fibrotic cell expressing CD47, the therapeutic compound comprising:
 a CD47-binding protein conjugated to an active pharmaceutical ingredient (API) so as to form a conjugate;
 wherein:
 the CD47-binding protein is selected from the group consisting of wild type thrombospondin-1 (TSP-1) (SEQ ID NO: 7), wild type SIRPγ (SEQ ID NO: 4), vSIRPγ-1 (SEQ ID NO: 5), vSIRPγ-2 (SEQ ID NO: 6), ALX148 (SEQ ID NO: 962), TTI-661 (SEQ ID NO: 963), TTI-662 (SEQ ID NO: 964), a homolog of any of the foregoing, and combinations thereof, and is configured to bind the conjugate to CD47 of a red blood cell of the subject so as to enable transport of the conjugate, through the subject's circulatory system, to the fibrotic cell, so that (i) the CD47-binding protein, being configured to bind the conjugate to the CD47 of the red blood cell, binds the CD47 of the fibrotic cell, thus transferring the conjugate from the red blood cell to the fibrotic cell so as to form a conjugate-CD47 complex on the fibrotic cell, thereby blocking CD47 and inhibiting CD47 activity as an immune escape mechanism of the fibrotic cell, and (ii) the conjugate is taken up by the fibrotic cell via endocytosis of the conjugate-CD47 complex, thereby further inhibiting the immune escape mechanism of the fibrotic cell and delivering the API into the fibrotic cell; and
 the API is siRNA, the siRNA being a double-stranded RNA molecule including an antisense RNA strand and a sense RNA strand,
 wherein:
 (a) the antisense RNA strand is 19-29 nucleotides in length and is complementary to contiguous nucleotides in a target mammalian mRNA sequence, the mRNA sequence being selected from the group consisting of SEQ ID NO: 8-21, 40-43, and 766-770,
 (b) the sense RNA strand is 19-29 nucleotides in length and is complementary to 14-29 nucleotides from the antisense RNA strand, and
 (c) the double stranded RNA molecule has a double stranded region of 14-29 nucleotides in length and a 3' overhang region of 0-5 nucleotides in length.

2. The therapeutic compound of claim 1, wherein the CD47-binding protein is conjugated to the API by a linker.

3. The therapeutic compound according to claim 2, wherein the linker is cleavable.

4. The therapeutic compound of claim 1, wherein the fibrotic cell is associated with cystic fibrosis.

5. A therapeutic compound for RBC-mediated delivery in a mammalian subject to a fibrotic cell expressing CD47, the therapeutic compound comprising:
 a CD47-binding protein conjugated to an API so as to form a conjugate;
 wherein:
 the CD47-binding protein is selected from the group consisting of wild type thrombospondin-1 (TSP-1) (SEQ ID NO: 7), wild type SIRPγ (SEQ ID NO: 4), vSIRPγ-1 (SEQ ID NO: 5), vSIRPγ-2 (SEQ ID NO: 6), ALX148 (SEQ ID NO: 962), TTI-661 (SEQ ID NO: 963), TTI-662 (SEQ ID NO: 964), a homolog of any of the foregoing, and combinations thereof, and is configured to bind the conjugate to CD47 of a red blood cell of the subject so as to enable transport of the conjugate, through the subject's circulatory system, to the fibrotic cell, so that (i) the CD47-binding protein, being configured to bind the conjugate to the CD47 of the red blood cell, binds the CD47 of the fibrotic cell, thus transferring the conjugate from the red blood cell to the fibrotic cell so as to form a conjugate-CD47 complex on the fibrotic cell, thereby blocking CD47 and inhibiting CD47 activity as an immune escape mechanism of the fibrotic cell, and (ii) the conjugate is taken up by the fibrotic cell via endocytosis of the conjugate-CD47 complex, thereby further inhibiting the immune escape mechanism of the fibrotic cell and delivering the API into the fibrotic cell; and
 the API is shRNA, the shRNA being a single-stranded RNA molecule of 44-71 nucleotides in length, and having, in a 5' to 3' direction:
 a first region of 19-29 nucleotides at the 5' end of the single-stranded RNA molecule, the first region having a first sequence;
 a second region of 4-11 nucleotides directly adjacent to the first region, the second region having a second sequence;
 a third region of 19-29 nucleotides directly adjacent to the second region, the third region having a third sequence; and
 a fourth region of 2 nucleotides at the 3' end of the single-stranded RNA molecule, directly adjacent to the third region, the fourth region having a fourth sequence,
 wherein:
 (a) the first region has the same number of nucleotides as the third region,
 (b) the third sequence is the reverse-complement of the first sequence,
 (c) the third region is complementary to contiguous nucleotides in a target mammalian mRNA sequence, the mRNA sequence being selected from the group consisting of SEQ ID NO: 8-21, 40-43, and 766-770, and
 (d) the single-stranded RNA molecule is configured to form a stem loop structure, the first region base pairing with the third region to form a stem, the second region forming a loop, and the fourth region forming a 3' overhang.

6. The therapeutic compound of claim 5, wherein the CD47-binding protein is conjugated to the API by a linker.

7. The therapeutic compound of claim 6, wherein the linker is cleavable.

8. The therapeutic compound of claim 5, wherein the fibrotic cell is associated with cystic fibrosis.

* * * * *